US006913904B2

(12) United States Patent
Ye et al.

(10) Patent No.: US 6,913,904 B2
(45) Date of Patent: Jul. 5, 2005

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Jane Ye, Boyds, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 512 days.

(21) Appl. No.: 09/817,198

(22) Filed: Mar. 27, 2001

(65) Prior Publication Data

US 2002/0146758 A1 Oct. 10, 2002

(51) Int. Cl.7 ................................................ C12P 21/06

(52) U.S. Cl. .................... 435/69.1; 536/23.1; 536/23.5; 435/320.1; 435/325; 530/350

(58) Field of Search ......................... 530/350; 536/23.5, 536/23.1, 24.1; 435/320.1, 325, 69.1

(56) References Cited

FOREIGN PATENT DOCUMENTS

| | | | |
|---|---|---|---|
| WO | WO-0154733 | A1 * | 8/2001 |
| WO | WO-0218424 | A * | 3/2002 |

* cited by examiner

*Primary Examiner*—Larry R. Helms
*Assistant Examiner*—Stephen L. Rawlings
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

9 Claims, 20 Drawing Sheets

```
   1 TGCCCGCTGC CCGCCCGCAG TTCCCGGCCC CGCTGGCCCC AGTCATGGCG
  51 AAGCAGTACG ATGTGCTGTT CCGGCTGCTG CTGATCGGGG ACTCCGGGGT
 101 GGGCAAGACC TGCCTGCTGT GCCGCTTCAC CGACAACGAG TTCCACTCCT
 151 CGCACATCTC CACCATCGGT GTTGACTTTA AGATGAAGAC CATAGAGGTA
 201 GACGGCATCA AAGTGCGGAT ACAGATCTGG GACACTGCAG GGCAGGAGAG
 251 ATACCAGACC ATCACAAAGC AGTACTATCG GCGGGCCCAG GGGATATTTT
 301 TGGTCTATGA CATTAGCAGC GAGCGCTCTT ACCAGCACAT CATGAAGTGG
 351 GTCAGTGACG TGGATGAGTA CGCACCAGAA GGCGTCCAGA AGATCCTTAT
 401 TGGGAATAAG GCTGATGAGG AGCAGAAACG GCAGGTGGGA AGAGAGCAAG
 451 GGCAGCAGCT GGCGAAGGAG TATGGCATGG ACTTCTATGA AACAAGTGCC
 501 TGCACCAACC TCAACATTAA AGAGTCATTC ACGCGTCTGA CAGAGCTGGT
 551 GCTGCAGGCC CATAGGAAGG AGCTGGAAGG CCTCCGGATG CGTGCCAGCA
 601 ATGAGTTGGC ACTGGCAGAG CTGGAGGAGG AGGAGGGCAA ACCCGAGGGC
 651 CCAGCGAACT CTTCGAAAAC CTGCTGGTGC TGAGTCCTGT GTGGGGCACC
 701 CCACACGACA CCCCTCTTCC CTCAGGAGGC CCGTGGGCAG ACAGGGGAGC
 751 CGGGGCTTTG CCCTGCTGCT GTCCTCTCGT GTGATGACCC TATTGAGTAT
 801 CAGTAGCCAC TACTCCCCCT GCCTGGCCCT GAGAGCGGCT CTGCTGTCAT
 851 CTCAAGCAGC CCCTGTCCCC AGCCCGTCCA CCCTGGAGTG GTCTTCTTCA
 901 GCCTGTTTCC CCAGCCACAG GCCTGCTACG ACCCCCACGA TGTGCCGCAA
 951 GCACTGTCTC ACCATCCCGC ACCCACCAGA CAACAGCCAG GGCTGGAGTC
1001 CAGGCCACTT TCAGCTGCTC CTTTCTCCGT GCATCGTGTC TCTTCTCTGC
1051 TTTTTCTCTC TTCCCCCACT TCTCTTTCTC TGACCCCTCC CCTCCGGTGC
1101 GTTTCGTATC AAAGCTCCTC AAACCCCGTC CCCCGTGTGT CCTGCTGTGT
1151 GCAGCTCGCT CTTTCCTTCC TTCCTAAGCT ATCCAAGGGG ATGGACCCAG
1201 GCTCGTGGGG AGGTTCCACC CTTGGATCCA GGAAGAACCC TCCACCCTGC
1251 CTCGTGGGTG GGCCAAAGGC TACAGGGTGC TTCTTCCTCT TCCCCCACCC
1301 CCACTGTCCC TCATGTGCCA TGGGCCTGCC TCCCCAGTGA CCTGCGAAAG
1351 TGGAGCATCG AGGTAGGAGG GAAACAGCAA CCGGGGAGTC CTCGAGCCTG
1401 GGGCTGCCCT ACCTCTACCC ATTCCCCGAC CAGAGCTTTG CCCTTGCTTG
1451 GCTGCCCGCC TGCCTCTTTG GGGAACTGAG CTCAGAGGCA GGTGCTTCAG
1501 AGAAGGAAAC AAAATGAGGG GTGGCAGGGA TAAAAAGTCA CCTCCATTCT
1551 CTACCTCCCA TGCAGCATGA ACACAATTTC TCTCCACCTG GCTCCCAAAT
1601 TTAAAGATGT GGACCAAGGC CTGTGGGTAC TCCAGGGGCA AGGAGAGCCC
1651 TGGGGTCAGT GACACTGTCA GGCCAACCAT GCACTCCACA AAGGGGAGCA
1701 TTTGGAAATG AAGGACTAGC TCCTATGTAT CAGGTTAAGA GCAAGGGAGA
1751 GCTGGCCAGG GACAGCAGTT TGCACAGCAG AGGGGAATGT AGCAACAGCA
1801 GGGCCTCCTA GGCCCCATCT TCCATTTCTT AGGTAAGAAG AGCATTTCCT
1851 CAGACTCCCA GGCGGAGGAC TGAGCCTAGC CTTCAGCAAC CAAGGTTCTC
1901 CTGGGACCCA AAGTTTATGG GAGAAGGGCA AAGACTTCAT GGGAAGAGAG
1951 AAGGAAGGCC CTGGGTAGAA ACGCTTGGTG CTGTTCTCTT TGGCCTTTAA
2001 GACAAAGCGC TCATCTTGCC CTCTACCTCC TGATAGGCTT GAGGGTTTGC
2051 CAACCACACT GTGGCTACAG GTGGAGGGAA GAGGACTCCT TCCTCCAGAG
2101 TGCTATGTTC AGGAAGTTTC TTTAACCCCA TATGGCCCAA GAGTAGCTCG
2151 TAGGAGGCCC TTTAAAGACG GAACAAGTAA TTTACCAGTT CTACTGGGGT
2201 TCCTGCCCAC CGTCCCAAGG TGGGCGAGGC CTAGGAAGAG GGTCATTCTT
2251 AAGCCACACA TTAGCTGCAC TGCGTGGCTG CAGCCAAAAC AAAGAACTGG
2301 GTGTTGAGTA TTCATCAACT AAGAACCAAA ATCCAGGGCA CTCATATGTG
2351 AAGGATAAGA ACCTCACTTC CTTACTCCTC CAAAAAGAAG TGGGGAAAGA
2401 ACCATCAAAC CTTTCCTCCT GACTTACCAA ACCAGGAAAA CAGCAGGAGA
2451 GGGTGGCTCA GGACTTAGGG ACAGGGTATA GCTTAGATGG TGGAAAGCAA
2501 AGGAGAGCAG GAAGTTGTAA ATCACTGGCT AATGAGAAAA GGAGACAGCT
2551 AACTCTAGGA TGAAGCTGTG ACTAGGCTGG AGTTGCTTCC TTGAAGATGG
2601 GACTCCTTGG GTATCAAGAC CTATGCCACA TCACACTGGG GCTAGGGAAG
2651 TAGGTGATGC CAGCCCTCAA GTCTGTCTTC AGCCAGGGAC TTGAGAAGTT
2701 ATATTGGGCA GTGGCTCCAA TCTGTGGACC AGTATTTCAG CTTTCCCTGA
2751 AGATCAGGCA GGGTGCCATT CATTGTCTTT CTCTCCTAGC CCCCTCAGGA
2801 AAGAAGGACT ATATTTGTAC TGTACCCTAG GGGTTCTGGA AGGGAAAACA
2851 TGGAATCAGG ATTCTATAGA CTGATAGGCC CTATCCACAA GGGCCATGAC
2901 TGGGAAAAGG TATGGGAGCA GAAGGAGAAT TGGGATTTTA GGGTGCAGCT
2951 ACGCTCACCC TAAACTTTTG GTGGCCTGGG GCATGTCTTG AGGCCCAGAC
```

FIGURE 1A

```
3001 TGTTAAGCAG GCTCTGCTGG CCTGTTTACT CGTCACCACC TCTGCACCTG
3051 CTGTCTTGAG ACTCCATCCA GCCCCAGGCA CGCCACCTGC TCCTGAGCCT
3101 CCACTATCTC CCTGTGACGG GTGAACTTCG TGTACTGTGT CTCGGGTCCA
3151 TATATGAATT GTGAGCAGGG TTCATCTATT TTAAACACAG ATGTTTACAA
3201 AATAAAGATT ATTTCAAACC ACCAAAAAAA AAAAAAAAAA AAAAAAAAAA
3251 AAAAAAA  (SEQ ID NO:1)
```

FEATURES:

```
5'UTR:        1-44
Start Codon:  45
Stop Codon:   681
3'UTR:        684
```

Homologous proteins:

Top 10 BLAST Hits

| | Score | E |
|---|---|---|
| CRA\|335001101587561 /WO200058473 /org=Homo sapiens /taxon=9... | 428 | e-119 |
| CRA\|18000004937398 /altid=gi\|464561 /def=sp\|P35289\|RB15_RAT RAS... | 423 | e-117 |
| CRA\|18000005187045 /altid=gi\|7498104 /def=pir\|\|T33855 hypotheti... | 220 | 6e-56 |
| CRA\|18000004929618 /altid=gi\|131798 /def=sp\|P24407\|RAB8_HUMAN R... | 216 | 1e-54 |
| CRA\|335001098683352 /altid=gi\|11422744 /def=ref\|XP_001482.1\| TR... | 214 | 4e-54 |
| CRA\|18000005096141 /altid=gi\|2317272 /def=dbj\|BAA21744.1\| (AB00... | 214 | 4e-54 |
| CRA\|18000004952869 /altid=gi\|131848 /def=sp\|P22128\|RAB8_DISOM R... | 212 | 3e-53 |
| CRA\|335001098688905 /altid=gi\|11432830 /def=ref\|XP_007682.1\| RA... | 211 | 4e-53 |
| CRA\|18000004945380 /altid=gi\|131847 /def=sp\|P22127\|RAO1_DISOM R... | 211 | 5e-53 |
| CRA\|18000005163099 /altid=gi\|7705849 /def=ref\|NP_057215.1\| ras-... | 210 | 6e-53 |

BLAST dbEST hits:

| | Score | E |
|---|---|---|
| gi\|12333507 /dataset=dbest /taxon=96... | 626 | e-177 |
| gi\|12120217 /dataset=dbest /taxon=96... | 377 | e-102 |

EXPRESSION INFORMATION FOR MODULATORY USE:

library source:

From BLAST dbEST hits:

gi|12333507 brain
gi|12120217 epid_tumor

From tissue screening panels:

Fetal whole brain

FIGURE 1B

```
  1 MAKQYDVLFR LLLIGDSGVG KTCLLCRFTD NEFHSSHIST IGVDFKMKTI
 51 EVDGIKVRIQ IWDTAGQERY QTITKQYYRR AQGIFLVYDI SSERSYQHIM
101 KWVSDVDEYA PEGVQKILIG NKADEEQKRQ VGREQGQQLA KEYGMDFYET
151 SACTNLNIKE SFTRLTELVL QAHRKELEGL RMRASNELAL AELEEEEGKP
201 EGPANSSKTC WC  (SEQ ID NO:2)
```

FEATURES:

Functional domains and key regions:

[1] PDOC00001 PS00001 ASN_GLYCOSYLATION
N-glycosylation site 205-208 NSSK (SEQ ID NO:6)

[2] PDOC00005 PS00005 PKC_PHOSPHO_SITE
Protein kinase C phosphorylation site

Number of matches: 2

1 92-94 SER
2 206-208 SSK

[3] PDOC00006 PS00006 CK2_PHOSPHO_SITE
Casein kinase II phosphorylation site

Number of matches: 2

1 29-32 TDNE (SEQ ID NO:7)
2 104-107 SDVD (SEQ ID NO:8)

[4] PDOC00007 PS00007 TYR_PHOSPHO_SITE
Tyrosine kinase phosphorylation site 101-109 KWVSDVDEY (SEQ ID NO:9)

[5] PDOC00008 PS00008 MYRISTYL
N-myristoylation site

Number of matches: 2

1 18-23 GVGKTC (SEQ ID NO:10)
2 136-141 GQQLAK (SEQ ID NO:11)

[6] PDOC00017 PS00017 ATP_GTP_A
ATP/GTP-binding site motif A (P-loop)

15-22 GDSGVGKT (SEQ ID NO:12)

[7] PDOC00579 PS00675 SIGMA54_INTERACT_1
Sigma-54 interaction domain ATP-binding region A signature 11-24 LLLIGDSGVGKTCL (SEQ ID NO:13)

FIGURE 2A

```
BLAST Alignment to Top Hit:
>CRA|18000004937398 /altid=gi|464561 /def=sp|P35289|RB15_RAT
          RAS-RELATED PROTEIN RAB-15 /dataset=nraa /length=212
         Length = 212

 Score =  423 bits (1077), Expect = e-117
 Identities = 207/212 (97%), Positives = 209/212 (97%)
 Frame = +3

Query: 45  MAKQYDVLFRLLLIGDSGVGKTCLLCRFTDNEFHSSHISTIGVDFKMKTIEVDGIKVRIQ 224
            MAKQYDVLFRLLLIGDSGVGKTCLLCRFTDNEFHSSHISTIGVDFKMKTIEVDGIKVRIQ
Sbjct: 1   MAKQYDVLFRLLLIGDSGVGKTCLLCRFTDNEFHSSHISTIGVDFKMKTIEVDGIKVRIQ 60

Query: 225 IWDTAGQERYQTITKQYYRRAQGIFLVYDISSERSYQHIMKWVSDVDEYAPEGVQKILIG 404
            IWDTAGQERYQTITKQYYRRAQGIFLVYDISSERSYQHIMKWVSDVDEYAPEGVQKILIG
Sbjct: 61  IWDTAGQERYQTITKQYYRRAQGIFLVYDISSERSYQHIMKWVSDVDEYAPEGVQKILIG 120

Query: 405 NKADEEQKRQVGREQGQQLAKEYGMDFYETSACTNLNIKESFTRLTELVLQAHRKELEGL 584
            NKADEEQKRQVGREQGQQLAKEYGMDFYETSACTNLNIKESFTRLTELVLQAHRKEL+GL
Sbjct: 121 NKADEEQKRQVGREQGQQLAKEYGMDFYETSACTNLNIKESFTRLTELVLQAHRKELDGL 180

Query: 585 RMRASNELALAELEEEEGKPEGPANSSKTCWC 680   (SEQ ID NO:2)
            R  ASNELALAELEE+EGK EGPANSSKTCWC
Sbjct: 181 RTCASNELALAELEEDEGKTEGPANSSKTCWC 212   (SEQ ID NO:4)

>CRA|335001101587561 /dataset=GENESEQ /org=Homo sapiens /taxon=9606
          /mol_type=protein /date=08-FEB-01 /length=218
          /altid=derwent_id|B41604 /altid=derwent_ac|B41604
          /def=Human ORFX ORF1368 polypeptide sequence SEQ ID
          NO:2736 /patent=WO200058473-A2 /pat_section=Claim
         Length = 218

 Score =  428 bits (1088), Expect = e-119
 Identities = 212/218 (97%), Positives = 212/218 (97%), Gaps = 6/218 (2%)
 Frame = +3

Query: 45  MAKQYDVLFRLLLIGDSGVGKTCLLCRFTDNEFHSSHISTIGVDFKMKTIEVDGIKVRIQ 224
            MAKQYDVLFRLLLIGDSGVGKTCLLCRFTDNEFHSSHISTIGVDFKMKTIEVDGIKVRIQ
Sbjct: 1   MAKQYDVLFRLLLIGDSGVGKTCLLCRFTDNEFHSSHISTIGVDFKMKTIEVDGIKVRIQ 60

Query: 225 IWDTAGQERYQTITKQYYRRAQGIFLVYDISSERSYQHIMKWVSDVDEYAPEGVQKILIG 404
            IWDTAGQERYQTITKQYYRRAQGIFLVYDISSERSYQHIMKWVSDVDEYAPEGVQKILIG
Sbjct: 61  IWDTAGQERYQTITKQYYRRAQGIFLVYDISSERSYQHIMKWVSDVDEYAPEGVQKILIG 120

Query: 405 NKADEEQKRQVGREQGQ------QLAKEYGMDFYETSACTNLNIKESFTRLTELVLQAHR 566
            NKADEEQKRQVGREQGQ      QLAKEYGMDFYETSACTNLNIKESFTRLTELVLQAHR
Sbjct: 121 NKADEEQKRQVGREQGQQKCPSLQLAKEYGMDFYETSACTNLNIKESFTRLTELVLQAHR 180

Query: 567 KELEGLRMRASNELALAELEEEEGKPEGPANSSKTCWC 680   (SEQ ID NO:2)
            KELEGLRMRASNELALAELEEEEGKPEGPANSSKTCWC
Sbjct: 181 KELEGLRMRASNELALAELEEEEGKPEGPANSSKTCWC 218   (SEQ ID NO:5)
```

FIGURE 2B

Hmmer search results (Pfam):

| Model | Description | Score | E-value | N |
|---|---|---|---|---|
| PF00071 | Ras family | 323.8 | 8.2e-95 | 1 |
| CE00060 | CE00060 rab_ras_like | 211.0 | 1.8e-59 | 1 |
| PF00006 | ATP synthase alpha/beta family | 4.2 | 2.1 | 1 |

Parsed for domains:

| Model | Domain | seq-f | seq-t | | hmm-f | hmm-t | | score | E-value |
|---|---|---|---|---|---|---|---|---|---|
| PF00006 | 1/1 | 10 | 24 | .. | 203 | 217 | .. | 4.2 | 2.1 |
| CE00060 | 1/1 | 2 | 165 | .. | 16 | 184 | .. | 211.0 | 1.8e-59 |
| PF00071 | 1/1 | 10 | 212 | .] | 1 | 198 | [] | 323.8 | 8.2e-95 |

FIGURE 2C

```
   1 GCTCAAGATT GCACAGCTGG TGAGTGGTGA CACTGGGACT GGAACCCAAG
  51 TGTGCCTTAC TCCAGAGCCC TTGGCATGCA CCTGAAACCC CATGTAAGCC
 101 CACTGTGGAG ACGCGCACCT CGAAATAATG GAATCCACTA CATCAGTTCC
 151 TTTAGCTTTC TGTGTAATCA GAGTAGCTAG CAGGCTCGGG ATTTCGCCCC
 201 CCGGCTTTTT TTTTTTTTTT TTTTTGAGAC AGAGTTTTGC TCTTGTTGCC
 251 CAGGCTGGAG TGCAATGGCG CAATCTCGGC TCACCGCAAC CTTCGCCTCT
 301 CAGGTTCAAG CAATTCTCCT GCCTCAGCCT CCCGAGTAGC TGGGATTACA
 351 GGCACCGGCC ACCACGCCCA GCTAATTTTT TTATATTTTT AGTAGAGATG
 401 GGGTTTCACC ATGTTGGCCA GGCTGGTCTT GAACTTTTCC CCTCTTATTA
 451 TAATTCAGAC ACTTAACCTG AAATATACCT TTTCAAATGA AGTAAATGGG
 501 CTTACCACTT TCCTTGACCT ACTATTGAAA AATACATTCT CCATCCAATA
 551 TTCAGCCTGA AAACAGGTAT GTACATATAT ACTTTTCATT GCTTTTTTTT
 601 TTTTTTTTTT GAGACAAGGT CTCCCTCTGT TGCGCAGGCT GGAGTGCAGT
 651 GTCATGATCT CGGCTCACTG CAGCCTTCCC CTAATGGGTT CAAGCAATCC
 701 TCCCACCTCA GCCTCTCAAG CCTGGGATTA CAGGCGAGCC ACCGTGCCCA
 751 GCTAATTTTT TTTTATTTTT AGTAGAGACT GGGTTTCACT ACATTGGCCA
 801 GGCTGGTCTC CAGCTCCTGA CCTCAAAGTG ATCTGCCCGC CTCAGCCTCC
 851 CAAAGTACTG GGATTACAGG CATGAGCCAA CGCGCCTAGC CTTTCATTGC
 901 TTTTTAAAGA CCTAATAGGC TAGACTTTGC TCTCCCTCAA TACTCGTTGG
 951 TAGGGATAGG CAATTTTCTC AACTCCGGAG AGCATTCATT TGCCTCTCTC
1001 CGGTGCTAAC ACATTCAGTG GTAGGAAACT GGATCTTGAA CAAGGGCCAT
1051 TCATTCTTTG GTGCCACTGG CTATACCACA GAGAAATTTA GGGGTCTGAA
1101 ACAATACATT GGTCACCTGG GCACCTATCC TAAGCACCTT AGAGGGAAAA
1151 CGGAGACTTG CCCGCACACC TCTAAAGGAT TTTGCACTTG GAGATGTTCT
1201 TATGGCCATC TATCTTTTCA CCCTGGTGGA GGCCGTGAAT AGGCATTTTC
1251 CCCATTTAAA GAAAAAATGG GGACGGGGGA GGGCCGTGAC ACAGTCACAC
1301 AGGTAAGGGG CAGCCAGATG GCAGGGAGGG GGAATTCCAC CCACACTCTC
1351 GGGGACTCAT GGAGACGGGT GTTCGAATCC AGATCCTGCT CAAGGCCTTC
1401 CTACCTCGGG TGAGCCCAGC TGAGGTACCA GCCACTGGGG AGCCCGGCCA
1451 GATCCTGCAG ATGCAGGGTG CCACGGCGGG CGGAATTACC GGCGCCAGAC
1501 TTGGGGTGGG ATATGGGGAG AAGTGGTGAG CCCGGAAAGC GGAGCACGGT
1551 AGAAGTGGGC TGGGTGGGGG CTCACCTCAA CTCCCCCATT CGGAGCGTCC
1601 GCGGAAAAAC GAAAACGTTC CCCCGCCCCG GGCAGGAAGG GGTTGGGAGG
1651 GGGGGCTGGC GCCCCGCCCC AGCGTCGCCT GCTCGATGGG GTCCCGCTCT
1701 CCTGCGCGCG CTCCCCGCCC CCTCTCTACC GGGGCGGCGG CGGCGGCGCA
1751 GGGGAAGGGG CGGGCAGGGG CCGCCGCCGG TTTCTCCTCC CACCGCCTCG
1801 CGCCAGCCCA GCCGAGCCGA GCCGAGCCGA GCGGGCGCCG CGCCGGGCTC
1851 CCGCCGCAGC CGCGCTTCCC GGCACCCAGC GAGCGAGTGG GCAGGCGGGC
1901 GGGCGAGGCA GCCGCGGGGG CCGGGCCCGG CGTCCTCCTC GCCGCCCGCA
1951 GCGTCCCCGG GCGGGCGCGG GCCGCGATGG CAGCGGCGGA GCAGGGCTGA
2001 GCCCGCTGCC CGCCCGCAGT TCCCGGCCCC GCTGGCCCCA GTCATGGCGA
2051 AGCAGTACGA TGTGCTGTTC CGGCTGCTGC TGATCGGGGA CTCCGGGGTG
2101 GGCAAGACCT GCCTGCTGTG CCGCTTCACC GACAACGAGT TCCACTCCTC
2151 GCACATCTCC ACCATCGGTA AGGGGCGGTG GCCCGGGGCG CCCCTCCCTC
2201 CCCGCCCGCG GCCCCTTTCC CCGCCGCCCC CGTCCCCAGC TGGGGAGGAA
2251 TTGCCAGCCC CTCCGGCTGG AGGCGGTGGC GCCGGAGGCC GGAGTCCGGG
2301 ATAAATCTCG GGGTGAGCAT AGGTTTTGGC AGGTGAGGGT GTCCCTGCTG
2351 CCTGCCGTCC GGACCAGGGG TGGGGTCTCC CGCCTCTTGC CGGGAAGCCT
2401 TCCGTCCCAT CAAACCGAGA AACCGGGGGT GAGGGGAGCT GGTGTAGGCC
2451 TGGGTACCCC GAGCTGGGGT AGCAAGAATC GTAGCCGCTG GAATAACACC
2501 CCCACACCCC CAGGGGGAGG GGAAGTAAAG CTTCTGCTAC GGAAAAGGGG
2551 GTCAGGGTGG AGACCGGAGT CACTGAGGCG CCCTTGGTTC TGTGGTGACC
2601 CAAGGTGGAG CCGGCGGGGG GCGAGGGGGG GAAGAGAGGA CGTACGGAGG
2651 GGCCACAGGG ATCGAGTTTC CAGGGCAGAG TTGGGAAGGT AAGCCGCAAG
2701 GTGGGACACC TGGGGGAGGA CACAGATAGG GTGAGGAGCC CCTGCGCCTG
2751 GGAAGAGGAG ACATCTGTTC TGAGGGAGGC TAAAGAGGAT GGAGGAGTGT
2801 CAGGAATACC TGCCCAGACC AAGGGGTCAG AAGGCAGGCA GGACCCGCCT
2851 GAGGGCATCT CTCATCTGGC AGTGCTGGAG CCTGTGGTTA GAGGGACAAG
2901 ACCCGGTGGC ATCCCAGACA GCACTATGAT GGGGTCACTT ATTCTAGGAA
2951 TGGGTCCATG GCCTCCCCTC TGAGACAGTC AGTCTCCCGC TTCTAGGCTG
```

FIGURE 3A

```
3001 TGAGGGGCCC CCTCCCTGAG AAGTCTGAGT AGAGGGAATT TCATCCTCAG
3051 CTGCTACCCG GGTCAGCCCT GGAGTAGCCT CTGCATTGCC CAAGCCCCTG
3101 GAAACACCTG CTGGCTGGCT GGTCATCCAT TTGGAATGCT CTCCTAGAAG
3151 TCCCTGCTGC CATCAGGGAT GGGCACCAGC TCTCAGCTTC CTCTTGAGGA
3201 TTCATGTCCA CACCATCCCC CCTCCCCCCA ACACACATTC CTTGCTGAGA
3251 GAGAAGTAGG AGCAGATAGA TACAGCCAGG AGGAACAGAA CCTTCTGGTT
3301 AAGAAGCCAG CTTTATTGTC CAAGAGACCT GAGACCTCAC TGTGGGGCAA
3351 AGCAACCTTG AATATTGCCT AAACTTCTGA GCTTTATTTA GTTTCTCATC
3401 TGTAGAACGG GTATAATAAT TGCACCTACC TGCCAAGTTG TTGTCAAGAT
3451 TAAATGAGAT AACGATTGTT AAGTGCTTAG CACAGCCAGA CACATGGTGA
3501 AGCTCGATAA ATGCTGATTG TTCTTACTGC TATTGCCATT ATCATTGAGC
3551 TTTTAGGGTC TCCTCTCTTT GTTTCACCAA CTTGAAGGGT GAAACAACAG
3601 GACTTAGGGT CAGGGAACAG AACTTGTCCG TCTTTCTCAG AGGAGCTGTA
3651 AGGCCAACTC TTAGGAAACC CAGGAGCTTG GGCTGAGCCA TGGTTTGGAT
3701 GAGAGACATT GCAGAAAGAA GGGGAGCCTA TAGACACTAA GGCTTTGTGC
3751 CTGCCGGGAG GACTTGGGGA AGAGGCAGGT GCAGGAGAAA GGCATGGGCG
3801 TGATGGAGGA AGTGGCAGAG GAACCAGATG GTGTATGAGG ACAGGTTGTG
3851 GGCTCAGGGA CAAAGGGCGG TGGGTTATCC CTTAAGGAAA CTAGGAGTGG
3901 CTATTTTTGG GAGAGGCCTG GTGCTTGGAA CTACTGAGCT ATCTCCAGAG
3951 AGCTGTGGGC TGCCTGGGAG GCCCTGGCTT TGGCCTGAAG AGCTGTTGTT
4001 TGCACCTGCT CTCCTAGTCC CATTCCAAGT CCTATAGGTG ACATGGACTT
4051 TTCCCTTTGA GGGCTTCATT CAACCACCTC ATTTCAGAAG CTCTGGGACT
4101 CCTGCTTAGT GCTGTGGGAG GCAGCCTCCC CTGGGAGACA CATACCCTCC
4151 TTTTTGAGGG CACCCCTCTT TCTAAAATAC CAGGATGGCC CTCTGAGGCT
4201 CGTGCTCTCC TTAAAGAGAG TCCATTGCCT CACACCTCTA ATCATCCACC
4251 CTTCTCCTTG TCCCTTCCCC TTGTAATCTC CCTTCTTAGA CACCTTCTGC
4301 TAATAGGTGA ACACTAAATA GGTCACAGGG ACTTCCTGAA ACCCTCCAGG
4351 GCAGACCACT TTGGGCACAT AGGTGAATCA GTGAACTGAG TAGGGGTGTC
4401 TCTGCAGCAC TGTCTCCCCT CAAGGCCCTT GGTATATTGG CCTAAAACCT
4451 AAAGATGGCT CCCAGATTTC TTCCTCCGCT TCTGACACCC GGGTTCCCCT
4501 TTCTACAGGA CACAGAGGAT TCTCTAGGGT CCCCCTTTCC ACAGGACACA
4551 GAGGACTCTA GGAGTTTGGA TTCCATGGAA TAGAAAGAAA CCTGTCTTTC
4601 TTCACACCAG CCTTTTAAAA TCTGCCCCAC TGGGTATCTT AAATGCTTTC
4651 TTATTTAAAG CTTATTAAGG GACTTGGGAT TCTCCCTTAT CTTGGGCGTG
4701 TTTTTCAGCA TTAACTAAAA CTTAAAGGAA AGAGTTGGAT GGTCAAGAAA
4751 AGCTTTTTCC TTAAGTGATA TGGACAGTTT CTCAAGGAGG TAGAAGGGGC
4801 AGCCAGGAGA CAAATCAAGG AGCCAACGAA ATGAGTGCTA CCAAGTCATA
4851 GTCATTCGCT TATTTTTAAA AAATGCGTGT CCTGTATGCC AGGCTCTGCA
4901 CTGAGACCGA GAGATTCCAA GATGAATAAT ACCTACAGTC ACTGTTCTCA
4951 AATTGTGCAT TACCTAAAAC ACATTACATG ACCATGCTGG CCACTGATCG
5001 AGGCACCTTT CCCAGGGGCT TTTTTTGTGA ATTAAGAAAA CAAGGTAATT
5051 CACCAGTTAT TGCCAAGATA GTTTGGCTTC TTGGCTCATG TGGATATCAC
5101 CTAGGCCAGT ACTTTTGTGA TTTACTGTGT ACTCCACTTT AACGGCCTGC
5151 GATCTTCTAG AGAAGAACCC GCCAGGGAGC AGTGAGAGGC CTCCCTGGTA
5201 GACTGAGACA CTGACTGTCC CTCCCCCTAT CCTTTTCGTC TTTCTGGCCA
5251 GCAGACCAGC AGGTGGCCCT GCCACTGGCT CTGCCACAGG CATTTCCTTT
5301 CTGTGCAGCT GTGCTGGCCT GGCTGGGGGT TGGTGCGAAG GGGTCCCCAA
5351 AATACTACCT TAAACAAATT AATTGAGCAT TCACTACCAA GCTCTGTGCC
5401 AGGCATTTTA GAGACATATT GCAGTCTACG TTTTCTGCCC ACAGAAGCCC
5451 ATAACCTAGA TGGGGAGGCA AGACAAAGGG AAAAACAAAA AACAAAGAGC
5501 TAGTGCCAAA ATGAGATATC TGAAAGAACT TGGTGAATCA CTCTTCAAAT
5551 GTAAAGGATG GATTATGATC ATTGCAGTTA CTCTTAATGA AGGTCTCACA
5601 GTGGGTATCA GAAGCTAAAT TATGATGCAA GATGTACCAT GAGGCAGCCG
5651 GAGAATGGCG ATGGATGGGA TGGGTGAGTG CTATTCCCAC GACTCCATGC
5701 TGTCGGAGGC TGGGGAAGAG AGAGGCCCCT GTGGACTAGA ACCGGCAGGG
5751 AAGGCTGAAG CTAGGCCTCA GTGTGGGCTG CTCGTCAGTT CCTGCAGCAG
5801 AAGGGAGCAG ATGGAGTAAC ATGAGCAGAG ATAACAGAGG TGGGATTGAG
5851 TAGGTGTCCG TGGGGCTCTA GGCAGTTTAG ATGCAACAGA AGGGATTCTT
5901 CAGGAAAGTG AGAAGATTCT TCTGTTTCTC TCTCTGTCTC CCAAATTATA
5951 AGTGCCTTGA TGGTGCGACC AAATCTTATT CCTCATTGTT TTTATAGTCC
```

FIGURE 3B

```
6001 CTAGTACAGG GCCAGGCAGA TTCAATGCCT GTTGTTAAAT TAATGAATGA
6051 ATGCAGGGAC CAGTTGGCAG AGGGCATTGA GAGCCTGGCC AAGGAGGTGG
6101 AACATGAGCC TTAGCAATGG TAGGAGGGGT TTTGAGTAGG GTACTAATGA
6151 GGTTGGCTGG AAGAAGGGGT TAAGACTTGA AGCAGGGAGA CTAGTCAGGG
6201 GCTGCAGTAG TATCCTGGGC ATGAAGGAAC CTCTGAATGG CCCCTCACCC
6251 CCAGTGGTAC CAACACCAAC TTCCACACAG TCAGTTGTTC TACTTTCCCT
6301 CCAGAATGGG GAGTGGTTCA AGCCAATCAA CCTGGCAACT TCTGAAAGAA
6351 TCTTATGGGA CCTGTGCCAT GACCAGGTAG GGAGAAGATG TCATACATGG
6401 ACATCTATGT TCAGGGGACC TTTGAGGACC TTTCTGCATG GTGGCCAGGA
6451 GTGAGATGAT GTAAACCACA AATGGAAACT GAAGAGACTG CTCAGGAGTT
6501 GTTGGTTTTC TTTTCTTTTC TATTTTTTTT TTTTTGAGAC TAGGTTTCAC
6551 TCTGTCACCC AGTCTGGAGT GTGGTGGTGG CACAATCACG GCTCACTGCA
6601 GCCTCGATCT CCTAAACGCA ATCCTCCCAC CTCAGCCTCT CAAGTAGCTG
6651 GGACTACAGG TGCATGCCAC CACATTCAGC TAATGTTTGT ACGTTTTGTA
6701 GAGATGGGGT TTCACTATGT TGACCAGGCT GGTCTCGAAC TCCTGGACTC
6751 GTGATCCACC AGCCTCAGCC TTCCAAAATG CTGGGATTAT AGGCGTGAGC
6801 TACCTCACTC CCTCAGGAGT TGGTTTTCTC CCTCCCATCC TTAGTCTTCC
6851 CTGAGTAGAC CTGTCACCTA GTCCCTGGAC CTTTTGTTTT GAAAGCCACC
6901 CTCCAGGCTA CACTCCTTCT GGGTGAGGAG GAGGGTGATC TGGTTGGACA
6951 GGTTGGGCTG CTGTGGCTTC AGGGCACTTT CTCAGGCTGG GTTGCTGCTG
7001 CTATGTCACC TTTCTCAAGG AGTTCTGCTG GGACTGGCTT GGCTGCCTGT
7051 CTTGACTTTG CTTTTGACTG AGGAGGTGGG AGATGGTGAG GGAGGGGGTG
7101 GGGCTAGATC CAAGCCTGGA ATGGGGTGAC CTAACAGACA CTGGGGCCTG
7151 TGCTTAGACA CTAGGATCCT GGGGTTTGCA GGTTTCTAGA CTGAGAGGAG
7201 CTGGGGGCAA ATGCAGTGTG ACGTTGTGAG AGGGTCAGGG CTGGGTCTGT
7251 GTCAGCCTTC AGGCAGCCTG AGACCAGTCT CTACCTACTC TGTTCCCCTG
7301 GTACCTAGAA AGGAAGGGAA GGTGAGAAGC AATGAGCAGA ATGGAAAGAG
7351 CCCAGATTAA CATGCACATT TCCCATGGCC TTACTGGCCC TGTGACCTTC
7401 AGACACTTTG ATGACATCTT TGTGCTTCGT TTCTGCATCT GTAAATTGAA
7451 GATGGTAACA GAGTCTTTCT TAAAGGTTGT TGTGAAGATT ATAGAGCCTA
7501 GCGCATATAA AGCACTTGGC AGAGCCCTCG ATAAAATAAT AGCTGCTATC
7551 ATATTATCAT TATTATTATT TTATTTATTT ATTTATTTAT TTTTTTTTGA
7601 GACCGAGTAT CTCTCTGTCG CCCAGGCTGG AGTGCAGTGG CACAATCTCG
7651 GCTCACTGCA ACCTCCATCT CCCGGGTTTA AGTGATTCTC CTGCCTCAGC
7701 CTCCTAAGTA GCTGGGATTA CAGGCACCCA CCACCACACC CGGCTATTAT
7751 TATTATTCCT AGCTATAAGA ATGCTGTAGA GATGAATACA CTGTCAGTGA
7801 GCTAGGAGGT CATCCTGTGT ATCCATCACT TGTGCACTCA GTCGTTCAGG
7851 CGCTATTTGC TGAACACCAA CTACATGCCA GGTGCCATGC TAAGATTTGG
7901 GGACACAGTG GTGACCAAAA CAGACAGAAA CCAAGGAGCT GGCTTACATT
7951 CCAAGGGAGT GCATAGGAAG CTGTGTTTCA TTTCAGTTTC TGCTCTAGTA
8001 CCCCCCTTTC CCTGGCAGTG CCAGGGTCTG AGAAGGAAGA GTGAGGTGGT
8051 GAGGAGGTGT GAAGCAGTGG GGTGACCTGA GAGGAGAGGA TGGGGTGGCT
8101 TTGCCTCAAG GCTTGGGCCC CTGCTAGGTG TCGCTCTGCC TCAGGCCTCT
8151 GTTTCTCCTC CTGACACAGG CACAGACTCG GCCTCCCACC CCTTCCCCAA
8201 GGACATGACC TTGGGAAGGA ACATATCTGA AGCCCGCGGA GGGTTTCCGC
8251 TGCTGTGCAT CTGTGCCACA GATCCGCAGA TGCACCCACA GCTGGGAGCA
8301 CCGGTTCCTC CCGCCTACCT GCACTCCCTG GTTTCTGTTC CTTCCTCCTC
8351 CTCCTTCCTT CTCCCCGCTC CCCAGACAGG CTGGTGATGA GCTTTATAAC
8401 ATGAAAGCTG ATATTTGGCC ATTATCCTTC TACCCTGATT GCCAGCTCTT
8451 CTCAGAGTGC CTTCTTCTGT AATCCAATCT TTGCACCAGT TTCCCTGTGA
8501 AACTGCCAGT TTTCTGTATA GGCCTCTGCC CTCTCCTTGG CTCTTCTCTC
8551 TGGTCAGTGA GCTTTGTCAA GGGGAACACA GGGCTTCCTG GACACGTAAT
8601 TCCTCCCACT GAGGAGGAAG GGGCTAATCA CCAGCCCTGT TTTATTTTAT
8651 TTTATTTTTT TGAGATGAAG TCTAGCTCTG TCGCCCAGGC TGGAGTGCAA
8701 ATGGCTCGAT CTCGGCTCAC TGCAACTTCT GTCTCCCGGG TTCAAGCGAT
8751 TCTTCTGCCT CAGCCTCCTG AGTAGCTGGG GATTACAAGC ATGCACCACC
8801 ACACCTGGCT AATTTTTTGT GTTTTTAGTA GAGATGGGGT TTCACCATGT
8851 TGGCCAGGCT GGTCTCGAAC TTCTGACCTC AGCTGATCCA CCCACCTCGG
8901 CCTCCCAAAG TGCTGGGATT ACAGGAGTGA GCCACCATGG CTGGCCGACC
8951 CCATCTCTTA AAAAAACAAA AAGAAAAGAA AAGAAAACAA AACAAAAACA
```

FIGURE 3C

9001 CTTTTTAAAT TAACTGATTA TGGTGGCATG TGCCTGTAGT CCTAACTACT
9051 CAGGAGGCTG AAGTGGAAGG ATTGCTTGAG CCCAAGTAGT TGGAGGCCAC
9101 AGTGAGCTGT GATCACACCA CTGTACTCCA GCCTGGGTGA CAGAGTGAGA
9151 CCCTGTCTCA GGAAAAAAAA AAAATTACTG AGAACTCTGT GACCATGGCA
9201 CCATGAACTA TAGAAAGGGC TAACAGTTGG CTTTGAAATG TGGGTTATGG
9251 CTGGGTGCGG TGGCTCACGC CTGTAATCCC AGCACTTTGG GAGGCCAAGG
9301 TGGGCAGATC ACAAGGTCAG GAGTTTGAGA CCAGCCCGGC CAACATAGTG
9351 AAACCTCATC TCTACTAAAA ATACAAAAAA TTAGCCGGGT GTTGTGGCAG
9401 GTGCCTGTAA TCCTAGCTAC TCGGGAGGCT GAGGCAGGAG AATTGCTTGA
9451 ACCCAGGAGG TGGAGGTTGC CACAAGCTGA GATCGCACCA CTGCACTCCA
9501 GCCTGGGCGA CAGAGCAAGA CTCCATCTCA AAAACAAAAA TAAAAACAAA
9551 AAAAAGTGGT TTGTTTTCTT TTCTTTCTTT TTTCTTTTTT TTTTTTTTTT
9601 TTTTGAAACA GAGTCTTGCT CTGTCACCAG GCTGGATTGC AGTGGAGGAT
9651 CTCAGCACAC TGCCACCTCT GCCTCCCAGG TTCAAGTGAT TTCCCTGCCT
9701 CAGCCTCCAG AGTAGCTGGG ACTACAGGCA CGCACCACCA CGCTGGGCTA
9751 AGTTTTTGTA TTTTAGTACA GAAGGGGTTT CACCATGTTG GCCAGGATGG
9801 TCTCCATCTC CCTGACCTCG TGATCCGCCC ACCTCGGCCT CCCAAAGTGC
9851 TGGGATTACG GGCATGAGCC ACCACGCCCG GCCTAAAAGT GGGTTATTTT
9901 CTAATTGCTC TTCCCTGATT AAAATTTTCT CTTTGCCCAT CTTTTCTCTA
9951 GATATGTACT GACTTCATTC ATCCATTTAT TCGTCTCACT TGCTCATTCA
10001 TTTTTGCTTT CATTTACTCT ACTTTGTTGA ATAATATTTA GTGATCTACC
10051 TGCTGCCAGG CAGTGAGAGT CTGAAGTGAA CAGGATGCTG CTTTGCCCTC
10101 TGGGAGCTTA CAGTGTAGCT GGGAACCAGA CATCCAAACA AGCAGAATAT
10151 TATGCAAAAG AAATGTCAGG ATGCTTTGGA ATCACAGAGG AGTGAGAAAT
10201 CCCTCCCGGG GAGGCTGGTG AAGGCTTTGA AGAGGAAGTG ACATTTGAGT
10251 GGAGTCTTGA AGACTAGGCA GGATTCTCCA GGGGCCCTGG GTGTGGGGGA
10301 AGCACACATC CTCTTCCCTG TAGGAGGTGC TGTGGAGAAC ACCTCCAGTG
10351 GGGCTGCTAC TCTTCAGCCT TGCTGGGGCC AGCTGGAGTG GCCACACCAT
10401 GGTCACACCA GCTGAAGTTC AAGAAGCCCC TTGCCAGGAG ATTGCTTTGC
10451 TGGCTCTGGG TGAGGGCAGG TGCATCTGGA AGCCCCCTTC TTTCTAAGAT
10501 GTTTGCTCCT GAGTTTCTAT GTCCTAGTCT TTTCTTCCCT GAACCTTTTG
10551 CTACCAGTCA GCACAGCCCT GCCTGAGAAG GAGGCTGGAG GAGTGAGTGG
10601 TCAGTAGCCT GGTGGGTCTT GGCTGCCTCT GTGGTGCCCG CTGGCCTAAG
10651 TAGCAGGCTT AGGGAGGCGA GACCCAGTTC CAGGGGCTGC CAATGGGGAG
10701 CGAGATGGGG TGGCTGGAGC ACACTGCACA TGTCACCAAG GCTCTAGGGA
10751 GGTCTGTGCA CAAGGCAGTG GGAAAAGCAA GGGGAAGACC CAGCCTGGTC
10801 AACATGGTGA AACCCCGTCT CTACTAAAAA TACAAAAATT AGCTGGGTGT
10851 GGTAGAGCAC GCCTGTAGTC CCAGCTAACT TGGGAGCCTG AGGCAGGAGA
10901 ATCACTTTAA CACAGGAGGT GGAGGTTGCA GTGAGCCGAG ATCGTACCAC
10951 TGTACTCCAG CCTGGGTGAC AGAGTGAGAC CCTGTCTCAA AAAAAAAAAA
11001 AAAAAAAAAA AAAAAGTGGG GAAGGGGAAC ACTGATCCTG ATTATCTACT
11051 CCATATACTT ACTATGTACC TACTACCTAC ACAGGGACGG TGGGCTTTAC
11101 GCATGCCATT TATTCAGTGT ATAGAGATCT CAGCATCACA TAGGAGCAGG
11151 GAGTTCTGAA GTTGGCCTTG CTGGCATTTG AGAAGTTTCT TGGTGTATTC
11201 TTCAGGTTCA CGCCTCCAGA CAAGTGTAAG TGCTATTGAA TGCTGACTAT
11251 GTTCCAGGAA CTAAACCAGA TGCTAGAAGA CACGCAGTAA ACAGTACAGA
11301 TGCAGGTGCA CATGTGAGGG TCCACACAAG ACCTGAGAGA AGGGAGGGGT
11351 CTTGCTGCAG TTCCCCTTTT GTAACAAAGG AGAGAGTACT GTTGACCCTC
11401 TTCCTAGGAA CTGTGAGTTT GACTGAAATG TGTCCTGCCA CAGGATCTTT
11451 GCTGCTTCCT CTACCTGATT CTTTGGATCT CCCTGCTGGC ACCTTCTTGT
11501 CATTTAGGTC TCAGCTCAAA TGTTACCTCC TTTAAAATGT CTTCTCTGGC
11551 CAGCCAGTCT AAGGTTGCTT GTGCTTGGGG TCTCCTCACT CTCTACTTTA
11601 TCCCGCAGTT GCTTCTTATC ACATATGGCT CTCTGAAATT AGGTATTCAT
11651 TACTTACATC TGTCTTCCCC ACTAGAATTA AGCTCTGATG ACAAGGATCT
11701 TTCTGTGCTG TTCATAGCTT ATCTTCTAGT ACCTGGCTTA GTTCCTGGCA
11751 CATTGTAAGC ATTCAATAAC AGTTTGAATG AATGAATTAA CAAATGAAGG
11801 AATGAATGAA TGCATTTTCC TAGAGGACTT CTGTTCTTCC CTGAGGGAAG
11851 TTATAGGTCG TATTGGTTTC TTGGGACTGT TTTTTGTTTG TTTGTTTTGT
11901 TTTGTTTTTT GAGACAGAGT CTCACTGTAT CCCCCAGGCT GGAGTGCAGT
11951 GGCACAATCT TGGCTCACTG CAACTTCCGC CTCCCAGGTT CAAGCGATTC

FIGURE 3D

```
12001 TCATGCCTCA GCCTCCCGAG TAGCTGGGGA TTCCAGGAGC CTGCCACCAC
12051 GACCAGCTAA TTTTTGTATT TTTAGTAGAG ACAAGGTTTC ACCATGTTGG
12101 CCAGGCTGGT CTTGAACTCC TGACCTCAGG TGACCTGCCT GCCTCTGCCT
12151 CCCAAAGTGC TGGGATTACA GGCATGAGCC ACCACGCCCG GCCTGTTTTT
12201 TTTTTTTTTT TAAGACAGAG TCTTGCACTG TCTCCCAGAC TGGAGTGCAG
12251 TGGTGTGATC TCAGCTCATT GCAGCCTCAA CCTCCTGGCC TCAGGTCCAG
12301 GTGATCCTCT TACCTCAGTC TTCTGAGTAA CTGGGCCCAC TGGTATATAC
12351 CACCACACCT GGCTAATTTT TAAATTTTTT GCAGAGACAT GGTCTCACTA
12401 TGTTGCCCTG ACTGATCTTG AACTCCTTGG GTTCAAGTGA TCCTCACACC
12451 TTGGCTTCCC AAAGTGCTGG GTTTACAGGT GTGAGCCACC ATGCCTGGGC
12501 TTGAGACTGT TAAGATGATG AGGCTGGAGG GAGTGGATGG CCTCACTGCT
12551 TGAGCCCTAG AGATTCCTTA CTCCAGAGTG CCCTGGCTGC AGAGGTGGCC
12601 CTGGAGGGTC ACTCCAGCAA CCTGGCTGAG CTGATGGGCA TCATCTGATA
12651 CCAGCTCTGA CCCTGAATAA TAGGCAACAT GGACCTTAGT CTAAAGCACT
12701 GACCCCTCAT CTCTGCATAT ACCAAAGAAG ATGAGATTTG GGTGAGGACA
12751 CAGCCAAACC ATATCAGCTC CCGGGATCCC TGTGTGAATG GGGTCTTTTT
12801 TGGTGTTTGA GGGCTGCACA GGGTGACCTC TTTAGAGGTG ACCTCCTGCC
12851 ACAACCCACA GGAGGTGCAC ATGGCCCACA CATGCTGGTT TCCTGCAGTG
12901 GGAGGGGCTG GGGCACTCCT GGGACCTGTG CTTGGTAACT GGAGCTGGCC
12951 TGGCCCTGGG GATTGGGTGT CTGCCTTGGG TTTCAGGTGT ATTAGGTTGT
13001 TCCTCGTTGT GGAGTCTCAT TACTAATGAA AAGTTCAGGT CGCACTGCTG
13051 GTCCTTTGGG CTGTGGTTGA TCCTGGTGAT AACATTTGGC ACCCAGAGGC
13101 AGCCCTGTTT CCACTGAAGC ATGCGGAGCT TGGCTGGCAG GCAGGCAAGC
13151 TGGCAGCTGC CCTTAACCCA TGAGGTGCTG GCCCGCTAGT AGGCACACCC
13201 TACCTGTGCC AGAATTGAGG TTGTAGCCAG ACTCCAGGAG CCATCTGGGC
13251 CCCACAGGGG GCGGCATTTC CTCTTTTTGT TGAAACATTC CAGCCAAGTG
13301 CTGGCTTGGG CTTCATCTCT CTGTCCCACT CTCCTTCCTC TCCCCAACAT
13351 AAGCCTCCTT CTACATCCTA GAGCTCTTTC CATTCCCCCT CCTGCAGCTC
13401 TGGGCTCGCT AATCTCATGC TTCCCTAAGG GAGCTTGACG GCTGCTTCTG
13451 CTAACATTTA ATAAAGTTCT GCGTGCCAGA CCCTGTGTTA TGGGTTTTAC
13501 ACCTTATCTC ACAATCTTAA AAAAAAAATT CTCTGAGAAT CCTCTGTCAC
13551 CCCCACTTTA CAGGTGAGGA AACTGAGGCA AAGATAGGCT AACTGGCTTC
13601 CCCAACACCA TGCAGGTAAT TAGTGATAAA GGCAGGGTTG GAACCAAACT
13651 TGACCTCCCA ATTGTGCTCT TAATGGCCAG GACACTCTGT GTCTTGAGCC
13701 ACACTTCCTC CATGTTTTCT AGGGCTTTCT AGGGAGGCAG ACAGTGATGG
13751 GAAGGGGTGT TCTTTAGTGT GGATGTGCCC TGCCTGCTCC TTTCTGTAAG
13801 CGTCACAGCA CCTCCACTGC TGTACTGGGG AGGCACCAAG TTTTTCCCTG
13851 TTTGCCCACC CAAGGCGAGC TAGCTTAGGA GTCACGTGAG TGCTGGGTGT
13901 CTCGCCTGCT GCATCCCTCT ATCCTGCCCC TGCCCCCGGT GCCCAGAGGA
13951 GGGCCCTGCC TGTCTTCCCA GTTCTCCAAC AGCAGCGCTG TCCCAGCACC
14001 CTCGGGCTCC AGTTGTGGCC TGGCAGCTGC TGGGGCAGAC ACCATACAGA
14051 CAGAGTCACA GCAGGAAGAG GATGGGGCCC AGGGCTGCTG CCTCAGGCCA
14101 TGGCTGCATG GCACCATCAG TTGATTGAGG AGCTTTTCTT GCCAATGTCT
14151 GAGGCATCAG GTGGCAGGAC ACGTCTCCCT GCTCTTAAGC CTCAGGCATG
14201 CAGCCCTTCT TATGCTCTCT GGGGTGAGGG GGAGATCCCC CTCATGGAAT
14251 TGCTTTTTTT TTTTTTTTTT TTTTTTTGAG ACAGGGTCCT GCTCTGTCAC
14301 TCAGGCTGGA GTGCAGCCTC AACCTCCCAG ACTCAAGTGA TCCTCCTGCC
14351 TCAGCCTCCC GAGTAGCTGG GACCACAGGT GGACACCATC ACACCTGGGT
14401 TTTTTTGTTT TTTGTTTTTT GTTTTCTAGA GATGGGGTCT CACTTTCTTG
14451 CTCAGTCTGG TCTCGAACTC CTGGGCGCAA GCAGTCCTCC CACCTCGTCT
14501 TCCCAAAGTG TTTGGATTAC AGGTGTGAGC CACTGTGCTT GGCCTTTTTA
14551 TTTATTTAGA ATTTGTTTTG GAATTGCTTC TTTATGCCTG GCACTATGCT
14601 GGCACTATGT GGCAGAGATT TTAAAAACGA GCAAACAAAA CAAATGCTTT
14651 GTCAACCACA AAATGTATTC TCTGCCCCTT AGGTTCTTTT TGTGTAGTTG
14701 AGGCTAGAAG ACAAAAATAG GGGGCAGTAA GGAGCAGGGA GCGATGGTTT
14751 AGGAGGTCTT CCTTCCAGCC CCCTTGTTGA AGCATCTGGC TCACTAGCTT
14801 GGGGGAGCCA TTAGGCAGCA GTGGCCAATC CTGAGGCACT CTCAGGTGTC
14851 ACTAAGAAAA GGGGCATGTG CTCTATGGAT ACCCATGGGC TGAACTTGGA
14901 GTCTGGTCTG GACCCATGGC TGTGCTAGGA TCCACCGTCC CCAGCCCCAA
14951 CTGCAGTCAG CATGTTCATC ATCCTTAGGC CTCTCCGCTT CTTTCTGCAT
```

FIGURE 3E

```
15001 GTTTGTCTGC CTCATGCCCT GCTCATTACC AACTGGTCAG TCCCCACTGC
15051 CCTGCCTGGA GTGAGCTGGT TTGATTGGCT TAGCTAAGCT CCCTTGCCTC
15101 TGCTGGCCAG GTCACCCTGT GGGTCACCAG CAAACCTGTT GATGGTCCAG
15151 TCTGAACCTG CTTCTCCACA AAGAACATGT TGCACCCAGC CCTGCTTCTC
15201 TGAGCAGAGG TTTGGGGCTG AGCTGTTCTA GCCAGAAAGG GACACAGGGT
15251 GTGGCAGGCA CCATGATGGG CATATCTAAT GTGCCGGGAA AAACAATGAG
15301 CTGCTCTCCG TGCTTTGGGC ACCTGGTTGG GAGAGGGCCC ATCTGTCTGA
15351 CTTTCTCCTC CTGGGGCTCT CAGCGTCTCC GAGAACCTCT GCCAGAGCTG
15401 TGTAGAAGTG GTTTGCTTGT TTCTTAACAC TTCTGTGCCC TATTTCTTTC
15451 TGTACCCAAG AAAGGAAGTA GACTGTTTTG TAGGGACACT GTCGGGGTGA
15501 TGAATCTGGA CTTACTGGAA TCATGAACCA TGCCAAGGAG GAAGGAGAAA
15551 ATAGGCTATG GTGGGTGTCT TAGTTAGGGC TGGCTGCTGT AACAAAATGC
15601 CTTTAGCTGA GTAATTTAAA GCAAGAGAAA TGTATTGCTC AGAGTTTGGG
15651 AGGCTGGGAA GTCCAAGATC AGGGTGCCAG CAGATTCAGT GTCTGGTGAA
15701 GGCTGATGCT CTGTGACAAA GGTGGCACCT TCTAGCTCCA TCCTCACATG
15751 GCAGAAGAGG GAACAAGCTC CCTCAGACCT CTTTTCTAAG GGCGTTAGTC
15801 CCATGCATGA GGGCTCTAAC ATCACGACTG AGTCACCTCC CAAAGCCCTC
15851 ACCTCCCACC AGCACTGCAC TGGGGATTAA GTTTCAATAT GGGAATTTTG
15901 GAGGAACACA GACCTTCAGA CCACAGCAGC GGGCTTCTCC TCATGTGCCC
15951 CCTGCCTCAC TTCTAGATGC CGCATAATGT CAGTGAAACC CCGTCTCTAC
16001 TAAAAATACA AAAAATTAGC TGGGTGTGGT GGCACGTGCC TGTAATCCCA
16051 GCTACTTGGG AGGCTGAGGC AGGAGAATCG CTTGAACCCA GGAGGCAGAG
16101 GTTGCAGTGA CCTGAGATCG TGCCACTGCA CTCCAGCCTG GGCGACAGAG
16151 GAAGACTCCG TCAAGAAAAA AGAGAAAAGG CATCAGGTAT GCCAGGGTGT
16201 GCGGGAAAAG GCATCGGGTA TGCCAGGGCG TGTGGGAAAA GGCATCGGGT
16251 ATGCCAGGGT GTGTGGGAAA AGGCATCGGG TATGCCAGGG CATGTGGGAA
16301 AAGGTGGTAA GATTCCTCAG CCTCCCAGGG TTGGGAAGCC TCTGGCCGAG
16351 TGAAGCATAC CCTGGGTGGG TTTTAAGACA CCAGCTTTCC AGTCCAGCTC
16401 AGCTGTGGGA TGTGGGAACA TGAGTCAGTG GGAACATGAG AATTGGCTTC
16451 CCTGTGGCTC ACAATAATAC CTACTCCTGC CTACTTCATG GGACCCGCAT
16501 AAGAGCTGAG GGATTCCATA GCTCAGGGGT ATGCTGTAAA GACAAGCACT
16551 ATGCACCTGG GTGTGGTTCT GAAACTTTCT TGTGCAGAAG AGTGAGTAGG
16601 GCTGGGCGAG TCCTGAGAAT GTGCATTTCT CACACACCTC TGATGCTGCT
16651 GATGCTCTAG TCCCTTGGCT GGCAAGGGTA CCTGGTTAGT AGGGGCCAGG
16701 ACTCTGTAAT GCCTTCCACT TCAGGGTTCT CTGGGCTGGT TTTCCTGACT
16751 CCCCAGGAAG CCTTTATTCA GCAGAGGGAA GGTAGGAGTG AGAGGACTAC
16801 GCTGTCAGTG CTTCACATAC ATCGTTTAAT TTATCCCAGC ACAGCCCTTA
16851 GGAGGGAAGC AGTATTCTCC TTCTACACTT AAGAAAATCG GCCTGGTGCG
16901 GAGGCTCATG CCTATAATCC CAGCACTGTG GGAAGCTGAG GCGGGAGGAT
16951 CGCTGGAGCC CAGGAGTTCA AGACTAGTCT AGGCAATACA GGGAGACCTC
17001 ATCTCTACAA AAAAAAAAAA AATTAGCTGG GCATGGTGGT GCACACTTGC
17051 AGTCCCAGCT ACCTACCCAG AGGCTGAGCT GGGAGGATTG CTTGAGTCCT
17101 GGAGGATCGA GGCTGCAGTG AGCTATGATT GCTCCACTAC ACTCCATCCC
17151 TGGCAACAGA GTGAGACTCC ATCCCAAAAA AAAAAAAAAA TTGAAGCTAG
17201 GAGAAGTTGA GACTTGCCTG AAGTTACACA GTAAGTGCCA GAACCAGGAC
17251 TTGGACCAGG TCTTTCTGAC TCCAGGCCAA TGGATGTTTC TTCCATGACA
17301 TATATAGCTC TTGAAACTAC TTCTATCTAA TATCACCCAC AGTGCTGTTA
17351 AAAATACAGA TTTCTGGGCC TCACCCTCAA ATTATGATTC AGTAGGTCTA
17401 GGCACGTCAA GGTCATTGTT TTTGTCTTTG TTTTAAGTCA CCCCAGGTGA
17451 TTCTAAAGCC GAAGCTCTGC AAAGCACACC TTGAGAAACA GAGAACTCTT
17501 GTGCTCTCGC TCTCTTGACA CTTCAGGTGC AAAACTTTTG TCCTAATGTC
17551 GTTCTCAAAC TTACGCATGT GTGAGAATCA CTGTGAGAGC TTATTGAAAC
17601 TGATTGCGGG ACCCCATACC TAGAGGGCCT GATTCTATAG GTCTGAGGTA
17651 AGGCCCAAGA ATTTGCATAT TTGCATTTCG TTTTCTTTTC CTTTCTTTTC
17701 TTTTTTTTTT TTTTTGAGAT GAAGTCTCAC CCTGTCGCCC AGACTGGAGT
17751 GCAGTGGCAT GATCTCAGCT CACTGCAGCC TCTGCCTCCT GGGTTAAAGC
17801 GATTCTCCCC ACACCCCAGA CCCGCTCCTG AGTAGCTGGG ATTACAGGTG
17851 CCCGCCACCA TGACTAGCTA ACGTTTGTAT TTTTAGTAGA GACGGGGGTT
17901 TCACCATGTT GGCCAGGCTG GTCTCAAACT CCTGACCTCA GGTGATCCAC
17951 TCACCTCAGC CTCCCAAGGT CTTGGGATTA CTGGTGTGAG CCACCGCGTG
```

FIGURE 3F

```
18001 CGGCCAGAAT TTGCATTTCT AACAAGTCCC AGGTGATGCT GATGCTGTGG
18051 GTCCAGGGAC ACACTTTGAG AACAGCTTGT TACTCAGGCG ATATGTGGAC
18101 AGTAGCGTCA TCTTCACCTG GGAGCTTCCT GCAGCATCTC AGGCCTTGCC
18151 CTACACCTAC CAGATCAGAA TCTGCATTTT AACTCAATCC CCGCGTGATT
18201 CTCATGCACC TGGAAGTTTG AGAAATATGA CCTTAGAGGA GCCGGAATGT
18251 GAAACCACTG GAGGCAGAGA TAGATGGAGA ATATCTCTTC TTCTCACGGA
18301 TACTAAAGAT GCAACAAAAA GGGCTGACTC TCTGGGTGTG CACCCAGGTG
18351 GGGCTGATGA CCGAAAAGAG GCCAGATGTG GACAGAGGAC TCTTCCCTGA
18401 GGGAAGGCAG AGAGAACTTA GGAAAATCTG AAGAAAGGAG GTGGCTTCAG
18451 AGGAAAGGCA TTCATCTGGG CCATAAAACA GTGGAGAAGG TATCCTGCTG
18501 AGAGCACAGG GGTGGGGAGG GGGTGCCCTG GAGCTGAAGT CTTCAGTGGG
18551 GGGACAGTGA TAGGTGAACA CACATGTGAA TAAACAGTTT GCTAAGCAGC
18601 TGCGAGGGCT GGCCAAGGTG AGAAAGCATC CGTCTGCAGA GGCCTCAATA
18651 AGGCCAGTGT GTTGACTTTG TCCTGCAGTG CTCAGCAGTG GAAAAAACCA
18701 ACAGCCACGC AGGGAGAGGG AAGGAGCCAC GATGGGCACG GGTTACTGGG
18751 GCCAGGGCTT GACTGGTAGG TGGACACAGC TGAAGGCCCA GGTTGTGTGG
18801 GAACAGAGCG CAGAAGCAAT AGATTCCTCT TGAAGATCCT TGGGCTGTTA
18851 ACCTTTTTTA AATTTAAGAG AGGTTGTGTG GGCGGGGAGG GAGGAAGGAA
18901 AATCCTTCAG AAGACATAGA CTTACTCTGT TTCTTCCATC ATATGTGAAT
18951 GCATATGAAT AGCCAAAAGG TGAATAAAAC ACATGTTCCC AGGTGGCCAG
19001 TGAGACCTAG GTTGCAAGAT GGTGGGGTGT GTGTGAGGCC GGGGAGTGCT
19051 GCGAGCCCCG GAATTCCTCA GCCTTAGTCC CCCGCCACAT AGCTAAGAAG
19101 TGAGGGAGGA GGTGAGAAGG AGTCACTGCC CAGCCTCACT TCCGGTGGAG
19151 TACCCTGTCT CCTTGTCAGT TCTGTCTCTG GGGACAGTTG CCTGCTTTCA
19201 CCTCTCCCTC CATCCCCTCT TCTCTCACAG GGAAAAATTC ACCTTAATAT
19251 TGGAAGTTCC TCTCCTAGCA AAGTCCTTCT CAGGCACCCA CAGGCAAAAA
19301 GGAAACTAAG CAGAGTTAGG GCTTCCAGGC CTAGCCAACT ACACGACTCT
19351 CCTCTTGCTT CCCTAAGAAC CAGCGCAAGG GGCAGCGTGG GTTCCAGCAT
19401 AGATGGACCT GTGTTGGAAT CTCTGCACGT GCTGTGCTGA CCCTGGCTAG
19451 CCATTGACCT CTCTGAGCCC TTGTTTCCTT TCCACTAGGC TCTCTGAGGG
19501 CAGGGGCCAT GTCTTTTTCA CTGCTCTGTC TGCACTGAGC ACTGTGCAGG
19551 GCACATAGGA AGTTCCCATA AATGTTTGTG GGATAAAGGA AATAAAACCT
19601 TCTCTCTTCC TGTCCCCCTT GTGATGGCTT TGCACAAGGC ACTGTCCTTG
19651 GCCAGGTTTG CTAGGCTAGT GTGAGGATAA ACCAGGTATA TTACAAATTG
19701 GAGAAAATTT CTCGTTCTTC TTGGAAGAAG GTGCTGTATC ATGAAACAAG
19751 AATGTCTTGA TTCCCTTCTA TGCCAGGTAC TGGGGAGAAA CAGGTGCCTG
19801 ATAACCGTTG ATCCAGGCAG AAATAAGCAT ACTCCTGCTT CCCAAGGCCT
19851 GATGCTTCTC TCCTTCCTCC CTTCCTCCCT CCTTCTCTTC ACTCTTTCTC
19901 TGCACACATG GAAGAATGGC TGCCAGGCAT TGCCCATTTG GAAAAGTACA
19951 GCTCAATGGA TATGAATCAG CTTGGGCAGG CGAGAAATGA TTCACGTCTG
20001 ACCAAATCGA TTTAGTTCAG GTTGCCCGTT CTGCATCTTT TTTCCCTTGT
20051 AATTAAATGA TGATTGGTCT TGATGGTGGG AAGGAAGAGA CAGAATTTAA
20101 TTTGTTTGCC TTTGTAGAAA GCTGGGGACA GCACAGATAA GGGAAGATGT
20151 CTCCCATTTG GCAAATAACT GATGCGGAGG TGGAGTGGCA GTGGTGATGG
20201 GGATGCTGGT GCCTTCAGGC CTTCTGGGCC GGGCAGTGCA GCTGGTGGCA
20251 GACGGTTCGG AACTCTACCA TGTTCCCATC TGAAAACTGT GGCTGATCAT
20301 GCCCACTCCT GACCTTGCTC CAGGGAGTAC ACAAAGACGT AAGCTTAATT
20351 AACCCACCAG ACGTAGCTCT TGAATCCCTG GGCATAGTGC CTGGGTATAG
20401 TTAGAGTTGG GGAGAGGCAT GGTCAGCAAA ACAACCTCCC TCATCTCTCT
20451 GTTGTCACTC AGAGTCAAGC TGGCTGCTGC TGGTGGTGCT GACTTCTCTT
20501 GCTGCAGATT TCTCCAATAT GTTTCTGCCC TGCACGCATT TGCCAAATCC
20551 CTTCGGTTTC TTGTGTCTCG TGGCAGCTTA GCTCCTCCAG CCCTTGGATG
20601 AAGAAGCGTG GGAACTCTTT GCTTCCTTTC CCTCCCGCAG TGACATGCCA
20651 TGCCATGCCA CTGCCTCTTC ATCTGGTCCT ATGACAGTCA CTCATAAGCA
20701 CCCGCATGTA CCCGGCCCTG CACTAGCTCA TGACAGCTGC AGTCAATTGG
20751 GCCAGGTGCT GTATCTCATC CGGCCTCCTC AGCAACCCTC TGAGATACTG
20801 GTAATGTCCC TGATGAAGAT ATTTACTGAG GCAGAAATGG ACGCTCAGTG
20851 AAGCAAGGTG CCTGATGTTA TAGCAATGAG CTATGAGTGG CCAGAGGGAG
20901 GAGATAAGCT CAGGCCTGAC ACCAAAGCCC ATGCTCCTTC TAGTCAACCA
20951 CAGTGCCTCC TATGGTGAAT GAGTGAGTCA GCAACCAAGA CGCATGAGGC
```

FIGURE 3G

21001 CTTCTTTTTG GTGAGCCTTG GCTGGGTGCT GAGGCTTCAG GTACAATCAT
21051 GGGTTGGAAG AGCCCTCCTC TCTCTCCACA GTCTGGCACT ATGACCCCTT
21101 CTGGTTATTA ACAAGGCAAA GAGAGAGAGG GAAGAAAGCA GGCAAATAAT
21151 GTGGGTTGCT ATTCCTAGAG ATTAGAATTT CAGGAAGGAT AAACACAGCG
21201 TTCTCTCCAG AAGTATAAAT AGGAAGACTT CACACATGAC TAGAACGAGA
21251 CATGTTTTAA GTCTGTCGAG TAAGGCAGTG ATGAAGTAGA TTTCCCCAGA
21301 TTCACTCTCC CTCCTCTGGG TCCCCCAGGG CCTTTACTTG TGGCAACTTT
21351 CAGCTCAGGG AGGGAGGAAA GCCCCTTTCA AAGCTTCAGA TACTTCCTTA
21401 AGGTCAGTTT CTGCTTAAAG AAGGCCTTTA CATTACTTCA TCCCTTTGCC
21451 AAATTAAACT GAAAGGAAAC CTTTCAAGTG TGATTGCCTG GCCCTTTCCT
21501 GTTCATTTCT CGTGGGTACG CTTTCTAACT TTCTTTCTTT CTTCCTTTCT
21551 TCAGGTGTTG ACTTTAAGAT GAAGACCATA GAGGTAGACG GCATCAAAGT
21601 GCGGATACAG ATCTGGTGAG CTGGGGAGGA GGAGGAGGCA GATGTAGGAG
21651 AAGAGGACTT CTGGCTGCTC CTTAGCTGCC CCTGCCATGT GTAAAATTCC
21701 TAGGCTTCAC CTGGGATAAC TGGCCACCTC TCTGATGGAT GGAAGCGAAG
21751 TCTCAGAAGC CCATCTCTTC CTATAAGCCT TAATCTCCAA CCTCTAAGAA
21801 ACTTTAGGGG ATTGACTACA AGCACCAAAG GGCAGGAATT AGAAGGAACT
21851 GGCACACTAA CCATTGTGAA TTTATCTCAG GATTAGGCTT TGCCCTTGGG
21901 CTGTGCCACA CTATGTTAAG ATTGGAAGGA AGGAGGCTAC ACCCCCCATC
21951 ATTTAGGGCG AGACCCTGAG AGAGTTCCTC AGGATAGCAT GATGAAGTTT
22001 CCACAGTAGC AGAGGGTGCT GCTGTGGCTC TCTGCCTGAG GTCTTGGAAG
22051 CACTGCCTTT GCCAGGGTTT AGAGCTCCCT CTCAATTCCA CAGCAGTATG
22101 GGCACTGCCT TCAGAGGTCC CATAGGGACT AGGGGTGTAG CAGCATCCCC
22151 TGCCAACTCC CATCCAACCA AATCTGGCCA CAGTGGCCAG ATTCCAGAGA
22201 GCTGTCCAAG GCCTGTTCTG GCTGTGGCTT CTGGTTTCTG CCAGGAGGGC
22251 AGTTGGCAGG AGGGGCCAAG GCCCTGCAGG CCTGGTCAGC ACCAGCACAG
22301 ATGACCAGGC CTCTGACTGC AGATCCCTGT GGGGATCCAA GCATCCCTGG
22351 TTTTTCACCC TTTAGCTCCC CAGTTTTTCC TACAAGGGGA CAGCTCTGCT
22401 CTTCCCCTCC CCGTCTGTTC CCATGGTCCC TGCTCCTCTG AGGGACTGGC
22451 TTTCTCCTGC AGGGACACTG CAGGGCAGGA GAGATACCAG ACCATCACAA
22501 AGCAGTACTA TCGGCGGGCC CAGGTAAGCC ACCACATTGG GGGTTTCAAA
22551 GTGGGAAGCT GCCACCCACA CTCCCAGCTC TGGGTATTTG AGATGTCTGT
22601 GCCACGGATC CCCTAAATAC AGTTCGCCTG CTTGGAGGAG CGCAGGGCGT
22651 CTTTCAGCTG TTCACTGATC ATTTGTCCGT CCATTGTTCA TGGCCCACTC
22701 ACTGCAGGCA GGCCCCTGCC CTCACCCCTG ACTTCCACCC TCCATCCTGG
22751 GTCAAAGATC CAGGTCAAAG CATGTGGTGT CTTCCTGCTG TAGAGAGTTC
22801 TGTGATGGGC CTGGGAGGCG GCAGTGGTGG GGTCTGAGAG AAGAGATATT
22851 TCTGGATGCT GAGCAGGGAG AATGGGAGAG TGGGACCCAA CCTTTAAGTT
22901 TCCACGGCCC CTTCTGGCCC CATGACTGCA CTCTCTCTGT GCATATCACA
22951 TCTCTCTATT TCTCTCTCTC TCAGGGGATA TTTTTGGTCT ATGACATTAG
23001 CAGCGAGCGC TCTTACCAGC ACATCATGAA GTGGGTCAGT GACGTGGATG
23051 AGGTAGGAGA TGCCACCTCA CTGCCGGGGT GTGGAGAGGG TGCCTCACCG
23101 GGGAAGGCAA GGCGAGGGCC AGATGGGAAG GCAAATGCTT CCAGGAAGCT
23151 TTGCCTTCCA CAGCCCTGGA TGAAGACCTC TGGGTGAGTA AGACATGGGG
23201 AAGAAACCGA AGCTGCCATG CCCTCACTCT CTATACCCTG CCAGGCCTCC
23251 ACGGCTGTGT CTTTCCCGGA AATGAATTAG TTCCAAGTCT TCCCTGTGAG
23301 CAGCTTCTTT CCTGAAATCT TGGGACCAGG TGGAGTTGCA AGATTGGGAT
23351 CTAGTCCTGG CTCTGCACAA TAGCTGTGGA GCCTTGGGAA GCCATTTGAA
23401 TCCTCTGGGT CCCCAGTTCC TGTAGAATGA GGGCTGGACT TACATCCAAT
23451 GTCCTTTCCA GCTCTGATAC CAGTGGTCTA ACCCAAGGAA GCACCAGTCT
23501 TAGCCAGAGT GTCTTCTACC CTAAGCTCTC CCCGTGATAC CCTTGAGGTC
23551 AGCCATGGCA CTTGGGGGAG CCTGGCACCT GCATCCAGTC GGCCCACCCT
23601 GTCCCTAGGG CTCTGGAATT GGTGGTGGGC TGGAGGCAGT GCAGACTCTG
23651 TAGGGAAAAT TGGGGGGGCA GGCAGCACTC ACTGGCTGTT CTGCCCATCC
23701 TTTGTCCCTA GTACGCACCA GAAGGCGTCC AGAAGATCCT TATTGGGAAT
23751 AAGGCTGATG AGGAGCAGAA ACGGCAGGTG GGAAGAGAGC AAGGGCAGCA
23801 GGTAAGTGGA GGGAAAAGGC AAGTCCACCC CAGGTCCTCT GCTGGGCCTC
23851 CAGGGCCAGT CCTGAGCGTG GGGACCTAGG GGTGTGTTCC CCAGTGGCAG
23901 GTCCTCCCAC ACGTCCCCAG CACCCCAAGG CCCTGGGGGA GTGGCCATCC
23951 TCGGAAGGCT TGTTGTCTGG GTTTCAGGAC AGAAGCCCAG AGATTCGGGG

FIGURE 3H

24001 TCCATCCAGA AACAAAGACG TCATAGGCAG CAACTCTCCC AAGTCCAGGT
24051 CCCCAAATGC AGGATTGCCC TCTGCTTAAG AGATCATCCC CGTGTTAGTA
24101 ATGAAGGACT TCAAGTTGTC AACCTCTTCT CTGACAGCAT CCAGGCCTAG
24151 CTGCCATGTT ACGGTCGAGA AATGATCTCC CATCCCACCC AACACTCCCC
24201 CACTCCTGTC CTTCTTACCC AGGAAAGAGC CAGGGAGGCA AATGAGGAGA
24251 CAAAGAGCCA CAGCTGGAGA AGCCATGGGG GCAGAAAGGG TAGGAGGATG
24301 ACGCTGAGGG AATGTCCAAG CATGCAGGGA GACCATCCTC CCAGAGAGCA
24351 GAAAGAAATA TTGGTTATTT TTTTTTTCTT TCTTTCTTTT TTTTTTTTTT
24401 TTTGAGATGG AGTCTCGCTC TGTCACCCAG GCTAGAGTGC AGTGGCGCCA
24451 TCTCGGCTCA CTGCAACCTC TGCCTCCTGA GTTCAAGCAA TTCTTCTGCC
24501 TCAGCCTCCC AAGTAGCTGA GATTACAGGT GCATGCCACC ACGCCTGGCT
24551 AATTTTTTTG TATTTTTAGT AGAGATGGGG TTTTGCCATA TTGGCCAGGC
24601 CGGTCTCGAA CTCCTAACCT CAGGTGATCC ACCTGCCTCA GTCTCCCAAA
24651 GTGCTGGGAT TACAGGCGTG AGCCACTGTG CCCAGCCAAG ATTGGTATTT
24701 CTGAGATAAG TTATCCACTC AGTCCGTGGA CCTCAAGAGT TTTCCTCTCC
24751 CTTTTCAGTC AATAGCGTTC CATTAGTACT TAAAATGAAA TTGATTGTTT
24801 GGTATAAAAT ATAAGACATG GTCATTGACC AATTTGAAAG TAGAGGCAAA
24851 GCCTACTAGG ATAGTATTTA TTGAGCACTC TATGTGTGGC ACTGTGCTAA
24901 GGCAAGCGCT TTTAAGTGCA CGACCCCACT GAATCATCCC ACAACCATGG
24951 ATGGGAGACA CACTCAGTCT CCTTTAACAG AAGATAAAGC TGGGGCTTAC
25001 AGAGAATGTA CAACTTGTCC AAGGTCACAC AGCTAGCCAT CAGTGGCAGT
25051 GCTGCTATTC AGGTCTGGGA CTGTGGGACT CCAGAGCCCA TGTTTTTTAC
25101 GAGGATGCCA TACTGCCACA ATGGATGGTG TCTTTATCTC CTGATATATG
25151 ATTGTGTGTT GGGAGGCGTG GGGTGGCAGC TGGAAGAATG GAGAGGCATA
25201 TTTGTGGAGG ATCTTCCCCC ATTCTCTGCT ACCCTCTCTT GGAGCTCCCA
25251 GTCCCATCTG AGAAATTATC TACTCTGAGA AATCGTCACA ACACAGCATG
25301 GTTGTGAGTG CAGTGGCAGA AGCCTGTGCC TGGTTGTATG GGCCCCTCCC
25351 CTGCCTTACT GACTCTCTTT CAGAAATGTC CTTCTCTTGC AGCTGGCGAA
25401 GGAGTATGGC ATGGACTTCT ATGAAACAAG TGCCTGCACC AACCTCAACA
25451 TTAAAGAGGT GAGAGCCCTG GTGACCAGGC GCCCGCTCTC TCGGGCTGAG
25501 TCCAGCAGAG GTGGGAGGAG GAGCCATAAG ATGGACCTTA TCCCTCAGGC
25551 CGCTGCAGGG TTGCCAGGGG AGAGGAGGAG ACACTGGACT AACCTGTGCC
25601 CTTTGGTTTC CAGTCATTCA CGCGTCTGAC AGAGCTGGTG CTGCAGGCCC
25651 ATAGGAAGGA GCTGGAAGGC CTCCGGATGC GTGCCAGCAA TGAGTTGGCA
25701 CTGGCAGAGC TGGAGGAGGA GGAGGGCAAA CCCGAGGGCC CAGCGAACTC
25751 TTCGAAAACC TGCTGGTGCT GAGTCCTGTG TGGGGCACCC CACACGACAC
25801 CCCTCTTCCC TCAGGAGGCC CGTGGGCAGA CAGGGGAGCC GGGGCTTTGC
25851 CCTGCTGCTG TCCTCTCGTG TGATGACCCT ATTGAGTATC AGTAGCCACT
25901 ACTCCCCCTG CCTGGCCCTG AGAGCGGCTC TGCTGTCATC TCAAGCAGCC
25951 CCTGTCCCCA GCCCGTCCAC CCTGGAGTGG TCTTCTTCAG CCTGTTTCCC
26001 CAGCCACAGG CCTGCTACGA CCCCCACGAT GTGCCGCAAG CACTGTCTCA
26051 CCATCCCGCA CCCACCAGAC AACAGCCAGG GCTGGAGTCC AGGCCACTTT
26101 CAGCTGCTCC TTTCTCCGTG CATCGTGTCT CTTCTCTGCT TTTTCTCTCT
26151 TCCCCCACTT CTCTTTCTCT GACCCCTCCC CTCCGGTGCG TTTCGTATCA
26201 AAGCTCCTCA AACCCCGTCC CCCGTGTGTC CTGCTGTGTG CAGCTCGCTC
26251 TTTCCTTCCT TCCTAAGCTA TCCAAGGGGA TGGACCCAGG CTCGTGGGGA
26301 GGTTCCACCC TTGGATCCAG GAAGAACCCT CCACCCTGCC TCGTGGGTGG
26351 GCCAAAGGCT ACAGGGTGCT TCTTCCTCTT CCCCCACCCC CACTGTCCCT
26401 CATGTGCCAT GGGCCTGCCT CCCCAGTGAC CTGCGAAAGT GGAGCATCGA
26451 GGTAGGAGGG AAACGGCAAC CAGGGAGTCC TCGAGCCTGG GGCTGCCCTA
26501 CCTCTACCCA TTCCCCGACC AGAGCTTTGC CCTTGCTTGG CTGCCCGCCT
26551 GCCTCTTTGG GGAACTGAGC TCAGAGGCAG GTGCTTCAGA GAAGGAAACA
26601 AAATGAGGGG TGGCAGGGAT AAAAAGTCAC CTCCATTCTC TACCTCCCAT
26651 GCAGCATGAA CACAATTTCT CTCCACCTGG CTCCCAAATT TAAAGATGTG
26701 GACCAAGGCC TGTGGGTACT CCAGGGGCAA GGAGAGCCCT GGGGTCAGTG
26751 ACACTGTCAG GCCAACCATG CACTCCACAA AGGGGAGCAT TTGGAAATGA
26801 AGGACTAGCT CCTATGTATC AGGTTAAGAG CAAGGGAGAG CTGGCCAGGG
26851 ACAGCAGTTT GCACAGCAGA GGGGAATGTA GCAACAGCAG GGCCTCCTAG
26901 GCCCCATCTT CCATTTCTTA GGTAAGAAGA GCATTTCCTC AGACTCCCAG
26951 GCGGAGGACT GAGCCTAGCC TTCAGCAACC AAGGTTCTCC TGGGACCCAA

FIGURE 3I

```
27001 AGTTTATGGG AGAAGGGCAA AGACTTCATG GGAAGAGAGA AGGAAGGCCC
27051 TGGGTAGAAA CGCTTGGTGC TGTTCTCTTT GGCCTTTAAG ACAAAGCGCT
27101 CATCTTGCCC TCTACCTCCT GATAGGCTTG AGGGTTTGCC AACCACACTG
27151 TGGCTACAGG TGGAGGGAAG AGGACTCCTT CCTCCAGAGT GCTATGTTCA
27201 GGAAGTTTCT TTAACCCCAT ATGGCCCAAG AGTAGCTCGT AGGAGGCCCT
27251 TTAAAGACGG AACAAGTAAT TTACCAGTTC TACTGGGGTT CCTGCCCACC
27301 GTCCCAAGGT GGGCGAGGCC TAGGAAGAGG GTCATTCTTA AGCCACACAT
27351 TAGCTGCACT GCGTGGCTGC AGCCAAAACA AAGAACTGGG TGTTGAGTAT
27401 TCATCAACTA AGAACCAAAA TCCAGGGCAC TCATATGTGA AGGATAAGAA
27451 CCTCACTTCC TTACTCCTCC AAAAAGAAGT GGGGAAAGAA CCATCAAACC
27501 TTTCCTCCTG ACTTACCAAA CCAGGAAAAC AGCAGGAGAG GGTGGCTCAG
27551 GACTTAGGGA CAGGGTATAG CTTAGATGGT GGAAAGCAAA GGAGAGCAGG
27601 AAGTTGTAAA TCACTGGCTA ATGAGAAAAG GAGACAGCTA ACTCTAGGAT
27651 GAAGCTGTGA CTAGGCTGGA GTTGCTTCCT TGAAGATGGG ACTCCTTGGG
27701 TATCAAGACC TATGCCACAT CACACTGGGG CTAGGGAAGT AGGTGATGCC
27751 AGCCCTCAAG TCTGTCTTCA GCCAGGGACT TGAGAAGTTA TATTGGGCAG
27801 TGGCTCCAAT CTGTGGACCA GTATTTCAGC TTTCCCTGAA GATCAGGCAG
27851 GGTGCCATTC ATTGTCTTTC TCTCCTAGCC CCCTCAGGAA AGAAGGACTA
27901 TATTTGTACT GTACCCTAGG GGTTCTGGAA GGGAAAACAT GGAATCAGGA
27951 TTCTATAGAC TGATAGGCCC TATCCACAAG GGCCATGACT GGGAAAAGGT
28001 ATGGGAGCAG AAGGAGAATT GGGATTTTAG GGTGCAGCTA CGCTCACCCT
28051 AAACTTTTGG TGGCCTGGGG CATGTCTTGA GGCCCAGACT GTTAACCAGG
28101 CTCTGCTGGC CTGTTTACTC GTCACCACCT CTGCACCTGC TGTCTTGAGA
28151 CTCCATCCAG CCCCAGGCAC GCCACCTGCT CCTGAGCCTC CACTATCTCC
28201 CTGTGACGGG TGAACTTCGT GTACTGTGTC TCGGGTCCAT ATATGAATTG
28251 TGAGCAGGGT TCATCTATTT TAAACACAGA TGTTTACAAA ATAAAGATTA
28301 TTTCAAACCA CCGGTGTGGC TGCCTGGATG AGTCCTTGGG GGTAGGTCTC
28351 ACTCAGACCC TGGCAGTGAT GTGGGAGGGA GAGAGGCAGT GCTGGTAGAA
28401 GCAGCTCCAG AAGCAAAGGC AACAGCAGTA GAGTGACCAC GGAAGCGGCA
28451 AACATTGTCT TCCCTTCTCT ACCTTCCCTA GTGCCACCTG CAGGGAGGCC
28501 CAAAGCAAAG CCCCGTTGCC CTGCATTGGG CTGGCACTGC AGAAATAAGA
28551 TGAAACACAG TTATCGAGAG GATGCTGAAC ATCTATGAGC AGGTTTTAAA
28601 GCCAAGATGA GTCTCATCTG TTTGTGTGGG TCAGGAACGG GTCTTCCTGA
28651 AGGCATGAGG TGGGACTGGA TAATCTTTCA GATTTGTGAT TGGATACCTC
28701 GGGGGAGCAG AGGCAGACTG GGATCTCAGG ACTGCAGGTA TTTCATACTT
28751 TGGGATATGG AATTGATGGA  (SEQ ID NO:3)
```

FEATURES:

| | |
|---|---|
| Start: | 2044 |
| Exon: | 2044-2167 |
| Intron: | 2168-21554 |
| Exon: | 21555-21615 |
| Intron: | 21616-22462 |
| Exon: | 22463-22523 |
| Intron: | 22524-22974 |
| Exon: | 22975-23052 |
| Intron: | 23053-23711 |
| Exon: | 23712-23801 |
| Intron: | 23802-25392 |
| Exon: | 25393-25458 |
| Intron: | 25459-25613 |
| Exon: | 25614-25769 |
| Stop: | 25770 |

CHROMOSOME MAP POSITION:

Chromosome 14

FIGURE 3J

ALLELIC VARIANTS (SNPs):

| DNA Position | Major | Minor | Domain |
|---|---|---|---|
| 206 | - | T | Beyond ORF(5') |
| 4963 | C | T | Intron |
| 8175 | G | A | Intron |
| 10515 | T | C | Intron |
| 13034 | T | C | Intron |
| 13781 | T | C | Intron |
| 14050 | A | C | Intron |
| 14273 | - | T | Intron |
| 17582 | T | C | Intron |
| 17700 | C | T | Intron |
| 18074 | T | C A | Intron |
| 19328 | G | T | Intron |
| 19570 | A | G | Intron |
| 20892 | C | T | Intron |
| 26465 | G | A | Beyond ORF(3') |
| 26472 | A | G | Beyond ORF(3') |
| 28071 | C | T | Beyond ORF(3') |
| 28096 | C | G | Beyond ORF(3') |
| 28403 | A | G | Beyond ORF(3') |
| 28467 | C | G | Beyond ORF(3') |

Context:

DNA
Position

206
GCTCAAGATTGCACAGCTGGTGAGTGGTGACACTGGGACTGGAACCCAAGTGTGCCTTAC
TCCAGAGCCCTTGGCATGCACCTGAAACCCCATGTAAGCCCACTGTGGAGACGCGCACCT
CGAAATAATGGAATCCACTACATCAGTTCCTTTAGCTTTCTGTGTAATCAGAGTAGCTAG
CAGGCTCGGGATTTCGCCCCCCGGC
[-,T]
TTTTTTTTTTTTTTTTTTTTGAGACAGAGTTTTGCTCTTGTTGCCCAGGCTGGAGTGCAAT
GGCGCAATCTCGGCTCACCGCAACCTTCGCCTCTCAGGTTCAAGCAATTCTCCTGCCTCA
GCCTCCCGAGTAGCTGGGATTACAGGCACCGGCCACCACGCCCAGCTAATTTTTTTATAT
TTTTAGTAGAGATGGGGTTTCACCATGTTGGCCAGGCTGGTCTTGAACTTTTCCCCTCTT
ATTATAATTCAGACACTTAACCTGAAATATACCTTTTCAAATGAAGTAAATGGGCTTACC (SEQ ID NO:14)

4963
TATTAAGGGACTTGGGATTCTCCCTTATCTTGGGCGTGTTTTTCAGCATTAACTAAAACT
TAAAGGAAAGAGTTGGATGGTCAAGAAAAGCTTTTTCCTTAAGTGATATGGACAGTTTCT
CAAGGAGGTAGAAGGGGCAGCCAGGAGACAAATCAAGGAGCCAACGAAATGAGTGCTACC
AAGTCATAGTCATTCGCTTATTTTTAAAAAATGCGTGTCCTGTATGCCAGGCTCTGCACT
GAGACCGAGAGATTCCAAGATGAATAATACCTACAGTCACTGTTCTCAAATTGTGCATTA
[C,T]
CTAAAACACATTACATGACCATGCTGGCCACTGATCGAGGCACCTTTCCCAGGGGCTTTT
TTTGTGAATTAAGAAAACAAGGTAATTCACCAGTTATTGCCAAGATAGTTTGGCTTCTTG
GCTCATGTGGATATCACCTAGGCCAGTACTTTTGTGATTTACTGTGTACTCCACTTTAAC
GGCCTGCGATCTTCTAGAGAAGAACCCGCCAGGGAGCAGTGAGAGGCCTCCCTGGTAGAC
TGAGACACTGACTGTCCCTCCCCCTATCCTTTTCGTCTTTCTGGCCAGCAGACCAGCAGG (SEQ ID NO:15)

8175
ATGCCAGGTGCCATGCTAAGATTTGGGGACACAGTGGTGACCAAAACAGACAGAAACCAA

FIGURE 3K

GGAGCTGGCTTACATTCCAAGGGAGTGCATAGGAAGCTGTGTTTCATTTCAGTTTCTGCT
CTAGTACCCCCCTTTCCCTGGCAGTGCCAGGGTCTGAGAAGGAAGAGTGAGGTGGTGAGG
AGGTGTGAAGCAGTGGGGTGACCTGAGAGGAGAGGATGGGGTGGCTTTGCCTCAAGGCTT
GGGCCCCTGCTAGGTGTCGCTCTGCCTCAGGCCTCTGTTTCTCCTCCTGACACAGGCACA
[G,A]
ACTCGGCCTCCCACCCCTTCCCCAAGGACATGACCTTGGGAAGGAACATATCTGAAGCCC
GCGGAGGGTTTCCGCTGCTGTGCATCTGTGCCACAGATCCGCAGATGCACCCACAGCTGG
GAGCACCGGTTCCTCCCGCCTACCTGCACTCCCTGGTTTCTGTTCCTTCCTCCTCCTCCT
TCCTTCTCCCCGCTCCCCAGACAGGCTGGTGATGAGCTTTATAACATGAAAGCTGATATT
TGGCCATTATCCTTCTACCCTGATTGCCAGCTCTTCTCAGAGTGCCTTCTTCTGTAATCC (SEQ ID NO:16)

10515 CTGGTGAAGGCTTTGAAGAGGAAGTGACATTTGAGTGGAGTCTTGAAGACTAGGCAGGAT
TCTCCAGGGGCCCTGGGTGTGGGGAAGCACACATCCTCTTCCCTGTAGGAGGTGCTGTG
GAGAACACCTCCAGTGGGGCTGCTACTCTTCAGCCTTGCTGGGGCCAGCTGGAGTGGCCA
CACCATGGTCACACCAGCTGAAGTTCAAGAAGCCCCTTGCCAGGAGATTGCTTTGCTGGC
TCTGGGTGAGGGCAGGTGCATCTGGAAGCCCCCTTCTTTCTAAGATGTTTGCTCCTGAGT
[T,C]
TCTATGTCCTAGTCTTTTCTTCCCTGAACCTTTTGCTACCAGTCAGCACAGCCCTGCCTG
AGAAGGAGGCTGGAGGAGTGAGTGGTCAGTAGCCTGGTGGGTCTTGGCTGCCTCTGTGGT
GCCCGCTGGCCTAAGTAGCAGGCTTAGGGAGGCGAGACCCAGTTCCAGGGGCTGCCAATG
GGGAGCGAGATGGGGTGGCTGGAGCACACTGCACATGTCACCAAGGCTCTAGGGAGGTCT
GTGCACAAGGCAGTGGGAAAAGCAAGGGGAAGACCCAGCCTGGTCAACATGGTGAAACCC (SEQ ID NO:17)

13034 AGATTTGGGTGAGGACACAGCCAAACCATATCAGCTCCCGGGATCCCTGTGTGAATGGGG
TCTTTTTTGGTGTTTGAGGGCTGCACAGGGTGACCTCTTTAGAGGTGACCTCCTGCCACA
ACCCACAGGAGGTGCACATGGCCCACACATGCTGGTTTCCTGCAGTGGGAGGGGCTGGGG
CACTCCTGGGACCTGTGCTTGGTAACTGGAGCTGGCCTGGCCCTGGGGATTGGGTGTCTG
CCTTGGGTTTCAGGTGTATTAGGTTGTTCCTCGTTGTGGAGTCTCATTACTAATGAAAAG
[T,C]
TCAGGTCGCACTGCTGGTCCTTTGGGCTGTGGTTGATCCTGGTGATAACATTTGGCACCC
AGAGGCAGCCCTGTTTCCACTGAAGCATGCGGAGCTTGGCTGGCAGGCAGGCAAGCTGGC
AGCTGCCCTTAACCCATGAGGTGCTGGCCCGCTAGTAGGCACACCCTACCTGTGCCAGAA
TTGAGGTTGTAGCCAGACTCCAGGAGCCATCTGGGCCCCACAGGGGGCGGCATTTCCTCT
TTTTGTTGAAACATTCCAGCCAAGTGCTGGCTTGGGCTTCATCTCTCTGTCCCACTCTCC (SEQ ID NO:18)

13781 CCCTGTGTTATGGGTTTTACACCTTATCTCACAATCTTAAAAAAAAAATTCTCTGAGAAT
CCTCTGTCACCCCCACTTTACAGGTGAGGAAACTGAGGCAAAGATAGGCTAACTGGCTTC
CCCAACACCATGCAGGTAATTAGTGATAAAGGCAGGGTTGGAACCAAACTTGACCTCCCA
ATTGTGCTCTTAATGGCCAGGACACTCTGTGTCTTGAGCCACACTTCCTCCATGTTTTCT
AGGGCTTTCTAGGGAGGCAGACAGTGATGGGAAGGGGTGTTCTTTAGTGTGGATGTGCCC
[T,C]
GCCTGCTCCTTTCTGTAAGCGTCACAGCACCTCCACTGCTGTACTGGGGAGGCACCAAGT
TTTTCCCTGTTTGCCCACCCAAGGCGAGCTAGCTTAGGAGTCACGTGAGTGCTGGGTGTC
TCGCCTGCTGCATCCCTCTATCCTGCCCCTGCCCCCGGTGCCCAGAGGAGGGCCCTGCCT
GTCTTCCCAGTTCTCCAACAGCAGCGCTGTCCCAGCACCCTCGGGCTCCAGTTGTGGCCT
GGCAGCTGCTGGGGCAGACACCATACAGACAGAGTCACAGCAGGAAGAGGATGGGGCCCA (SEQ ID NO:19)

14050 GGAAGGGGTGTTCTTTAGTGTGGATGTGCCCTGCCTGCTCCTTTCTGTAAGCGTCACAGC
ACCTCCACTGCTGTACTGGGGAGGCACCAAGTTTTTCCCTGTTTGCCCACCCAAGGCGAG
CTAGCTTAGGAGTCACGTGAGTGCTGGGTGTCTCGCCTGCTGCATCCCTCTATCCTGCCC
CTGCCCCCGGTGCCCAGAGGAGGGCCCTGCCTGTCTTCCCAGTTCTCCAACAGCAGCGCT
GTCCCAGCACCCTCGGGCTCCAGTTGTGGCCTGGCAGCTGCTGGGGCAGACACCATACAG
[A,C]
CAGAGTCACAGCAGGAAGAGGATGGGGCCCAGGGCTGCTGCCTCAGGCCATGGCTGCATG
GCACCATCAGTTGATTGAGGAGCTTTTCTTGCCAATGTCTGAGGCATCAGGTGGCAGGAC
ACGTCTCCCTGCTCTTAAGCCTCAGGCATGCAGCCCTTCTTATGCTCTCTGGGGTGAGGG

FIGURE 3L

GGAGATCCCCCTCATGGAATTGCTTTTTTTTTTTTTTTTTTTTTTTTGAGACAGGGTCCT
GCTCTGTCACTCAGGCTGGAGTGCAGCCTCAACCTCCCAGACTCAAGTGATCCTCCTGCC (SEQ ID NO:20)

14273 TCTCCAACAGCAGCGCTGTCCCAGCACCCTCGGGCTCCAGTTGTGGCCTGGCAGCTGCTG
GGGCAGACACCATACAGACAGAGTCACAGCAGGAAGAGGATGGGGCCCAGGGCTGCTGCC
TCAGGCCATGGCTGCATGGCACCATCAGTTGATTGAGGAGCTTTTCTTGCCAATGTCTGA
GGCATCAGGTGGCAGGACACGTCTCCCTGCTCTTAAGCCTCAGGCATGCAGCCCTTCTTA
TGCTCTCTGGGGTGAGGGGGAGATCCCCCTCATGGAATTGCTTTTTTTTTTTTTTTTTTT
[-,T]
TTTTGAGACAGGGTCCTGCTCTGTCACTCAGGCTGGAGTGCAGCCTCAACCTCCCAGACT
CAAGTGATCCTCCTGCCTCAGCCTCCCGAGTAGCTGGGACCACAGGTGGACACCATCACA
CCTGGGTTTTTTTGTTTTTTGTTTTTGTTTTCTAGAGATGGGGTCTCACTTTCTTGCTC
AGTCTGGTCTCGAACTCCTGGGCGCAAGCAGTCCTCCCACCTCGTCTTCCCAAAGTGTTT
GGATTACAGGTGTGAGCCACTGTGCTTGGCCTTTTTATTTATTTAGAATTTGTTTTGGAA (SEQ ID NO:21)

17582 GGATGTTTCTTCCATGACATATATAGCTCTTGAAACTACTTCTATCTAATATCACCCACA
GTGCTGTTAAAAATACAGATTTCTGGGCCTCACCCTCAAATTATGATTCAGTAGGTCTAG
GCACGTCAAGGTCATTGTTTTTGTCTTTGTTTTAAGTCACCCCAGGTGATTCTAAAGCCG
AAGCTCTGCAAAGCACACCTTGAGAAACAGAGAACTCTTGTGCTCTCGCTCTCTTGACAC
TTCAGGTGCAAAACTTTTGTCCTAATGTCGTTCTCAAACTTACGCATGTGTGAGAATCAC
[T,C]
GTGAGAGCTTATTGAAACTGATTGCGGGACCCCATACCTAGAGGGCCTGATTCTATAGGT
CTGAGGTAAGGCCCAAGAATTTGCATATTTGCATTTCGTTTTCTTTTCCTTTCTTTTCTT
TTTTTTTTTTTTTGAGATGAAGTCTCACCCTGTCGCCCAGACTGGAGTGCAGTGGCATGA
TCTCAGCTCACTGCAGCCTCTGCCTCCTGGGTTAAAGCGATTCTCCCCACACCCCAGACC
CGCTCCTGAGTAGCTGGGATTACAGGTGCCCGCCACCATGACTAGCTAACGTTTGTATTT (SEQ ID NO:22)

17700 AGGCACGTCAAGGTCATTGTTTTTGTCTTTGTTTTAAGTCACCCCAGGTGATTCTAAAGC
CGAAGCTCTGCAAAGCACACCTTGAGAAACAGAGAACTCTTGTGCTCTCGCTCTCTTGAC
ACTTCAGGTGCAAAACTTTTGTCCTAATGTCGTTCTCAAACTTACGCATGTGTGAGAATC
ACTGTGAGAGCTTATTGAAACTGATTGCGGGACCCCATACCTAGAGGGCCTGATTCTATA
GGTCTGAGGTAAGGCCCAAGAATTTGCATATTTGCATTTCGTTTTCTTTTCCTTTCTTTT
[C,T]
TTTTTTTTTTTTTTTGAGATGAAGTCTCACCCTGTCGCCCAGACTGGAGTGCAGTGGCAT
GATCTCAGCTCACTGCAGCCTCTGCCTCCTGGGTTAAAGCGATTCTCCCCACACCCCAGA
CCCGCTCCTGAGTAGCTGGGATTACAGGTGCCCGCCACCATGACTAGCTAACGTTTGTAT
TTTTAGTAGAGACGGGGGTTTCACCATGTTGGCCAGGCTGGTCTCAAACTCCTGACCTCA
GGTGATCCACTCACCTCAGCCTCCCAAGGTCTTGGGATTACTGGTGTGAGCCACCGCGTG (SEQ ID NO:23)

18074 TGCAGCCTCTGCCTCCTGGGTTAAAGCGATTCTCCCCACACCCCAGACCCGCTCCTGAGT
AGCTGGGATTACAGGTGCCCGCCACCATGACTAGCTAACGTTTGTATTTTTAGTAGAGAC
GGGGGTTTCACCATGTTGGCCAGGCTGGTCTCAAACTCCTGACCTCAGGTGATCCACTCA
CCTCAGCCTCCCAAGGTCTTGGGATTACTGGTGTGAGCCACCGCGTGCGGCCAGAATTTG
CATTTCTAACAAGTCCCAGGTGATGCTGATGCTGTGGGTCCAGGGACACACTTTGAGAAC
[T,C,A]
GCTTGTTACTCAGGCGATATGTGGACAGTAGCGTCATCTTCACCTGGGAGCTTCCTGCAG
CATCTCAGGCCTTGCCCTACACCTACCAGATCAGAATCTGCATTTTAACTCAATCCCCGC
GTGATTCTCATGCACCTGGAAGTTTGAGAAATATGACCTTAGAGGAGCCGGAATGTGAAA
CCACTGGAGGCAGAGATAGATGGAGAATATCTCTTCTTCTCACGGATACTAAAGATGCAA
CAAAAAGGGCTGACTCTCTGGGTGTGCACCCAGGTGGGGCTGATGACCGAAAAGAGGCCA (SEQ ID NO:24)

19328 TGTGTGTGAGGCCGGGGAGTGCTGCGAGCCCCGGAATTCCTCAGCCTTAGTCCCCCGCCA
CATAGCTAAGAAGTGAGGGAGGAGGTGAGAAGGAGTCACTGCCCAGCCTCACTTCCGGTG
GAGTACCCTGTCTCCTTGTCAGTTCTGTCTCTGGGGACAGTTGCCTGCTTTCACCTCTCC
CTCCATCCCCTCTTCTCTCACAGGGAAAAATTCACCTTAATATTGGAAGTTCCTCTCCTA

FIGURE 3M

GCAAAGTCCTTCTCAGGCACCCACAGGCAAAAAGGAAACTAAGCAGAGTTAGGGCTTCCA
[G,T]
GCCTAGCCAACTACACGACTCTCCTCTTGCTTCCCTAAGAACCAGCGCAAGGGGCAGCGT
GGGTTCCAGCATAGATGGACCTGTGTTGGAATCTCTGCACGTGCTGTGCTGACCCTGGCT
AGCCATTGACCTCTCTGAGCCCTTGTTTCCTTTCCACTAGGCTCTCTGAGGGCAGGGGCC
ATGTCTTTTTCACTGCTCTGTCTGCACTGAGCACTGTGCAGGGCACATAGGAAGTTCCCA
TAAATGTTTGTGGGATAAAGGAAATAAAACCTTCTCTCTTCCTGTCCCCCTTGTGATGGC (SEQ ID NO:25)

19570 AAAGTCCTTCTCAGGCACCCACAGGCAAAAAGGAAACTAAGCAGAGTTAGGGCTTCCAGG
CCTAGCCAACTACACGACTCTCCTCTTGCTTCCCTAAGAACCAGCGCAAGGGGCAGCGTG
GGTTCCAGCATAGATGGACCTGTGTTGGAATCTCTGCACGTGCTGTGCTGACCCTGGCTA
GCCATTGACCTCTCTGAGCCCTTGTTTCCTTTCCACTAGGCTCTCTGAGGGCAGGGGCCA
TGTCTTTTTCACTGCTCTGTCTGCACTGAGCACTGTGCAGGGCACATAGGAAGTTCCCAT
[A,G]
AATGTTTGTGGGATAAAGGAAATAAAACCTTCTCTCTTCCTGTCCCCCTTGTGATGGCTT
TGCACAAGGCACTGTCCTTGGCCAGGTTTGCTAGGCTAGTGTGAGGATAAACCAGGTATA
TTACAAATTGGAGAAAATTTCTCGTTCTTCTTGGAAGAAGGTGCTGTATCATGAAACAAG
AATGTCTTGATTCCCTTCTATGCCAGGTACTGGGGAGAAACAGGTGCCTGATAACCGTTG
ATCCAGGCAGAAATAAGCATACTCCTGCTTCCCAAGGCCTGATGCTTCTCTCCTTCCTCC (SEQ ID NO:26)

20892 CCTTGGATGAAGAAGCGTGGGAACTCTTTGCTTCCTTTCCCTCCCGCAGTGACATGCCAT
GCCATGCCACTGCCTCTTCATCTGGTCCTATGACAGTCACTCATAAGCACCCGCATGTAC
CCGGCCCTGCACTAGCTCATGACAGCTGCAGTCAATTGGGCCAGGTGCTGTATCTCATCC
GGCCTCCTCAGCAACCCTCTGAGATACTGGTAATGTCCCTGATGAAGATATTTACTGAGG
CAGAAATGGACGCTCAGTGAAGCAAGGTGCCTGATGTTATAGCAATGAGCTATGAGTGGC
[C,T]
AGAGGGAGGAGATAAGCTCAGGCCTGACACCAAAGCCCATGCTCCTTCTAGTCAACCACA
GTGCCTCCTATGGTGAATGAGTGAGTCAGCAACCAAGACGCATGAGGCCTTCTTTTTGGT
GAGCCTTGGCTGGGTGCTGAGGCTTCAGGTACAATCATGGGTTGGAAGAGCCCTCCTCTC
TCTCCACAGTCTGGCACTATGACCCCTTCTGGTTATTAACAAGGCAAAGAGAGAGAGGGA
AGAAAGCAGGCAAATAATGTGGGTTGCTATTCCTAGAGATTAGAATTTCAGGAAGGATAA (SEQ ID NO:27)

26465 TTCTCTGACCCCTCCCCTCCGGTGCGTTTCGTATCAAAGCTCCTCAAACCCCGTCCCCCG
TGTGTCCTGCTGTGTGCAGCTCGCTCTTTCCTTCCTTCCTAAGCTATCCAAGGGGATGGA
CCCAGGCTCGTGGGGAGGTTCCACCCTTGGATCCAGGAAGAACCCTCCACCCTGCCTCGT
GGGTGGCCAAAGGCTACAGGGTGCTTCTTCCTCTTCCCCCACCCCCACTGTCCCTCATG
TGCCATGGGCCTGCCTCCCCAGTGACCTGCGAAAGTGGAGCATCGAGGTAGGAGGGAAAC
[G,A]
GCAACCAGGGAGTCCTCGAGCCTGGGGCTGCCCTACCTCTACCCATTCCCCGACCAGAGC
TTTGCCCTTGCTTGGCTGCCCGCCTGCCTCTTTGGGGAACTGAGCTCAGAGGCAGGTGCT
TCAGAGAAGGAAACAAAATGAGGGGTGGCAGGGATAAAAAGTCACCTCCATTCTCTACCT
CCCATGCAGCATGAACACAATTTCTCTCCACCTGGCTCCCAAATTTAAAGATGTGGACCA
AGGCCTGTGGGTACTCCAGGGGCAAGGAGAGCCCTGGGGTCAGTGACACTGTCAGGCCAA (SEQ ID NO:28)

26472 ACCCCTCCCCTCCGGTGCGTTTCGTATCAAAGCTCCTCAAACCCCGTCCCCCGTGTGTCC
TGCTGTGTGCAGCTCGCTCTTTCCTTCCTTCCTAAGCTATCCAAGGGGATGGACCCAGGC
TCGTGGGGAGGTTCCACCCTTGGATCCAGGAAGAACCCTCCACCCTGCCTCGTGGGTGGG
CCAAAGGCTACAGGGTGCTTCTTCCTCTTCCCCCACCCCCACTGTCCCTCATGTGCCATG
GGCCTGCCTCCCCAGTGACCTGCGAAAGTGGAGCATCGAGGTAGGAGGGAAACGGCAACC
[A,G]
GGGAGTCCTCGAGCCTGGGGCTGCCCTACCTCTACCCATTCCCCGACCAGAGCTTTGCCC
TTGCTTGGCTGCCCGCCTGCCTCTTTGGGGAACTGAGCTCAGAGGCAGGTGCTTCAGAGA
AGGAAACAAAATGAGGGGTGGCAGGGATAAAAAGTCACCTCCATTCTCTACCTCCCATGC
AGCATGAACACAATTTCTCTCCACCTGGCTCCCAAATTTAAAGATGTGGACCAAGGCCTG
TGGGTACTCCAGGGGCAAGGAGAGCCCTGGGGTCAGTGACACTGTCAGGCCAACCATGCA (SEQ ID NO:29)

FIGURE 3N

28071 GCCAGGGACTTGAGAAGTTATATTGGGCAGTGGCTCCAATCTGTGGACCAGTATTTCAGC
TTTCCCTGAAGATCAGGCAGGGTGCCATTCATTGTCTTTCTCTCCTAGCCCCCTCAGGAA
AGAAGGACTATATTTGTACTGTACCCTAGGGGTTCTGGAAGGGAAAACATGGAATCAGGA
TTCTATAGACTGATAGGCCCTATCCACAAGGGCCATGACTGGGAAAAGGTATGGGAGCAG
AAGGAGAATTGGGATTTTAGGGTGCAGCTACGCTCACCCTAAACTTTTGGTGGCCTGGGG
[C,T]
ATGTCTTGAGGCCCAGACTGTTAACCAGGCTCTGCTGGCCTGTTTACTCGTCACCACCTC
TGCACCTGCTGTCTTGAGACTCCATCCAGCCCCAGGCACGCCACCTGCTCCTGAGCCTCC
ACTATCTCCCTGTGACGGGTGAACTTCGTGTACTGTGTCTCGGGTCCATATATGAATTGT
GAGCAGGGTTCATCTATTTTAAACACAGATGTTTACAAAATAAAGATTATTTCAAACCAC
CGGTGTGGCTGCCTGGATGAGTCCTTGGGGGTAGGTCTCACTCAGACCCTGGCAGTGATG (SEQ ID NO:30)

28096 GGCAGTGGCTCCAATCTGTGGACCAGTATTTCAGCTTTCCCTGAAGATCAGGCAGGGTGC
CATTCATTGTCTTTCTCTCCTAGCCCCCTCAGGAAAGAAGGACTATATTTGTACTGTACC
CTAGGGGTTCTGGAAGGGAAAACATGGAATCAGGATTCTATAGACTGATAGGCCCTATCC
ACAAGGGCCATGACTGGGAAAAGGTATGGGAGCAGAAGGAGAATTGGGATTTTAGGGTGC
AGCTACGCTCACCCTAAACTTTTGGTGGCCTGGGGCATGTCTTGAGGCCCAGACTGTTAA
[C,G]
CAGGCTCTGCTGGCCTGTTTACTCGTCACCACCTCTGCACCTGCTGTCTTGAGACTCCAT
CCAGCCCCAGGCACGCCACCTGCTCCTGAGCCTCCACTATCTCCCTGTGACGGGTGAACT
TCGTGTACTGTGTCTCGGGTCCATATATGAATTGTGAGCAGGGTTCATCTATTTTAAACA
CAGATGTTTACAAAATAAAGATTATTTCAAACCACCGGTGTGGCTGCCTGGATGAGTCCT
TGGGGGTAGGTCTCACTCAGACCCTGGCAGTGATGTGGGAGGGAGAGAGGCAGTGCTGGT (SEQ ID NO:31)

28403 CTGCTGGCCTGTTTACTCGTCACCACCTCTGCACCTGCTGTCTTGAGACTCCATCCAGCC
CCAGGCACGCCACCTGCTCCTGAGCCTCCACTATCTCCCTGTGACGGGTGAACTTCGTGT
ACTGTGTCTCGGGTCCATATATGAATTGTGAGCAGGGTTCATCTATTTTAAACACAGATG
TTTACAAAATAAAGATTATTTCAAACCACCGGTGTGGCTGCCTGGATGAGTCCTTGGGGG
TAGGTCTCACTCAGACCCTGGCAGTGATGTGGGAGGGAGAGAGGCAGTGCTGGTAGAAGC
[A,G]
GCTCCAGAAGCAAAGGCAACAGCAGTAGAGTGACCACGGAAGCGGCAAACATTGTCTTCC
CTTCTCTACCTTCCCTAGTGCCACCTGCAGGGAGGCCCAAAGCAAAGCCCCGTTGCCCTG
CATTGGGCTGGCACTGCAGAAATAAGATGAAACACAGTTATCGAGAGGATGCTGAACATC
TATGAGCAGGTTTTAAAGCCAAGATGAGTCTCATCTGTTTGTGTGGGTCAGGAACGGGTC
TTCCTGAAGGCATGAGGTGGGACTGGATAATCTTTCAGATTTGTGATTGGATACCTCGGG (SEQ ID NO:32)

28467 GCACGCCACCTGCTCCTGAGCCTCCACTATCTCCCTGTGACGGGTGAACTTCGTGTACTG
TGTCTCGGGTCCATATATGAATTGTGAGCAGGGTTCATCTATTTTAAACACAGATGTTTA
CAAAATAAAGATTATTTCAAACCACCGGTGTGGCTGCCTGGATGAGTCCTTGGGGGTAGG
TCTCACTCAGACCCTGGCAGTGATGTGGGAGGGAGAGAGGCAGTGCTGGTAGAAGCAGCT
CCAGAAGCAAAGGCAACAGCAGTAGAGTGACCACGGAAGCGGCAAACATTGTCTTCCCTT
[C,G]
TCTACCTTCCCTAGTGCCACCTGCAGGGAGGCCCAAAGCAAAGCCCCGTTGCCCTGCATT
GGGCTGGCACTGCAGAAATAAGATGAAACACAGTTATCGAGAGGATGCTGAACATCTATG
AGCAGGTTTTAAAGCCAAGATGAGTCTCATCTGTTTGTGTGGGTCAGGAACGGGTCTTCC
TGAAGGCATGAGGTGGGACTGGATAATCTTTCAGATTTGTGATTGGATACCTCGGGGGAG
CAGAGGCAGACTGGGATCTCAGGACTGCAGGTATTTCATACTTTGGGATATGGAATTGAT (SEQ ID NO:33)

FIGURE 3O

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the Rab subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the Rab subfamilies, are a major target for drug action and development. Accordingly, it is valuable to the field of pharmaceutical development to identify and characterize previously unknown members of this subfamily of Ras-like proteins. The present invention advances the state of the art by providing a previously unidentified human Ras-like proteins that have homology to members of the Rab subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal-transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF), insulin, an interleukin (IL), granulocyte colony-stimulating factor (G-CSF), granulocyte/macrophage colony-stimulating factor (GM-CSF).

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) that regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal-transducing proteins are members of the Ras superfamily.

The Ras superfamily is a class of low molecular weight (LMW) GTP-binding proteins that consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization that is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I-IV) have been studied in the LMW GTP-binding proteins. Motif I is the most variable but has the conserved sequence, GXXXXGK (SEQ ID NO:34). The lysine residue is essential in interacting with the .beta.- and .gamma.-phosphates of GTP. Motif II, III, and IV contain highly conserved sequences of DTAGQ (SEQ ID) NO:35), NKXD (SEQ ID NO:36), and EXSAX (SEQ ID NO:37), respectively. Specifically, Motif II regulates the binding of gamma-phosphate of GTP; Motif m regulates the binding of GTP; and Motif IV regulates the guanine base of GTP Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX; SEQ ID NO:38) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with Ca.sup.2+-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX (SEQ ID NO:38) motif that binds a prenyl group and either a palmitoylation site or a basic amino acid-rich region, suggesting their role in membrane-associated functions. In particular, RhoD is a protein that functions in early endosome motility and distribution by inducing rearrangement of actin cytoskeleton and cell surface (Murphy, C. et al. (1996) Nature 384:427–432). Dining cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of senne/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10:1793–1798). Rin and Rit are characterized as membrane-binding, Ras-like proteins without the lipid-binding CAAX (SEQ ID NO:38) motif and carboxy terminal cysteine (Lee, C.-H. J. et al. (1996) J. Neurosci. 16: 6784–6794). Further, Rin is shown to localize in neurons and have calcium-dependant calmodulin-binding activity.

Rab Proteins

The novel human protein, and encoding gene, provided by the present invention is related to the Rab subfamily of Ras proteins and shows a high degree of similarity to Rab15. Furthermore, the protein of the present invention may be a novel alternative splice form of a protein provided in WO200058473; specifically, the protein of the present invention differs from the art-known protein of WO200058473 in exon 6 (see amino acid sequence alignment in FIG. 2).

Rab15 may act, together with Rab3A, to regulate synaptic vesicle membrane flow within nerve terminals, thereby regulating neurotransmitter release. Rab15 and Rab3A are low molecular weight GTP-binding proteins. Rab proteins are generally comprised of four conserved structural domains necessary for GTP binding, as well as additional domains for membrane localization and effector protein interactions. Rab15 is expressed primarily in neural tissues such as the brain and is localized to synaptic vesicles (Elferink et al., *J. Biol. Chem.* 267 (9), 5768–5775 (1992)).

Due to their importance in neural physiology, particularly in regulating neurotransmitter release, novel human Rab proteins/genes, such as provided by the present invention, are valuable as potential targets for the development of therapeutics to treat neurological disorders. Furthermore, SNPs in Rab genes, such as provided by the present invention, are valuable markers for the diagnosis, prognosis, prevention, and/or treatment of neurological disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays.

The discovery of new human Ras-like proteins and the polynucleotides that encode them satisfies a need in the art by providing new compositions that are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the Rab Ras-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in the brain and in tumors.

DESCRIPTION OF THE FIGURE SHEETS

FIG. 1 provides the nucleotide sequence of a cDNA molecule that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the brain and in tumors.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 20 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the Rab subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the Rab subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the Rab subfamily and the expression pattern observed. Experimental data as provided in FIG. 1 indicates expression in the brain and in tumors. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known Rab family or subfamily of Ras-like proteins.

Specific Embodiments

Peptide Molecules

The present invention provides nucleic acid sequences that encode protein molecules that have been identified as being members of the Ras-like protein family and are related to the Rab subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in the brain and in tumors. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I, Griffin, A. M., and Griffin, H. G., eds., Humana Press, New Jersey,* 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. MoL*

*Biol.* 2 15:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel Ras-like protein of the present invention is located on a genome component that has been mapped to human chromosome 14 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel Ras-like protein of the present invention is located on a genome component that has been mapped to human chromosome 14 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. SNPs were identified at 20 different nucleotide positions. Some of these SNPs that are located outside the ORF and in introns may affect gene transcription.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain. A large percentage of pharmaceutical agents are being developed that modulate the activity of Ras-like proteins, particularly members of the Rab subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the brain and in tumors. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the Rab subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain.

The proteins of the present invention are also useful in drug screening assays, in cell-based or cell-free systems.

Cell-based systems can be native, i.e., cells that normally express the Ras-like protein, as a biopsy or expanded in cell culture. Experimental data as provided in FIG. 1 indicates expression in the brain and in tumors. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, Rab or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising Rab may be administered to a subject to prevent or treat a disorder associated with increased apoptosis including, but not limited to, those listed above.

In still another embodiment, an agonist which is specific for Rab may be administered to prevent or treat a disorder associated with increased apoptosis including, but not limited to, those listed above.

In a further embodiment, a vector capable of expressing Rab, or a fragment or a derivative thereof, may be used to prevent or treat a disorder associated with increased apoptosis including, but not limited to, those listed above.

In cancer, where Rab promotes cell proliferation, it is desirable to decrease its activity. Therefore, in one embodiment, an antagonist of Rab may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for Rab may be used directly as an antagonist, or indirectly as a targeting or delivery mechanism for bringing a pharmaceutical agent to cells or tissue which express Rab.

In another embodiment, a vector expressing the complement of the polynucleotide encoding Rab may be administered to a subject to prevent or treat a cancer including, but not limited to, the types of cancer listed above.

In inflammation, where Rab promotes cell proliferation, it is desirable to decrease its activity. Therefore, in one embodiment, an antagonist of Rab may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for Rab may be used directly as an antagonist, or indirectly as a targeting or delivery mechanism for bringing a pharmaceutical agent to cells or tissue which express Rab.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sep. 10(9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in the brain and in tumors. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in the brain and in tumors. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the brain and in tumors. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the brain and in tumors. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the brain and in tumors. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the brain and in tumors. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated"

nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel Ras-like protein of the present invention is located on a genome component that has been mapped to human chromosome 14 (as indicated in FIG. 3), which is supported by multiple lines of evidence, such as STS and BAC map data.

FIG. 3 provides information on SNPs that have been found in the gene encoding the Ras-like protein of the present invention. SNPs were identified at 20 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2× SSC, 0.1% SDS at 50–65° C. Examples of moderate to low stringencyhybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 20 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel Ras-like protein of the present invention is located on a genome component that has been mapped to human chromosome 14 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that Ras-like proteins of the present invention are expressed in the brain and in tumors, as indicated by virtual northern blot analysis. hi addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain.

Nucleic acid expression assays are useful for drug screening to identify compounds that modulate Ras-like protein nucleic acid expression.

The invention thus provides a method for identifing a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in the brain and in tumors. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as mRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in the brain and in tumors.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. SNPs were identified at 20 different nucleotide positions. Some of these SNPs that are located outside the ORF and in introns may affect gene transcription. The gene encoding the novel Ras-like protein of the present invention is located on a genome component that has been mapped to human chromosome 14 (as indicated in FIG. 3), which is supported by multiple lines of evidence, such as STS and BAC map data. Genomic DNA can be analyzed directly or can be amplified by using PCR prior to analysis.

RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al, *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. SNPs were identified at 20 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of mRNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that Ras-like proteins of the present invention are expressed in the brain and in tumors, as indicated by virtual northern blot analysis. In addition, PCR-based tissue screening panels indicate expression in fetal brain. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. SNPs were identified at 20 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET lid (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kjan et al., *Cell* 30:933–943(1982)) pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165(1983)) and the pVL series (Lucklow et al, *Virology* 170:31–39(1989)).

In certain embodiments of the invention, the nucleic acid molecules described herein are expressed in mammalian cells using mammalian expression vectors. Examples of mammalian expression vectors include pCDM8 (Seed, *B. Nature* 329:840(1987)) and pMT2PC Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory, Cold Spring Harbor Laboratory Press, Cold Spring Harbor, N.Y.,* 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:

(a) a nucleotide sequence that encodes a polypeptide comprising the amino acid sequence of SEQ II) NO:2;

(b) a nucleotide sequence consisting of SEQ ID NO:1;

(c) a nucleotide sequence consisting of SEQ ID NO:3; and (d) a nucleotide sequence that is completely complementary over the entire length of a nucleotide sequence of (a)–c).

2. A vector comprising the nucleic acid molecule of claim 1.

3. The vector of claim 2, wherein said vector is selected from the group consisting of a plasmid, a virus, and a bacteriophage.

4. The vector of claim 2, said isolated nucleic acid molecule is inserted into said vector in proper orientation and correct reading frame such that a polypeptide comprising SEQ ID NO:2 may be expressed by a cell transformed with said vector.

5. The vector of claim 3, wherein said isolated nucleic acid molecule is operatively linked to a promoter sequence.

6. An isolated host cell containing the vector of claim 2.

7. A process for producing a polypeptide comprising the amino acid sequence of SEQ ID NO:2, the process comprising culturing the host cell of claim 6 under conditions sufficient for the production of said polypeptide, and recovering said polypeptide, thereby producing said polypeptide.

8. An isolated polynucleotide consisting of the nucleotide sequence of SEQ ID NO:1.

9. An isolated polynucleotide consisting of the nucleotide sequence of SEQ ID NO:3.

* * * * *

SEQUENCE LISTING

<160> NUMBER OF SEQ ID NOS: 38

<210> SEQ ID NO 1
<211> LENGTH: 3257
<212> TYPE: DNA
<213> ORGANISM: Homo sapiens

<400> SEQUENCE: 1

```
tgcccgctgc ccgcccgcag ttcccggccc cgctggcccc agtcatggcg aagcagtacg     60
atgtgctgtt ccggctgctg ctgatcgggg actccggggt gggcaagacc tgcctgctgt    120
gccgcttcac cgacaacgag ttccactcct cgcacatctc caccatcggt gttgacttta    180
agatgaagac catagaggta gacggcatca aagtgcggat acagatctgg gacactgcag    240
ggcaggagag ataccagacc atcacaaagc agtactatcg gcgggcccag gggatatttt    300
tggtctatga cattagcagc gagcgctctt accagcacat catgaagtgg gtcagtgacg    360
tggatgagta cgcaccagaa ggcgtccaga agatccttat tgggaataag gctgatgagg    420
agcagaaacg gcaggtggga agagagcaag ggcagcagct ggcgaaggag tatggcatgg    480
acttctatga aacaagtgcc tgcaccaacc tcaacattaa agagtcattc acgcgtctga    540
cagagctggt gctgcaggcc cataggaagg agctggaagg cctccggatg cgtgccagca    600
atgagttggc actggcagag ctggaggagg aggagggcaa acccgagggc ccagcgaact    660
cttcgaaaac ctgctggtgc tgagtcctgt gtggggcacc ccacacgaca cccctcttcc    720
ctcaggaggc ccgtgggcag acaggggagc cggggctttg ccctgctgct gtcctctcgt    780
gtgatgaccc tattgagtat cagtagccac tactccccct gcctggccct gagagcggct    840
ctgctgtcat ctcaagcagc ccctgtcccc agcccgtcca ccctggagtg gtcttcttca    900
gcctgtttcc ccagccacag gcctgctacg acccccacga tgtgccgcaa gcactgtctc    960
accatcccgc acccaccaga caacagccag ggctggagtc caggccactt tcagctgctc   1020
ctttctccgt gcatcgtgtc tcttctctgc tttttctctc ttcccccact tctctttctc   1080
tgacccctcc cctccggtgc gtttcgtatc aaagctcctc aaaccccgtc ccccgtgtgt   1140
cctgctgtgt gcagctcgct ctttccttcc ttcctaagct atccaagggg atggacccag   1200
gctcgtgggg aggttccacc cttggatcca ggaagaaccc tccaccctgc ctcgtgggtg   1260
ggccaaaggc tacagggtgc ttcttcctct tcccccaccc ccactgtccc tcatgtgcca   1320
tgggcctgcc tccccagtga cctgcgaaag tggagcatcg aggtaggagg gaaacagcaa   1380
ccggggagtc ctcgagcctg ggctgccct  acctctaccc attccccgac cagagctttg   1440
cccttgcttg gctgcccgcc tgcctctttg gggaactgag ctcagaggca ggtgcttcag   1500
agaaggaaac aaaatgaggg gtggcaggga taaaaagtca cctccattct ctacctccca   1560
tgcagcatga acacaatttc tctccacctg gctcccaaat ttaaagatgt ggaccaaggc   1620
ctgtgggtac tccaggggca aggagagccc tggggtcagt gacactgtca ggccaaccat   1680
gcactccaca aaggggagca tttggaaatg aaggactagc tcctatgtat caggttaaga   1740
gcaagggaga gctggccagg gacagcagtt tgcacagcag aggggaatgt agcaacagca   1800
gggcctccta ggccccatct tccatttctt aggtaagaag agcatttcct cagactccca   1860
ggcggaggac tgagcctagc cttcagcaac caaggttctc ctgggaccca aagtttatgg   1920
gagaagggca aagacttcat gggaagagag aaggaaggcc ctgggtagaa acgcttggtg   1980
ctgttctctt tggcctttaa gacaaagcgc tcatcttgcc ctctacctcc tgataggctt   2040
```

-continued

```
gagggtttgc caaccacact gtggctacag gtggagggaa gaggactcct tcctccagag   2100

tgctatgttc aggaagtttc tttaacccca tatggcccaa gagtagctcg taggaggccc   2160

tttaaagacg gaacaagtaa tttaccagtt ctactggggt tcctgcccac cgtcccaagg   2220

tgggcgaggc ctaggaagag ggtcattctt aagccacaca ttagctgcac tgcgtggctg   2280

cagccaaaac aaagaactgg gtgttgagta ttcatcaact aagaaccaaa atccagggca   2340

ctcatatgtg aaggataaga acctcacttc cttactcctc caaaaagaag tggggaaaga   2400

accatcaaac ctttcctcct gacttaccaa accaggaaaa cagcaggaga gggtggctca   2460

ggacttaggg acagggtata gcttagatgg tggaaagcaa aggagagcag gaagttgtaa   2520

atcactggct aatgagaaaa ggagacagct aactctagga tgaagctgtg actaggctgg   2580

agttgcttcc ttgaagatgg gactccttgg gtatcaagac ctatgccaca tcacactggg   2640

gctagggaag taggtgatgc cagccctcaa gtctgtcttc agccagggac ttgagaagtt   2700

atattgggca gtggctccaa tctgtggacc agtatttcag ctttccctga agatcaggca   2760

gggtgccatt cattgtcttt ctctcctagc cccctcagga aagaaggact atatttgtac   2820

tgtaccctag gggttctgga agggaaaaca tggaatcagg attctataga ctgataggcc   2880

ctatccacaa gggccatgac tgggaaaagg tatgggagca gaaggagaat tgggatttta   2940

gggtgcagct acgctcaccc taaacttttg gtggcctggg gcatgtcttg aggcccagac   3000

tgttaagcag gctctgctgg cctgtttact cgtcaccacc tctgcacctg ctgtcttgag   3060

actccatcca gccccaggca cgccacctgc tcctgagcct ccactatctc cctgtgacgg   3120

gtgaacttcg tgtactgtgt ctcgggtcca tatatgaatt gtgagcaggg ttcatctatt   3180

ttaaacacag atgtttacaa aataaagatt atttcaaacc accaaaaaaa aaaaaaaaaa   3240

aaaaaaaaaa aaaaaaa                                                  3257
```

<210> SEQ ID NO 2
<211> LENGTH: 212
<212> TYPE: PRT
<213> ORGANISM: Homo sapiens

<400> SEQUENCE: 2

```
Met Ala Lys Gln Tyr Asp Val Leu Phe Arg Leu Leu Leu Ile Gly Asp
 1               5                  10                  15

Ser Gly Val Gly Lys Thr Cys Leu Leu Cys Arg Phe Thr Asp Asn Glu
            20                  25                  30

Phe His Ser Ser His Ile Ser Thr Ile Gly Val Asp Phe Lys Met Lys
        35                  40                  45

Thr Ile Glu Val Asp Gly Ile Lys Val Arg Ile Gln Ile Trp Asp Thr
    50                  55                  60

Ala Gly Gln Glu Arg Tyr Gln Thr Ile Thr Lys Gln Tyr Tyr Arg Arg
65                  70                  75                  80

Ala Gln Gly Ile Phe Leu Val Tyr Asp Ile Ser Ser Glu Arg Ser Tyr
                85                  90                  95

Gln His Ile Met Lys Trp Val Ser Asp Val Asp Glu Tyr Ala Pro Glu
            100                 105                 110

Gly Val Gln Lys Ile Leu Ile Gly Asn Lys Ala Asp Glu Glu Gln Lys
        115                 120                 125

Arg Gln Val Gly Arg Glu Gln Gly Gln Gln Leu Ala Lys Glu Tyr Gly
    130                 135                 140

Met Asp Phe Tyr Glu Thr Ser Ala Cys Thr Asn Leu Asn Ile Lys Glu
145                 150                 155                 160
```

-continued

```
Ser Phe Thr Arg Leu Thr Glu Leu Val Leu Gln Ala His Arg Lys Glu
                165                 170                 175

Leu Glu Gly Leu Arg Met Arg Ala Ser Asn Glu Leu Ala Leu Ala Glu
            180                 185                 190

Leu Glu Glu Glu Glu Gly Lys Pro Glu Gly Pro Ala Asn Ser Ser Lys
        195                 200                 205

Thr Cys Trp Cys
    210
```

<210> SEQ ID NO 3
<211> LENGTH: 28770
<212> TYPE: DNA
<213> ORGANISM: Homo sapiens

<400> SEQUENCE: 3

```
gctcaagatt gcacagctgg tgagtggtga cactgggact ggaacccaag tgtgccttac      60

tccagagccc ttggcatgca cctgaaaccc catgtaagcc cactgtggag acgcgcacct     120

cgaaataatg gaatccacta catcagttcc tttagctttc tgtgtaatca gagtagctag     180

caggctcggg atttcgcccc ccggcttttt tttttttttt tttttgagac agagttttgc     240

tcttgttgcc caggctggag tgcaatggcg caatctcggc tcaccgcaac cttcgcctct     300

caggttcaag caattctcct gcctcagcct cccgagtagc tgggattaca ggcaccggcc     360

accacgccca gctaattttt ttatattttt agtagagatg gggtttcacc atgttggcca     420

ggctggtctt gaactttccc cctcttatta taattcagac acttaacctg aaatatacct     480

tttcaaatga agtaaatggg cttaccactt tccttgacct actattgaaa aatacattct     540

ccatccaata ttcagcctga aaacaggtat gtacatatat acttttcatt gctttttttt     600

tttttttttt gagacaaggt ctccctctgt tgcgcaggct ggagtgcagt gtcatgatct     660

cggctcactg cagccttccc ctaatgggtt caagcaatcc tcccacctca gcctctcaag     720

cctgggatta caggcgagcc accgtgccca gctaattttt ttttattttt agtagagact     780

gggtttcact acattggcca ggctggtctc cagctcctga cctcaaagtg atctgcccgc     840

ctcagcctcc caaagtactg ggattacagg catgagccaa cgcgcctagc ctttcattgc     900

tttttaaaga cctaataggc tagactttgc tctccctcaa tactcgttgg tagggatagg     960

caattttctc aactccggag agcattcatt tgcctctctc cggtgctaac acattcagtg    1020

gtaggaaact ggatcttgaa caagggccat tcattctttg gtgccactgg ctataccaca    1080

gagaaattta ggggtctgaa acaatacatt ggtcacctgg gcacctatcc taagcacctt    1140

agagggaaaa cggagacttg cccgcacacc tctaaaggat tttgcacttg gagatgttct    1200

tatggccatc tatcttttca ccctggtgga ggccgtgaat aggcattttc cccatttaaa    1260

gaaaaaatgg ggacggggga gggccgtgac acagtcacac aggtaagggg cagccagatg    1320

gcagggaggg ggaattccac ccacactctc ggggactcat ggagacgggt gttcgaatcc    1380

agatcctgct caaggccttc ctacctcggg tgagcccagc tgaggtacca gccactgggg    1440

agcccggcca gatcctgcag atgcagggtg ccacggcggg cggaattacc ggcgccagac    1500

ttggggtggg atatggggag aagtggtgag cccggaaagc ggagcacggt agaagtgggc    1560

tgggtggggg ctcacctcaa ctccccccatt cggagcgtcc gcggaaaaac gaaaacgttc    1620

ccccgccccg ggcaggaagg ggttgggagg gggggctggc gccccgcccc agcgtcgcct    1680

gctcgatggg gtcccgctct cctgcgcgcg ctccccgccc cctctctacc ggggcggcgg    1740
```

-continued

```
cggcggcgca ggggaagggg cgggcagggg ccgccgccgg tttctcctcc caccgcctcg   1800
cgccagccca gccgagccga gccgagccga gcgggcgccg cgccgggctc ccgccgcagc   1860
cgcgcttccc ggcacccagc gagcgagtgg gcaggcgggc gggcgaggca gccgcggggg   1920
ccgggcccgg cgtcctcctc gccgcccgca gcgtccccgg gcgggcgcgg gccgcgatgg   1980
cagcggcgga gcagggctga gcccgctgcc cgcccgcagt tcccggcccc gctggcccca   2040
gtcatggcga agcagtacga tgtgctgttc cggctgctgc tgatcgggga ctccggggtg   2100
ggcaagacct gcctgctgtg ccgcttcacc gacaacgagt tccactcctc gcacatctcc   2160
accatcggta aggggcggtg gcccggggcg cccctccctc cccgcccgcg gcccctttcc   2220
ccgccgcccc cgtccccagc tggggaggaa ttgccagccc ctccggctgg aggcggtggc   2280
gccggaggcc ggagtccggg ataaatctcg ggtgagcat aggttttggc aggtgagggt   2340
gtccctgctg cctgccgtcc ggaccagggg tggggtctcc cgcctcttgc cgggaagcct   2400
tccgtcccat caaaccgaga aaccggggt gaggggagct ggtgtaggcc tgggtacccc   2460
gagctggggt agcaagaatc gtagccgctg gaataacacc cccacacccc caggggggagg   2520
ggaagtaaag cttctgctac ggaaaagggg gtcagggtgg agaccggagt cactgaggcg   2580
cccttggttc tgtggtgacc caaggtggag ccggcggggg gcgagggggg gaagagagga   2640
cgtacggagg ggccacaggg atcgagtttc cagggcagag ttgggaaggt aagccgcaag   2700
gtgggacacc tgggggagga cacagatagg gtgaggagcc cctgcgcctg ggaagaggag   2760
acatctgttc tgagggaggc taaagaggat ggaggagtgt caggaatacc tgcccagacc   2820
aaggggtcag aaggcaggca ggacccgcct gagggcatct ctcatctggc agtgctggag   2880
cctgtggtta gagggacaag acccggtggc atcccagaca gcactatgat ggggtcactt   2940
attctaggaa tgggtccatg gcctcccctc tgagacagtc agtctcccgc ttctaggctg   3000
tgaggggccc cctccctgag aagtctgagt agagggaatt tcatcctcag ctgctacccg   3060
ggtcagccct ggagtagcct ctgcattgcc caagcccctg gaaacacctg ctggctggct   3120
ggtcatccat ttggaatgct ctcctagaag tccctgctgc catcagggat gggcaccagc   3180
tctcagcttc ctcttgagga ttcatgtcca caccatcccc cctcccccca acacacattc   3240
cttgctgaga gagaagtagg agcagataga tacagccagg aggaacagaa ccttctggtt   3300
aagaagccag ctttattgtc caagagacct gagacctcac tgtggggcaa agcaaccttg   3360
aatattgcct aaacttctga gctttattta gtttctcatc tgtagaacgg gtataataat   3420
tgcacctacc tgccaagttg ttgtcaagat taaatgagat aacgattgtt aagtgcttag   3480
cacagccaga cacatggtga agctcgataa atgctgattg ttcttactgc tattgccatt   3540
atcattgagc ttttagggtc tcctctcttt gtttcaccaa cttgaagggt gaaacaacag   3600
gacttagggt cagggaacag aacttgtccg tctttctcag aggagctgta aggccaactc   3660
ttaggaaacc caggagcttg ggctgagcca tggtttggat gagagacatt gcagaaagaa   3720
ggggagccta tagacactaa ggctttgtgc ctgccgggag gacttgggga agaggcaggt   3780
gcaggagaaa ggcatgggcg tgatggagga agtggcagag gaaccagatg gtgtatgagg   3840
acaggttgtg ggctcaggga caaagggcgg tgggttatcc cttaaggaaa ctaggagtgg   3900
ctatttttgg gagaggcctg gtgcttggaa ctactgagct atctccagag agctgtgggc   3960
tgcctgggag gccctggctt tggcctgaag agctgttgtt tgcacctgct ctcctagtcc   4020
cattccaagt cctataggtg acatggactt ttccctttga gggcttcatt caaccacctc   4080
atttcagaag ctctgggact cctgcttagt gctgtgggag gcagcctccc ctgggagaca   4140
```

-continued

```
cataccctcc tttttgaggg cacccctctt tctaaaatac caggatggcc ctctgaggct   4200
cgtgctctcc ttaaagagag tccattgcct cacacctcta atcatccacc cttctccttg   4260
tcccttcccc ttgtaatctc ccttcttaga caccttctgc taataggtga acactaaata   4320
ggtcacaggg acttcctgaa accctccagg gcagaccact ttgggcacat aggtgaatca   4380
gtgaactgag taggggtgtc tctgcagcac tgtctcccct caaggccctt ggtatattgg   4440
cctaaaacct aaagatggct cccagatttc ttcctccgct tctgacaccc gggttcccct   4500
ttctacagga cacagaggat tctctagggt ccccctttcc acaggacaca gaggactcta   4560
ggagtttgga ttccatggaa tagaaagaaa cctgtctttc ttcacaccag ccttttaaaa   4620
tctgccccac tgggtatctt aaatgctttc ttatttaaag cttattaagg gacttgggat   4680
tctcccttat cttgggcgtg tttttcagca ttaactaaaa cttaaaggaa agagttggat   4740
ggtcaagaaa agctttttcc ttaagtgata tggacagttt ctcaaggagg tagaaggggc   4800
agccaggaga caaatcaagg agccaacgaa atgagtgcta ccaagtcata gtcattcgct   4860
tatttttaaa aaatgcgtgt cctgtatgcc aggctctgca ctgagaccga gagattccaa   4920
gatgaataat acctacagtc actgttctca aattgtgcat tacctaaaac acattacatg   4980
accatgctgg ccactgatcg aggcaccttt cccaggggct tttttgtga attaagaaaa    5040
caaggtaatt caccagttat tgccaagata gtttggcttc ttggctcatg tggatatcac   5100
ctaggccagt acttttgtga tttactgtgt actccacttt aacggcctgc gatcttctag   5160
agaagaaccc gccagggagc agtgagaggc ctccctggta gactgagaca ctgactgtcc   5220
ctccccctat ccttttcgtc tttctggcca gcagaccagc aggtggccct gccactggct   5280
ctgccacagg catttccttt ctgtgcagct gtgctggcct ggctgggggt tggtgcgaag   5340
gggtccccaa aatactacct taaacaaatt aattgagcat tcactaccaa gctctgtgcc   5400
aggcatttta gagacatatt gcagtctacg ttttctgccc acagaagccc ataacctaga   5460
tggggaggca agacaaaggg aaaaacaaaa aacaaagagc tagtgccaaa atgagatatc   5520
tgaaagaact tggtgaatca ctcttcaaat gtaaaggatg gattatgatc attgcagtta   5580
ctcttaatga aggtctcaca gtgggtatca gaagctaaat tatgatgcaa gatgtaccat   5640
gaggcagccg gagaatggcg atggatggga tgggtgagtg ctattcccac gactccatgc   5700
tgtcggaggc tggggaagag agaggcccct gtggactaga accggcaggg aaggctgaag   5760
ctaggcctca gtgtgggctg ctcgtcagtt cctgcagcag aagggagcag atggagtaac   5820
atgagcagag ataacagagg tgggattgag taggtgtccg tggggctcta ggcagtttag   5880
atgcaacaga agggattctt caggaaagtg agaagattct tctgtttctc tctctgtctc   5940
ccaaattata agtgccttga tggtgcgacc aaatcttatt cctcattgtt tttatagtcc   6000
ctagtacagg gccaggcaga ttcaatgcct gttgttaaat taatgaatga atgcagggac   6060
cagttggcag agggcattga gagcctggcc aaggaggtgg aacatgagcc ttagcaatgg   6120
taggaggggt tttgagtagg gtactaatga ggttggctgg aagaaggggt taagacttga   6180
agcagggaga ctagtcaggg gctgcagtag tatcctgggc atgaaggaac ctctgaatgg   6240
cccctcaccc ccagtggtac caacaccaac ttccacacag tcagttgttc tactttccct   6300
ccagaatggg gagtggttca agccaatcaa cctggcaact tctgaaagaa tcttatggga   6360
cctgtgccat gaccaggtag ggagaagatg tcatacatgg acatctatgt tcaggggacc   6420
tttgaggacc tttctgcatg gtggccagga gtgagatgat gtaaaccaca aatggaaact   6480
```

-continued

```
gaagagactg ctcaggagtt gttggttttc ttttcttttc tattttttt tttttgagac   6540
taggtttcac tctgtcaccc agtctggagt gtggtggtgg cacaatcacg gctcactgca   6600
gcctcgatct cctaaacgca atcctcccac ctcagcctct caagtagctg ggactacagg   6660
tgcatgccac cacattcagc taatgtttgt acgttttgta gagatggggt ttcactatgt   6720
tgaccaggct ggtctcgaac tcctggactc gtgatccacc agcctcagcc ttccaaaatg   6780
ctgggattat aggcgtgagc tacctcactc cctcaggagt tggttttctc cctcccatcc   6840
ttagtcttcc ctgagtagac ctgtcaccta gtccctggac cttttgtttt gaaagccacc   6900
ctccaggcta cactccttct gggtgaggag gagggtgatc tggttggaca ggttgggctg   6960
ctgtggcttc agggcacttt ctcaggctgg gttgctgctg ctatgtcacc tttctcaagg   7020
agttctgctg ggactggctt ggctgcctgt cttgactttg cttttgactg aggaggtggg   7080
agatggtgag ggagggggtg gggctagatc caagcctgga atggggtgac ctaacagaca   7140
ctggggcctg tgcttagaca ctaggatcct ggggtttgca ggtttctaga ctgagaggag   7200
ctgggggcaa atgcagtgtg acgttgtgag agggtcaggg ctgggtctgt gtcagccttc   7260
aggcagcctg agaccagtct ctacctactc tgttcccctg gtacctagaa aggaagggaa   7320
ggtgagaagc aatgagcaga atggaaagag cccagattaa catgcacatt tcccatggcc   7380
ttactggccc tgtgaccttc agacactttg atgacatctt tgtgcttcgt ttctgcatct   7440
gtaaattgaa gatggtaaca gagtctttct taaaggttgt tgtgaagatt atagagccta   7500
gcgcatataa agcacttggc agagccctcg ataaaataat agctgctatc atattatcat   7560
tattattatt ttatttattt atttatttat ttttttttga gaccgagtat ctctctgtcg   7620
cccaggctgg agtgcagtgg cacaatctcg gctcactgca acctccatct cccgggttta   7680
agtgattctc ctgcctcagc ctcctaagta gctgggatta caggcaccca ccaccacacc   7740
cggctattat tattattcct agctataaga atgctgtaga gatgaataca ctgtcagtga   7800
gctaggaggt catcctgtgt atccatcact tgtgcactca gtcgttcagg cgctatttgc   7860
tgaacaccaa ctacatgcca ggtgccatgc taagatttgg ggacacagtg gtgaccaaaa   7920
cagacagaaa ccaaggagct ggcttacatt ccaagggagt gcataggaag ctgtgtttca   7980
tttcagtttc tgctctagta cccccctttc cctggcagtg ccagggtctg agaaggaaga   8040
gtgaggtggt gaggaggtgt gaagcagtgg ggtgacctga gaggagagga tggggtggct   8100
ttgcctcaag gcttgggccc ctgctaggtg tcgctctgcc tcaggcctct gtttctcctc   8160
ctgacacagg cacagactcg gcctcccacc ccttccccaa ggacatgacc ttgggaagga   8220
acatatctga agcccgcgga gggtttccgc tgctgtgcat ctgtgccaca gatccgcaga   8280
tgcacccaca gctgggagca ccggttcctc ccgcctacct gcactccctg gtttctgttc   8340
cttcctcctc ctccttcctt ctccccgctc cccagacagg ctggtgatga gctttataac   8400
atgaaagctg atatttggcc attatccttc taccctgatt gccagctctt ctcagagtgc   8460
cttcttctgt aatccaatct ttgcaccagt ttccctgtga aactgccagt tttctgtata   8520
ggcctctgcc ctctccttgg ctcttctctc tggtcagtga gctttgtcaa ggggaacaca   8580
gggcttcctg gacacgtaat tcctcccact gaggaggaag gggctaatca ccagccctgt   8640
tttattttat tttatttttt tgagatgaag tctagctctg tcgcccaggc tggagtgcaa   8700
atggctcgat ctcggctcac tgcaacttct gtctcccggg ttcaagcgat tcttctgcct   8760
cagcctcctg agtagctggg gattacaagc atgcaccacc acacctggct aatttttttgt   8820
gtttttagta gagatggggt ttcaccatgt tggccaggct ggtctcgaac ttctgacctc   8880
```

-continued

```
agctgatcca cccacctcgg cctcccaaag tgctgggatt acaggagtga gccaccatgg   8940
ctggccgacc ccatctctta aaaaaacaaa aagaaaagaa aagaaaacaa aacaaaaaca   9000
ctttttaaat taactgatta tggtggcatg tgcctgtagt cctaactact caggaggctg   9060
aagtggaagg attgcttgag cccaagtagt tggaggccac agtgagctgt gatcacacca   9120
ctgtactcca gcctgggtga cagagtgaga ccctgtctca ggaaaaaaaa aaaattactg   9180
agaactctgt gaccatggca ccatgaacta tagaaagggc taacagttgg ctttgaaatg   9240
tgggttatgg ctgggtgcgg tggctcacgc ctgtaatccc agcactttgg gaggccaagg   9300
tgggcagatc acaaggtcag gagtttgaga ccagcccggc caacatagtg aaacctcatc   9360
tctactaaaa atacaaaaaa ttagccgggt gttgtggcag gtgcctgtaa tcctagctac   9420
tcgggaggct gaggcaggag aattgcttga acccaggagg tggaggttgc cacaagctga   9480
gatcgcacca ctgcactcca gcctgggcga cagagcaaga ctccatctca aaaacaaaaa   9540
taaaaacaaa aaaaagtggt ttgttttctt ttctttcttt tttctttttt tttttttttt   9600
ttttgaaaca gagtcttgct ctgtcaccag gctggattgc agtggaggat ctcagcacac   9660
tgccacctct gcctcccagg ttcaagtgat ttccctgcct cagcctccag agtagctggg   9720
actacaggca cgcaccacca cgctgggcta agtttttgta ttttagtaca gaaggggttt   9780
caccatgttg gccaggatgg tctccatctc cctgacctcg tgatccgccc acctcggcct   9840
cccaaagtgc tgggattacg ggcatgagcc accacgcccg gcctaaaagt gggttatttt   9900
ctaattgctc ttccctgatt aaaattttct ctttgcccat cttttctcta gatatgtact   9960
gacttcattc atccatttat tcgtctcact tgctcattca tttttgcttt catttactct  10020
actttgttga ataatattta gtgatctacc tgctgccagg cagtgagagt ctgaagtgaa  10080
caggatgctg ctttgccctc tgggagctta cagtgtagct gggaaccaga catccaaaca  10140
agcagaatat tatgcaaaag aaatgtcagg atgctttgga atcacagagg agtgagaaat  10200
ccctcccggg gaggctggtg aaggctttga agaggaagtg acatttgagt ggagtcttga  10260
agactaggca ggattctcca ggggccctgg gtgtggggga agcacacatc ctcttccctg  10320
taggaggtgc tgtggagaac acctccagtg gggctgctac tcttcagcct tgctggggcc  10380
agctggagtg gccacaccat ggtcacacca gctgaagttc aagaagcccc ttgccaggag  10440
attgctttgc tggctctggg tgagggcagg tgcatctgga agccccccttc tttctaagat  10500
gtttgctcct gagtttctat gtcctagtct tttcttccct gaacctttttg ctaccagtca  10560
gcacagccct gcctgagaag gaggctggag gagtgagtgg tcagtagcct ggtgggtctt  10620
ggctgcctct gtggtgcccg ctggcctaag tagcaggctt agggaggcga gacccagttc  10680
caggggctgc caatggggag cgagatgggg tggctggagc acactgcaca tgtcaccaag  10740
gctctaggga ggtctgtgca caaggcagtg ggaaaagcaa ggggaagacc cagcctggtc  10800
aacatggtga aaccccgtct ctactaaaaa tacaaaaatt agctgggtgt ggtagagcac  10860
gcctgtagtc ccagctaact tgggagcctg aggcaggaga atcactttaa cacaggaggt  10920
ggaggttgca gtgagccgag atcgtaccac tgtactccag cctgggtgac agagtgagac  10980
cctgtctcaa aaaaaaaaaa aaaaaaaaaa aaaaagtggg gaaggggaac actgatcctg  11040
attatctact ccatatactt actatgtacc tactacctac acagggacgg tgggctttac  11100
gcatgccatt tattcagtgt atagagatct cagcatcaca taggagcagg gagttctgaa  11160
gttggccttg ctggcatttg agaagtttct tggtgtattc ttcaggttca cgcctccaga  11220
```

-continued

```
caagtgtaag tgctattgaa tgctgactat gttccaggaa ctaaaccaga tgctagaaga  11280
cacgcagtaa acagtacaga tgcaggtgca catgtgaggg tccacacaag acctgagaga  11340
agggaggggt cttgctgcag ttccccttttt gtaacaaagg agagagtact gttgaccctc  11400
ttcctaggaa ctgtgagttt gactgaaatg tgtcctgcca caggatcttt gctgcttcct  11460
ctacctgatt ctttggatct ccctgctggc accttcttgt catttaggtc tcagctcaaa  11520
tgttacctcc tttaaaatgt cttctctggc cagccagtct aaggttgctt gtgcttgggg  11580
tctcctcact ctctacttta tcccgcagtt gcttcttatc acatatggct ctctgaaatt  11640
aggtattcat tacttacatc tgtcttcccc actagaatta agctctgatg acaaggatct  11700
ttctgtgctg ttcatagctt atcttctagt acctggctta gttcctggca cattgtaagc  11760
attcaataac agtttgaatg aatgaattaa caaatgaagg aatgaatgaa tgcattttcc  11820
tagaggactt ctgttcttcc ctgagggaag ttataggtcg tattggtttc ttgggactgt  11880
tttttgtttg tttgttttgt tttgtttttt gagacagagt ctcactgtat cccccaggct  11940
ggagtgcagt ggcacaatct tggctcactg caacttccgc ctcccaggtt caagcgattc  12000
tcatgcctca gcctcccgag tagctgggga ttccaggagc ctgccaccac gaccagctaa  12060
tttttgtatt tttagtagag acaaggtttc accatgttgg ccaggctggt cttgaactcc  12120
tgacctcagg tgacctgcct gcctctgcct cccaaagtgc tgggattaca ggcatgagcc  12180
accacgcccg gcctgttttt tttttttttt taagacagag tcttgcactg tctcccagac  12240
tggagtgcag tggtgtgatc tcagctcatt gcagcctcaa cctcctggcc tcaggtccag  12300
gtgatcctct tacctcagtc ttctgagtaa ctgggcccac tggtatatac caccacacct  12360
ggctaatttt taaatttttt gcagagacat ggtctcacta tgttgccctg actgatcttg  12420
aactccttgg gttcaagtga tcctcacacc ttggcttccc aaagtgctgg gtttacaggt  12480
gtgagccacc atgcctgggc ttgagactgt taagatgatg aggctggagg gagtggatgg  12540
cctcactgct tgagccctag agattcctta ctccagagtg ccctggctgc agaggtggcc  12600
ctggagggtc actccagcaa cctggctgag ctgatgggca tcatctgata ccagctctga  12660
ccctgaataa taggcaacat ggaccttagt ctaaagcact gacccctcat ctctgcatat  12720
accaaagaag atgagatttg ggtgaggaca cagccaaacc atatcagctc ccgggatccc  12780
tgtgtgaatg gggtcttttt tggtgtttga gggctgcaca gggtgacctc tttagaggtg  12840
acctcctgcc acaacccaca ggaggtgcac atggcccaca catgctggtt tcctgcagtg  12900
ggaggggctg gggcactcct gggacctgtg cttggtaact ggagctggcc tggccctggg  12960
gattgggtgt ctgccttggg tttcaggtgt attaggttgt tcctcgttgt ggagtctcat  13020
tactaatgaa aagttcaggt cgcactgctg gtcctttggg ctgtggttga tcctggtgat  13080
aacatttggc acccagaggc agccctgttt ccactgaagc atgcggagct tggctggcag  13140
gcaggcaagc tggcagctgc ccttaaccca tgaggtgctg gcccgctagt aggcacaccc  13200
tacctgtgcc agaattgagg ttgtagccag actccaggag ccatctgggc cccacagggg  13260
gcggcatttc ctctttttgt tgaaacattc cagccaagtg ctggcttggg cttcatctct  13320
ctgtcccact ctccttcctc tccccaacat aagcctcctt ctacatccta gagctctttc  13380
cattccccct cctgcagctc tgggctcgct aatctcatgc ttccctaagg gagcttgacg  13440
gctgcttctg ctaacattta ataaagttct gcgtgccaga ccctgtgtta tgggttttac  13500
accttatctc acaatcttaa aaaaaaaatt ctctgagaat cctctgtcac ccccacttta  13560
caggtgagga aactgaggca aagataggct aactggcttc cccaacacca tgcaggtaat  13620
```

-continued

```
tagtgataaa ggcagggttg gaaccaaact tgacctccca attgtgctct taatggccag  13680
gacactctgt gtcttgagcc acacttcctc catgttttct agggctttct agggaggcag  13740
acagtgatgg gaaggggtgt tctttagtgt ggatgtgccc tgcctgctcc tttctgtaag  13800
cgtcacagca cctccactgc tgtactgggg aggcaccaag tttttccctg tttgcccacc  13860
caaggcgagc tagcttagga gtcacgtgag tgctgggtgt ctcgcctgct gcatccctct  13920
atcctgcccc tgcccccggt gcccagagga gggccctgcc tgtcttccca gttctccaac  13980
agcagcgctg tcccagcacc ctcgggctcc agttgtggcc tggcagctgc tggggcagac  14040
accatacaga cagagtcaca gcaggaagag gatggggccc agggctgctg cctcaggcca  14100
tggctgcatg gcaccatcag ttgattgagg agcttttctt gccaatgtct gaggcatcag  14160
gtggcaggac acgtctccct gctcttaagc ctcaggcatg cagcccttct tatgctctct  14220
ggggtgaggg ggagatcccc ctcatggaat tgcttttttt tttttttttt tttttttgag  14280
acagggtcct gctctgtcac tcaggctgga gtgcagcctc aacctcccag actcaagtga  14340
tcctcctgcc tcagcctccc gagtagctgg gaccacaggt ggacaccatc acacctgggt  14400
ttttttgttt tttgtttttt gttttctaga gatggggtct cactttcttg ctcagtctgg  14460
tctcgaactc ctgggcgcaa gcagtcctcc cacctcgtct tcccaaagtg tttggattac  14520
aggtgtgagc cactgtgctt ggccttttta tttatttaga atttgttttg gaattgcttc  14580
tttatgcctg gcactatgct ggcactatgt ggcagagatt ttaaaaacga gcaaacaaaa  14640
caaatgcttt gtcaaccaca aaatgtattc tctgcccctt aggttctttt tgtgtagttg  14700
aggctagaag acaaaaatag gggcagtaa ggagcaggga gcgatggttt aggaggtctt  14760
ccttccagcc cccttgttga agcatctggc tcactagctt gggggagcca ttaggcagca  14820
gtggccaatc ctgaggcact ctcaggtgtc actaagaaaa ggggcatgtg ctctatggat  14880
acccatgggc tgaacttgga gtctggtctg gacccatggc tgtgctagga tccaccgtcc  14940
ccagccccaa ctgcagtcag catgttcatc atccttaggc ctctccgctt ctttctgcat  15000
gtttgtctgc ctcatgccct gctcattacc aactggtcag tccccactgc cctgcctgga  15060
gtgagctggt ttgattggct tagctaagct cccttgcctc tgctggccag gtcaccctgt  15120
gggtcaccag caaacctgtt gatggtccag tctgaacctg cttctccaca aagaacatgt  15180
tgcacccagc cctgcttctc tgagcagagg tttggggctg agctgttcta gccagaaagg  15240
gacacagggt gtggcaggca ccatgatggg catatctaat gtgccgggaa aaacaatgag  15300
ctgctctccg tgctttgggc acctggttgg gagagggccc atctgtctga ctttctcctc  15360
ctggggctct cagcgtctcc gagaacctct gccagagctg tgtagaagtg gtttgcttgt  15420
ttcttaacac ttctgtgccc tatttctttc tgtacccaag aaaggaagta gactgttttg  15480
tagggacact gtcggggtga tgaatctgga cttactggaa tcatgaacca tgccaaggag  15540
gaaggagaaa ataggctatg gtgggtgtct tagttagggc tggctgctgt aacaaaatgc  15600
ctttagctga gtaatttaaa gcaagagaaa tgtattgctc agagtttggg aggctgggaa  15660
gtccaagatc agggtgccag cagattcagt gtctggtgaa ggctgatgct ctgtgacaaa  15720
ggtggcacct tctagctcca tcctcacatg gcagaagagg gaacaagctc cctcagacct  15780
cttttctaag ggcgttagtc ccatgcatga gggctctaac atcacgactg agtcacctcc  15840
caaagccctc acctcccacc agcactgcac tggggattaa gtttcaatat gggaattttg  15900
gaggaacaca gaccttcaga ccacagcagc gggcttctcc tcatgtgccc cctgcctcac  15960
```

-continued

```
ttctagatgc cgcataatgt cagtgaaacc ccgtctctac taaaaataca aaaaattagc  16020
tgggtgtggt ggcacgtgcc tgtaatccca gctacttggg aggctgaggc aggagaatcg  16080
cttgaaccca ggaggcagag gttgcagtga cctgagatcg tgccactgca ctccagcctg  16140
ggcgacagag gaagactccg tcaagaaaaa agagaaaagg catcaggtat gccagggtgt  16200
gcgggaaaag gcatcgggta tgccagggcg tgtgggaaaa ggcatcgggt atgccagggt  16260
gtgtgggaaa aggcatcggg tatgccaggg catgtgggaa aaggtggtaa gattcctcag  16320
cctcccaggg ttgggaagcc tctggccgag tgaagcatac cctgggtggg ttttaagaca  16380
ccagctttcc agtccagctc agctgtggga tgtgggaaca tgagtcagtg ggaacatgag  16440
aattggcttc cctgtggctc acaataatac ctactcctgc ctacttcatg ggacccgcat  16500
aagagctgag ggattccata gctcaggggt atgctgtaaa gacaagcact atgcacctgg  16560
gtgtggttct gaaactttct tgtgcagaag agtgagtagg gctgggcgag tcctgagaat  16620
gtgcatttct cacacacctc tgatgctgct gatgctctag tcccttggct ggcaagggta  16680
cctggttagt aggggccagg actctgtaat gccttccact tcagggttct ctgggctggt  16740
tttcctgact ccccaggaag cctttattca gcagagggaa ggtaggagtg agaggactac  16800
gctgtcagtg cttcacatac atcgtttaat ttatcccagc acagccctta ggagggaagc  16860
agtattctcc ttctacactt aagaaaatcg gcctggtgcg gaggctcatg cctataatcc  16920
cagcactgtg ggaagctgag gcgggaggat cgctggagcc caggagttca agactagtct  16980
aggcaataca gggagacctc atctctacaa aaaaaaaaaa aattagctgg gcatggtggt  17040
gcacacttgc agtcccagct acctacccag aggctgagct gggaggattg cttgagtcct  17100
ggaggatcga ggctgcagtg agctatgatt gctccactac actccatccc tggcaacaga  17160
gtgagactcc atcccaaaaa aaaaaaaaaa ttgaagctag gagaagttga gacttgcctg  17220
aagttacaca gtaagtgcca gaaccaggac ttggaccagg tctttctgac tccaggccaa  17280
tggatgtttc ttccatgaca tatatagctc ttgaaactac ttctatctaa tatcacccac  17340
agtgctgtta aaaatacaga tttctgggcc tcaccctcaa attatgattc agtaggtcta  17400
ggcacgtcaa ggtcattgtt tttgtctttg ttttaagtca ccccaggtga ttctaaagcc  17460
gaagctctgc aaagcacacc ttgagaaaca gagaactctt gtgctctcgc tctcttgaca  17520
cttcaggtgc aaaacttttg tcctaatgtc gttctcaaac ttacgcatgt gtgagaatca  17580
ctgtgagagc ttattgaaac tgattgcggg accccatacc tagagggcct gattctatag  17640
gtctgaggta aggcccaaga atttgcatat ttgcatttcg ttttcttttc ctttcttttc  17700
tttttttttt tttttgagat gaagtctcac cctgtcgccc agactggagt gcagtggcat  17760
gatctcagct cactgcagcc tctgcctcct gggttaaagc gattctcccc acaccccaga  17820
cccgctcctg agtagctggg attacaggtg cccgccacca tgactagcta acgtttgtat  17880
ttttagtaga gacggggttt tcaccatgtt ggccaggctg gtctcaaact cctgacctca  17940
ggtgatccac tcacctcagc ctcccaaggt cttgggatta ctggtgtgag ccaccgcgtg  18000
cggccagaat ttgcatttct aacaagtccc aggtgatgct gatgctgtgg gtccagggac  18060
acactttgag aacagcttgt tactcaggcg atatgtggac agtagcgtca tcttcacctg  18120
ggagcttcct gcagcatctc aggccttgcc ctacacctac cagatcagaa tctgcatttt  18180
aactcaatcc ccgcgtgatt ctcatgcacc tggaagtttg agaaatatga ccttagagga  18240
gccggaatgt gaaaccactg gaggcagaga tagatggaga atatctcttc ttctcacgga  18300
tactaaagat gcaacaaaaa gggctgactc tctgggtgtg cacccaggtg ggctgatga  18360
```

-continued

```
ccgaaaagag gccagatgtg gacagaggac tcttccctga gggaaggcag agagaactta  18420
ggaaaatctg aagaaaggag gtggcttcag aggaaaggca ttcatctggg ccataaaaca  18480
gtggagaagg tatcctgctg agagcacagg ggtggggagg gggtgccctg gagctgaagt  18540
cttcagtggg gggacagtga taggtgaaca cacatgtgaa taaacagttt gctaagcagc  18600
tgcgagggct ggccaaggtg agaaagcatc cgtctgcaga ggcctcaata aggccagtgt  18660
gttgactttg tcctgcagtg ctcagcagtg gaaaaaacca acagccacgc agggagaggg  18720
aaggagccac gatgggcacg ggttactggg gccagggctt gactggtagg tggacacagc  18780
tgaaggccca ggttgtgtgg gaacagagcg cagaagcaat agattcctct tgaagatcct  18840
tgggctgtta accttttttta aatttaagag aggttgtgtg ggcggggagg gaggaaggaa  18900
aatccttcag aagacataga cttactctgt ttcttccatc atatgtgaat gcatatgaat  18960
agccaaaagg tgaataaaac acatgttccc aggtggccag tgagacctag gttgcaagat  19020
ggtggggtgt gtgtgaggcc ggggagtgct gcgagccccg gaattcctca gccttagtcc  19080
cccgccacat agctaagaag tgagggagga ggtgagaagg agtcactgcc cagcctcact  19140
tccggtggag taccctgtct ccttgtcagt tctgtctctg gggacagttg cctgctttca  19200
cctctccctc catcccctct tctctcacag ggaaaaattc accttaatat tggaagttcc  19260
tctcctagca aagtccttct caggcaccca caggcaaaaa ggaaactaag cagagttagg  19320
gcttccaggc ctagccaact acacgactct cctcttgctt ccctaagaac cagcgcaagg  19380
ggcagcgtgg gttccagcat agatggacct gtgttggaat ctctgcacgt gctgtgctga  19440
ccctggctag ccattgacct ctctgagccc ttgtttcctt tccactaggc tctctgaggg  19500
caggggccat gtctttttca ctgctctgtc tgcactgagc actgtgcagg gcacatagga  19560
agttcccata aatgtttgtg ggataaagga aataaaacct tctctcttcc tgtccccctt  19620
gtgatggctt tgcacaaggc actgtccttg gccaggtttg ctaggctagt gtgaggataa  19680
accaggtata ttacaaattg gagaaaattt ctcgttcttc ttggaagaag gtgctgtatc  19740
atgaaacaag aatgtcttga ttcccttcta tgccaggtac tggggagaaa caggtgcctg  19800
ataaccgttg atccaggcag aaataagcat actcctgctt cccaaggcct gatgcttctc  19860
tccttcctcc cttcctccct ccttctcttc actctttctc tgcacacatg gaagaatggc  19920
tgccaggcat tgcccatttg gaaaagtaca gctcaatgga tatgaatcag cttgggcagg  19980
cgagaaatga ttcacgtctg accaaatcga tttagttcag gttgcccgtt ctgcatcttt  20040
tttcccttgt aattaaatga tgattggtct tgatggtggg aaggaagaga cagaatttaa  20100
tttgtttgcc tttgtagaaa gctggggaca gcacagataa gggaagatgt ctcccatttg  20160
gcaaataact gatgcggagg tggagtggca gtggtgatgg ggatgctggt gccttcaggc  20220
cttctgggcc gggcagtgca gctggtggca gacggttcgg aactctacca tgttcccatc  20280
tgaaaactgt ggctgatcat gcccactcct gaccttgctc cagggagtac acaaagacgt  20340
aagcttaatt aacccaccag acgtagctct tgaatccctg ggcatagtgc ctgggtatag  20400
ttagagttgg ggagaggcat ggtcagcaaa acaacctccc tcatctctct gttgtcactc  20460
agagtcaagc tggctgctgc tggtggtgct gacttctctt gctgcagatt tctccaatat  20520
gtttctgccc tgcacgcatt tgccaaatcc cttcggtttc ttgtgtctcg tggcagctta  20580
gctcctccag cccttggatg aagaagcgtg ggaactcttt gcttcctttc cctcccgcag  20640
tgacatgcca tgccatgcca ctgcctcttc atctggtcct atgacagtca ctcataagca  20700
```

-continued

```
cccgcatgta cccggccctg cactagctca tgacagctgc agtcaattgg gccaggtgct  20760
gtatctcatc cggcctcctc agcaaccctc tgagatactg gtaatgtccc tgatgaagat  20820
atttactgag gcagaaatgg acgctcagtg aagcaaggtg cctgatgtta tagcaatgag  20880
ctatgagtgg ccagagggag gagataagct caggcctgac accaaagccc atgctccttc  20940
tagtcaacca cagtgcctcc tatggtgaat gagtgagtca gcaaccaaga cgcatgaggc  21000
cttctttttg gtgagccttg gctgggtgct gaggcttcag gtacaatcat gggttggaag  21060
agccctcctc tctctccaca gtctggcact atgacccctt ctggttatta acaaggcaaa  21120
gagagagagg gaagaaagca ggcaaataat gtgggttgct attcctagag attagaattt  21180
caggaaggat aaacacagcg ttctctccag aagtataaat aggaagactt cacacatgac  21240
tagaacgaga catgttttaa gtctgtcgag taaggcagtg atgaagtaga tttccccaga  21300
ttcactctcc ctcctctggg tcccccaggg cctttacttg tggcaacttt cagctcaggg  21360
agggaggaaa gccccttca aagcttcaga tacttcctta aggtcagttt ctgcttaaag  21420
aaggccttta cattacttca tccctttgcc aaattaaact gaaaggaaac ctttcaagtg  21480
tgattgcctg gccctttcct gttcatttct cgtgggtacg ctttctaact ttctttcttt  21540
cttcctttct tcaggtgttg actttaagat gaagaccata gaggtagacg gcatcaaagt  21600
gcggatacag atctggtgag ctggggagga ggaggaggca gatgtaggag aagaggactt  21660
ctggctgctc cttagctgcc cctgccatgt gtaaaattcc taggcttcac ctgggataac  21720
tggccacctc tctgatggat ggaagcgaag tctcagaagc ccatctcttc ctataagcct  21780
taatctccaa cctctaagaa actttagggg attgactaca agcaccaaag ggcaggaatt  21840
agaaggaact ggcacactaa ccattgtgaa tttatctcag gattaggctt tgcccttggg  21900
ctgtgccaca ctatgttaag attggaagga aggaggctac accccccatc atttagggcg  21960
agaccctgag agagttcctc aggatagcat gatgaagttt ccacagtagc agagggtgct  22020
gctgtggctc tctgcctgag gtcttggaag cactgccttt gccagggttt agagctccct  22080
ctcaattcca cagcagtatg ggcactgcct tcagaggtcc catagggact aggggtgtag  22140
cagcatcccc tgccaactcc catccaacca aatctggcca cagtggccag attccagaga  22200
gctgtccaag gcctgttctg gctgtggctt ctggtttctg ccaggagggc agttggcagg  22260
aggggccaag gccctgcagg cctggtcagc accagcacag atgaccaggc ctctgactgc  22320
agatccctgt ggggatccaa gcatccctgg tttttcaccc tttagctccc cagtttttcc  22380
tacaagggga cagctctgct cttcccctcc ccgtctgttc ccatggtccc tgctcctctg  22440
agggactggc tttctcctgc agggacactg cagggcagga gagataccag accatcacaa  22500
agcagtacta tcggcgggcc caggtaagcc accacattgg gggtttcaaa gtgggaagct  22560
gccacccaca ctcccagctc tgggtatttg agatgtctgt gccacggatc ccctaaatac  22620
agttcgcctg cttggaggag cgcagggcgt ctttcagctg ttcactgatc atttgtccgt  22680
ccattgttca tggcccactc actgcaggca ggcccctgcc ctcacccctg acttccaccc  22740
tccatcctgg gtcaaagatc caggtcaaag catgtggtgt cttcctgctg tagagagttc  22800
tgtgatgggc ctgggaggcg gcagtggtgg ggtctgagag aagagatatt tctggatgct  22860
gagcagggag aatgggagag tgggacccaa cctttaagtt tccacggccc cttctggccc  22920
catgactgca ctctctctgt gcatatcaca tctctctatt tctctctctc tcaggggata  22980
tttttggtct atgacattag cagcgagcgc tcttaccagc acatcatgaa gtgggtcagt  23040
gacgtggatg aggtaggaga tgccacctca ctgccggggt gtggagaggg tgcctcaccg  23100
```

-continued gggaaggcaa ggcgagggcc agatgggaag gcaaatgctt ccaggaagct ttgccttcca 23160
cagccctgga tgaagacctc tgggtgagta agacatgggg aagaaaccga agctgccatg 23220
ccctcactct ctataccctg ccaggcctcc acggctgtgt ctttcccgga aatgaattag 23280
ttccaagtct tccctgtgag cagcttcttt cctgaaatct tgggaccagg tggagttgca 23340
agattgggat ctagtcctgg ctctgcacaa tagctgtgga gccttgggaa gccatttgaa 23400
tcctctgggt ccccagttcc tgtagaatga gggctggact tacatccaat gtcctttcca 23460
gctctgatac cagtggtcta acccaaggaa gcaccagtct tagccagagt gtcttctacc 23520
ctaagctctc cccgtgatac ccttgaggtc agccatggca cttgggggag cctggcacct 23580
gcatccagtc ggcccaccct gtccctaggg ctctggaatt ggtggtgggc tggaggcagt 23640
gcagactctg tagggaaaat tgggggggca ggcagcactc actggctgtt ctgcccatcc 23700
tttgtcccta gtacgcacca gaaggcgtcc agaagatcct tattgggaat aaggctgatg 23760
aggagcagaa acggcaggtg ggaagagagc aagggcagca ggtaagtgga gggaaaaggc 23820
aagtccaccc caggtcctct gctgggcctc cagggccagt cctgagcgtg gggacctagg 23880
ggtgtgttcc ccagtggcag gtcctcccac acgtccccag caccccaagg ccctggggga 23940
gtggccatcc tcggaaggct tgttgtctgg gtttcaggac agaagcccag agattcgggg 24000
tccatccaga aacaaagacg tcataggcag caactctccc aagtccaggt ccccaaatgc 24060
aggattgccc tctgcttaag agatcatccc cgtgttagta atgaaggact tcaagttgtc 24120
aacctcttct ctgacagcat ccaggcctag ctgccatgtt acggtcgaga aatgatctcc 24180
catcccaccc aacactcccc cactcctgtc cttcttaccc aggaaagagc cagggaggca 24240
aatgaggaga caaagagcca cagctggaga agccatgggg gcagaaaggg taggaggatg 24300
acgctgaggg aatgtccaag catgcaggga gaccatcctc ccagagagca gaaagaaata 24360
ttggttattt tttttttctt tctttctttt tttttttttt tttgagatgg agtctcgctc 24420
tgtcacccag gctagagtgc agtggcgcca tctcggctca ctgcaacctc tgcctcctga 24480
gttcaagcaa ttcttctgcc tcagcctccc aagtagctga gattacaggt gcatgccacc 24540
acgcctggct aatttttttg tatttttagt agagatgggg ttttgccata ttggccaggc 24600
cggtctcgaa ctcctaacct caggtgatcc acctgcctca gtctcccaaa gtgctgggat 24660
tacaggcgtg agccactgtg cccagccaag attggtattt ctgagataag ttatccactc 24720
agtccgtgga cctcaagagt tttcctctcc cttttcagtc aatagcgttc cattagtact 24780
taaaatgaaa ttgattgttt ggtataaaat ataagacatg gtcattgacc aatttgaaag 24840
tagaggcaaa gcctactagg atagtattta ttgagcactc tatgtgtggc actgtgctaa 24900
ggcaagcgct tttaagtgca cgaccccact gaatcatccc acaaccatgg atgggagaca 24960
cactcagtct cctttaacag aagataaagc tggggcttac agagaatgta caacttgtcc 25020
aaggtcacac agctagccat cagtggcagt gctgctattc aggtctggga ctgtgggact 25080
ccagagccca tgttttttac gaggatgcca tactgccaca atggatggtg tctttatctc 25140
ctgatatatg attgtgtgtt gggaggcgtg gggtggcagc tggaagaatg gagaggcata 25200
tttgtggagg atcttccccc attctctgct accctctctt ggagctccca gtcccatctg 25260
agaaattatc tactctgaga aatcgtcaca acacagcatg gttgtgagtg cagtggcaga 25320
agcctgtgcc tggttgtatg ggcccctccc ctgccttact gactctcttt cagaaatgtc 25380
cttctcttgc agctggcgaa ggagtatggc atggacttct atgaaacaag tgcctgcacc 25440

-continued

```
aacctcaaca ttaaagaggt gagagccctg gtgaccaggc gcccgctctc tcgggctgag  25500
tccagcagag gtgggaggag gagccataag atggacctta tccctcaggc cgctgcaggg  25560
ttgccagggg agaggaggag acactggact aacctgtgcc ctttggtttc cagtcattca  25620
cgcgtctgac agagctggtg ctgcaggccc ataggaagga gctggaaggc ctccggatgc  25680
gtgccagcaa tgagttggca ctggcagagc tggaggagga ggagggcaaa cccgagggcc  25740
cagcgaactc ttcgaaaacc tgctggtgct gagtcctgtg tggggcaccc cacacgacac  25800
ccctcttccc tcaggaggcc cgtgggcaga caggggagcc ggggctttgc cctgctgctg  25860
tcctctcgtg tgatgaccct attgagtatc agtagccact actccccctg cctggccctg  25920
agagcggctc tgctgtcatc tcaagcagcc cctgtcccca gcccgtccac cctggagtgg  25980
tcttcttcag cctgtttccc cagccacagg cctgctacga cccccacgat gtgccgcaag  26040
cactgtctca ccatcccgca cccaccagac aacagccagg gctggagtcc aggccacttt  26100
cagctgctcc tttctccgtg catcgtgtct cttctctgct tttctctctt tcccccactt  26160
ctctttctct gacccctccc ctccggtgcg tttcgtatca aagctcctca aaccccgtcc  26220
cccgtgtgtc ctgctgtgtg cagctcgctc tttccttcct tcctaagcta tccaagggga  26280
tggacccagg ctcgtgggga ggttccaccc ttggatccag gaagaaccct ccaccctgcc  26340
tcgtgggtgg gccaaaggct acagggtgct tcttcctctt cccccacccc cactgtccct  26400
catgtgccat gggcctgcct ccccagtgac ctgcgaaagt ggagcatcga ggtaggaggg  26460
aaacggcaac cagggagtcc tcgagcctgg ggctgcccta cctctaccca ttccccgacc  26520
agagctttgc ccttgcttgg ctgcccgcct gcctctttgg ggaactgagc tcagaggcag  26580
gtgcttcaga gaaggaaaca aaatgagggg tggcagggat aaaaagtcac ctccattctc  26640
tacctcccat gcagcatgaa cacaatttct ctccacctgg ctcccaaatt taaagatgtg  26700
gaccaaggcc tgtgggtact ccaggggcaa ggagagccct ggggtcagtg acactgtcag  26760
gccaaccatg cactccacaa aggggagcat ttggaaatga aggactagct cctatgtatc  26820
aggttaagag caagggagag ctggccaggg acagcagttt gcacagcaga ggggaatgta  26880
gcaacagcag ggcctcctag gccccatctt ccatttctta ggtaagaaga gcatttcctc  26940
agactcccag gcggaggact gagcctagcc ttcagcaacc aaggttctcc tgggacccaa  27000
agtttatggg agaagggcaa agacttcatg ggaagagaga aggaaggccc tgggtagaaa  27060
cgcttggtgc tgttctcttt ggcctttaag acaaagcgct catcttgccc tctacctcct  27120
gataggcttg agggtttgcc aaccacactg tggctacagg tggagggaag aggactcctt  27180
cctccagagt gctatgttca ggaagtttct ttaaccccat atggcccaag agtagctcgt  27240
aggaggccct ttaaagacgg aacaagtaat ttaccagttc tactggggtt cctgcccacc  27300
gtcccaaggt gggcgaggcc taggaagagg gtcattctta agccacacat tagctgcact  27360
gcgtggctgc agccaaaaca aagaactggg tgttgagtat tcatcaacta agaaccaaaa  27420
tccagggcac tcatatgtga aggataagaa cctcacttcc ttactcctcc aaaaagaagt  27480
ggggaaagaa ccatcaaacc tttcctcctg acttaccaaa ccaggaaaac agcaggagag  27540
ggtggctcag gacttaggga cagggtatag cttagatggt ggaaagcaaa ggagagcagg  27600
aagttgtaaa tcactggcta atgagaaaag gagacagcta actctaggat gaagctgtga  27660
ctaggctgga gttgcttcct tgaagatggg actccttggg tatcaagacc tatgccacat  27720
cacactgggg ctagggaagt aggtgatgcc agccctcaag tctgtcttca gccagggact  27780
tgagaagtta tattgggcag tggctccaat ctgtggacca gtatttcagc tttccctgaa  27840
```

-continued

```
gatcaggcag ggtgccattc attgtctttc tctcctagcc ccctcaggaa agaaggacta  27900

tatttgtact gtaccctagg ggttctggaa gggaaaacat ggaatcagga ttctatagac  27960

tgataggccc tatccacaag ggccatgact gggaaaaggt atgggagcag aaggagaatt  28020

gggattttag ggtgcagcta cgctcaccct aaacttttgg tggcctgggg catgtcttga  28080

ggcccagact gttaaccagg ctctgctggc ctgtttactc gtcaccacct ctgcacctgc  28140

tgtcttgaga ctccatccag ccccaggcac gccacctgct cctgagcctc cactatctcc  28200

ctgtgacggg tgaacttcgt gtactgtgtc tcgggtccat atatgaattg tgagcagggt  28260

tcatctattt taaacacaga tgtttacaaa ataaagatta tttcaaacca ccggtgtggc  28320

tgcctggatg agtccttggg ggtaggtctc actcagaccc tggcagtgat gtgggaggga  28380

gagaggcagt gctggtagaa gcagctccag aagcaaaggc aacagcagta gagtgaccac  28440

ggaagcggca aacattgtct tcccttctct accttcccta gtgccacctg cagggaggcc  28500

caaagcaaag ccccgttgcc ctgcattggg ctggcactgc agaaataaga tgaaacacag  28560

ttatcgagag gatgctgaac atctatgagc aggttttaaa gccaagatga gtctcatctg  28620

tttgtgtggg tcaggaacgg gtcttcctga aggcatgagg tgggactgga taatctttca  28680

gatttgtgat tggatacctc gggggagcag aggcagactg ggatctcagg actgcaggta  28740

tttcatactt tgggatatgg aattgatgga                                    28770
```

```
<210> SEQ ID NO 4
<211> LENGTH: 212
<212> TYPE: PRT
<213> ORGANISM: Rattus norvegicus

<400> SEQUENCE: 4

Met Ala Lys Gln Tyr Asp Val Leu Phe Arg Leu Leu Leu Ile Gly Asp
 1               5                  10                  15

Ser Gly Val Gly Lys Thr Cys Leu Leu Cys Arg Phe Thr Asp Asn Glu
            20                  25                  30

Phe His Ser Ser His Ile Ser Thr Ile Gly Val Asp Phe Lys Met Lys
        35                  40                  45

Thr Ile Glu Val Asp Gly Ile Lys Val Arg Ile Gln Ile Trp Asp Thr
    50                  55                  60

Ala Gly Gln Glu Arg Tyr Gln Thr Ile Thr Lys Gln Tyr Tyr Arg Arg
65                  70                  75                  80

Ala Gln Gly Ile Phe Leu Val Tyr Asp Ile Ser Ser Glu Arg Ser Tyr
                85                  90                  95

Gln His Ile Met Lys Trp Val Ser Asp Val Asp Glu Tyr Ala Pro Glu
            100                 105                 110

Gly Val Gln Lys Ile Leu Ile Gly Asn Lys Ala Asp Glu Glu Gln Lys
        115                 120                 125

Arg Gln Val Gly Arg Glu Gln Gly Gln Gln Leu Ala Lys Glu Tyr Gly
    130                 135                 140

Met Asp Phe Tyr Glu Thr Ser Ala Cys Thr Asn Leu Asn Ile Lys Glu
145                 150                 155                 160

Ser Phe Thr Arg Leu Thr Glu Leu Val Leu Gln Ala His Arg Lys Glu
                165                 170                 175

Leu Asp Gly Leu Arg Thr Cys Ala Ser Asn Glu Leu Ala Leu Ala Glu
            180                 185                 190

Leu Glu Glu Asp Glu Gly Lys Thr Glu Gly Pro Ala Asn Ser Ser Lys
        195                 200                 205
```

```
Thr Cys Trp Cys
    210


<210> SEQ ID NO 5
<211> LENGTH: 218
<212> TYPE: PRT
<213> ORGANISM: Homo sapiens

<400> SEQUENCE: 5

Met Ala Lys Gln Tyr Asp Val Leu Phe Arg Leu Leu Leu Ile Gly Asp
 1               5                  10                  15

Ser Gly Val Gly Lys Thr Cys Leu Leu Cys Arg Phe Thr Asp Asn Glu
            20                  25                  30

Phe His Ser Ser His Ile Ser Thr Ile Gly Val Asp Phe Lys Met Lys
        35                  40                  45

Thr Ile Glu Val Asp Gly Ile Lys Val Arg Ile Gln Ile Trp Asp Thr
    50                  55                  60

Ala Gly Gln Glu Arg Tyr Gln Thr Ile Thr Lys Gln Tyr Tyr Arg Arg
65                  70                  75                  80

Ala Gln Gly Ile Phe Leu Val Tyr Asp Ile Ser Ser Glu Arg Ser Tyr
                85                  90                  95

Gln His Ile Met Lys Trp Val Ser Asp Val Asp Glu Tyr Ala Pro Glu
            100                 105                 110

Gly Val Gln Lys Ile Leu Ile Gly Asn Lys Ala Asp Glu Glu Gln Lys
        115                 120                 125

Arg Gln Val Gly Arg Glu Gln Gly Gln Gln Lys Cys Pro Ser Leu Gln
    130                 135                 140

Leu Ala Lys Glu Tyr Gly Met Asp Phe Tyr Glu Thr Ser Ala Cys Thr
145                 150                 155                 160

Asn Leu Asn Ile Lys Glu Ser Phe Thr Arg Leu Thr Glu Leu Val Leu
                165                 170                 175

Gln Ala His Arg Lys Glu Leu Glu Gly Leu Arg Met Arg Ala Ser Asn
            180                 185                 190

Glu Leu Ala Leu Ala Glu Leu Glu Glu Glu Glu Gly Lys Pro Glu Gly
        195                 200                 205

Pro Ala Asn Ser Ser Lys Thr Cys Trp Cys
    210                 215


<210> SEQ ID NO 6
<211> LENGTH: 4
<212> TYPE: PRT
<213> ORGANISM: Homo sapiens

<400> SEQUENCE: 6

Asn Ser Ser Lys
 1


<210> SEQ ID NO 7
<211> LENGTH: 4
<212> TYPE: PRT
<213> ORGANISM: Homo sapiens

<400> SEQUENCE: 7

Thr Asp Asn Glu
 1


<210> SEQ ID NO 8
<211> LENGTH: 4
```

<212> TYPE: PRT
<213> ORGANISM: Homo sapiens

<400> SEQUENCE: 8

Ser Asp Val Asp
 1

<210> SEQ ID NO 9
<211> LENGTH: 9
<212> TYPE: PRT
<213> ORGANISM: Homo sapiens

<400> SEQUENCE: 9

Lys Trp Val Ser Asp Val Asp Glu Tyr
 1               5

<210> SEQ ID NO 10
<211> LENGTH: 6
<212> TYPE: PRT
<213> ORGANISM: Homo sapiens

<400> SEQUENCE: 10

Gly Val Gly Lys Thr Cys
 1               5

<210> SEQ ID NO 11
<211> LENGTH: 6
<212> TYPE: PRT
<213> ORGANISM: Homo sapiens

<400> SEQUENCE: 11

Gly Gln Gln Leu Ala Lys
 1               5

<210> SEQ ID NO 12
<211> LENGTH: 8
<212> TYPE: PRT
<213> ORGANISM: Homo sapiens

<400> SEQUENCE: 12

Gly Asp Ser Gly Val Gly Lys Thr
 1               5

<210> SEQ ID NO 13
<211> LENGTH: 14
<212> TYPE: PRT
<213> ORGANISM: Homo sapiens

<400> SEQUENCE: 13

Leu Leu Leu Ile Gly Asp Ser Gly Val Gly Lys Thr Cys Leu
 1               5                   10

<210> SEQ ID NO 14
<211> LENGTH: 506
<212> TYPE: DNA
<213> ORGANISM: Homo sapiens
<220> FEATURE:
<221> NAME/KEY: variation
<222> LOCATION: (206)...(206)
<223> OTHER INFORMATION: 't' may be either present or absent

<400> SEQUENCE: 14
gctcaagatt gcacagctgg tgagtggtga cactgggact ggaacccaag tgtgccttac     60
tccagagccc ttggcatgca cctgaaaccc catgtaagcc cactgtggag acgcgcacct    120

```
cgaaataatg gaatccacta catcagttcc tttagctttc tgtgtaatca gagtagctag    180

caggctcggg atttcgcccc ccggcttttt tttttttttt tttttgagac agagttttgc    240

tcttgttgcc caggctggag tgcaatggcg caatctcggc tcaccgcaac cttcgcctct    300

caggttcaag caattctcct gcctcagcct cccgagtagc tgggattaca ggcaccggcc    360

accacgccca gctaattttt ttatattttt agtagagatg gggtttcacc atgttggcca    420

ggctggtctt gaacttttcc cctcttatta taattcagac acttaacctg aaatatacct    480

tttcaaatga agtaaatggg cttacc                                          506
```

<210> SEQ ID NO 15
<211> LENGTH: 601
<212> TYPE: DNA
<213> ORGANISM: Homo sapiens

<400> SEQUENCE: 15

```
tattaaggga cttgggattc tcccttatct tgggcgtgtt tttcagcatt aactaaaact     60

taaaggaaag agttggatgg tcaagaaaag ctttttcctt aagtgatatg gacagtttct    120

caaggaggta gaaggggcag ccaggagaca aatcaaggag ccaacgaaat gagtgctacc    180

aagtcatagt cattcgctta tttttaaaaa atgcgtgtcc tgtatgccag gctctgcact    240

gagaccgaga gattccaaga tgaataatac ctacagtcac tgttctcaaa ttgtgcatta    300

yctaaaacac attacatgac catgctggcc actgatcgag gcacctttcc caggggcttt    360

ttttgtgaat taagaaaaca aggtaattca ccagttattg ccaagatagt ttggcttctt    420

ggctcatgtg gatatcacct aggccagtac ttttgtgatt tactgtgtac tccactttaa    480

cggcctgcga tcttctagag aagaacccgc cagggagcag tgagaggcct ccctggtaga    540

ctgagacact gactgtccct ccccctatcc ttttcgtctt tctggccagc agaccagcag    600

g                                                                     601
```

<210> SEQ ID NO 16
<211> LENGTH: 601
<212> TYPE: DNA
<213> ORGANISM: Homo sapiens

<400> SEQUENCE: 16

```
atgccaggtg ccatgctaag atttggggac acagtggtga ccaaaacaga cagaaaccaa     60

ggagctggct tacattccaa gggagtgcat aggaagctgt gtttcatttc agtttctgct    120

ctagtacccc cctttccctg gcagtgccag ggtctgagaa ggaagagtga ggtggtgagg    180

aggtgtgaag cagtggggtg acctgagagg agaggatggg gtggctttgc ctcaaggctt    240

gggcccctgc taggtgtcgc tctgcctcag gcctctgttt ctcctcctga cacaggcaca    300

ractcggcct cccacccctt ccccaaggac atgaccttgg gaaggaacat atctgaagcc    360

cgcggagggt ttccgctgct gtgcatctgt gccacagatc cgcagatgca cccacagctg    420

ggagcaccgg ttcctcccgc ctacctgcac tccctggttt ctgttccttc ctcctcctcc    480

ttccttctcc ccgctcccca gacaggctgg tgatgagctt tataacatga aagctgatat    540

ttggccatta tccttctacc ctgattgcca gctcttctca gagtgccttc ttctgtaatc    600

c                                                                     601
```

<210> SEQ ID NO 17
<211> LENGTH: 601
<212> TYPE: DNA
<213> ORGANISM: Homo sapiens

<400> SEQUENCE: 17

```
ctggtgaagg ctttgaagag gaagtgacat ttgagtggag tcttgaagac taggcaggat     60
tctccagggg ccctgggtgt gggggaagca cacatcctct tccctgtagg aggtgctgtg    120
gagaacacct ccagtggggc tgctactctt cagccttgct ggggccagct ggagtggcca    180
caccatggtc acaccagctg aagttcaaga agccccttgc caggagattg ctttgctggc    240
tctgggtgag ggcaggtgca tctggaagcc cccttctttc taagatgttt gctcctgagt    300
ytctatgtcc tagtcttttc ttccctgaac cttttgctac cagtcagcac agccctgcct    360
gagaaggagg ctggaggagt gagtggtcag tagcctggtg ggtcttggct gcctctgtgg    420
tgcccgctgg cctaagtagc aggcttaggg aggcgagacc cagttccagg ggctgccaat    480
ggggagcgag atggggtggc tggagcacac tgcacatgtc accaaggctc tagggaggtc    540
tgtgcacaag gcagtgggaa aagcaagggg aagacccagc ctggtcaaca tggtgaaacc    600
c                                                                    601
```

<210> SEQ ID NO 18
<211> LENGTH: 601
<212> TYPE: DNA
<213> ORGANISM: Homo sapiens

<400> SEQUENCE: 18

```
agatttgggt gaggacacag ccaaaccata tcagctcccg ggatccctgt gtgaatgggg     60
tctttttgg tgtttgaggg ctgcacaggg tgacctcttt agaggtgacc tcctgccaca    120
acccacagga ggtgcacatg gcccacacat gctggtttcc tgcagtggga ggggctgggg    180
cactcctggg acctgtgctt ggtaactgga gctggcctgg ccctggggat tgggtgtctg    240
ccttgggttt caggtgtatt aggttgttcc tcgttgtgga gtctcattac taatgaaaag    300
ytcaggtcgc actgctggtc ctttgggctg tggttgatcc tggtgataac atttggcacc    360
cagaggcagc cctgtttcca ctgaagcatg cggagcttgg ctggcaggca ggcaagctgg    420
cagctgccct taacccatga ggtgctggcc cgctagtagg cacaccctac ctgtgccaga    480
attgaggttg tagccagact ccaggagcca tctgggcccc acagggggcg gcatttcctc    540
tttttgttga aacattccag ccaagtgctg gcttgggctt catctctctg tcccactctc    600
c                                                                    601
```

<210> SEQ ID NO 19
<211> LENGTH: 601
<212> TYPE: DNA
<213> ORGANISM: Homo sapiens

<400> SEQUENCE: 19

```
ccctgtgtta tgggttttac accttatctc acaatcttaa aaaaaaaatt ctctgagaat     60
cctctgtcac ccccacttta caggtgagga aactgaggca aagataggct aactggcttc    120
cccaacacca tgcaggtaat tagtgataaa ggcagggttg gaaccaaact tgacctccca    180
attgtgctct taatggccag gacactctgt gtcttgagcc acacttcctc catgttttct    240
agggctttct agggaggcag acagtgatgg gaaggggtgt tctttagtgt ggatgtgccc    300
ygcctgctcc tttctgtaag cgtcacagca cctccactgc tgtactgggg aggcaccaag    360
tttttccctg tttgcccacc caaggcgagc tagcttagga gtcacgtgag tgctgggtgt    420
ctcgcctgct gcatccctct atcctgcccc tgcccccggt gcccagagga gggccctgcc    480
```

-continued

```
tgtcttccca gttctccaac agcagcgctg tcccagcacc ctcgggctcc agttgtggcc    540

tggcagctgc tggggcagac accatacaga cagagtcaca gcaggaagag gatggggccc    600

a                                                                    601


<210> SEQ ID NO 20
<211> LENGTH: 601
<212> TYPE: DNA
<213> ORGANISM: Homo sapiens

<400> SEQUENCE: 20

ggaaggggtg ttctttagtg tggatgtgcc ctgcctgctc ctttctgtaa gcgtcacagc     60

acctccactg ctgtactggg gaggcaccaa gtttttccct gtttgcccac ccaaggcgag    120

ctagcttagg agtcacgtga gtgctgggtg tctcgcctgc tgcatccctc tatcctgccc    180

ctgcccccgg tgcccagagg agggccctgc ctgtcttccc agttctccaa cagcagcgct    240

gtcccagcac cctcgggctc cagttgtggc ctggcagctg ctggggcaga caccatacag    300

mcagagtcac agcaggaaga ggatggggcc cagggctgct gcctcaggcc atggctgcat    360

ggcaccatca gttgattgag gagcttttct tgccaatgtc tgaggcatca ggtggcagga    420

cacgtctccc tgctcttaag cctcaggcat gcagcccttc ttatgctctc tggggtgagg    480

gggagatccc cctcatggaa ttgctttttt tttttttttt ttttttttga gacagggtcc    540

tgctctgtca ctcaggctgg agtgcagcct caacctccca gactcaagtg atcctcctgc    600

c                                                                    601


<210> SEQ ID NO 21
<211> LENGTH: 601
<212> TYPE: DNA
<213> ORGANISM: Homo sapiens
<220> FEATURE:
<221> NAME/KEY: variation
<222> LOCATION: (301)...(301)
<223> OTHER INFORMATION: 't' may be either present or absent

<400> SEQUENCE: 21

tctccaacag cagcgctgtc ccagcaccct cgggctccag ttgtggcctg gcagctgctg     60

gggcagacac catacagaca gagtcacagc aggaagagga tggggcccag ggctgctgcc    120

tcaggccatg gctgcatggc accatcagtt gattgaggag cttttcttgc caatgtctga    180

ggcatcaggt ggcaggacac gtctccctgc tcttaagcct caggcatgca gcccttctta    240

tgctctctgg ggtgaggggg agatcccct catggaattg cttttttttt tttttttttt    300

tttttgagac agggtcctgc tctgtcactc aggctggagt gcagcctcaa cctcccagac    360

tcaagtgatc ctcctgcctc agcctcccga gtagctggga ccacaggtgg acaccatcac    420

acctgggttt ttttgttttt tgttttttgt tttctagaga tggggtctca ctttcttgct    480

cagtctggtc tcgaactcct gggcgcaagc agtcctccca cctcgtcttc ccaaagtgtt    540

tggattacag gtgtgagcca ctgtgcttgg cctttttatt tatttagaat ttgttttgga    600

a                                                                    601


<210> SEQ ID NO 22
<211> LENGTH: 601
<212> TYPE: DNA
<213> ORGANISM: Homo sapiens

<400> SEQUENCE: 22

ggatgtttct tccatgacat atatagctct tgaaactact tctatctaat atcacccaca     60
```

-continued gtgctgttaa aaatacagat ttctgggcct caccctcaaa ttatgattca gtaggtctag 120
gcacgtcaag gtcattgttt ttgtctttgt tttaagtcac cccaggtgat tctaaagccg 180
aagctctgca aagcacacct tgagaaacag agaactcttg tgctctcgct ctcttgacac 240
ttcaggtgca aaacttttgt cctaatgtcg ttctcaaact tacgcatgtg tgagaatcac 300
ygtgagagct tattgaaact gattgcggga ccccatacct agagggcctg attctatagg 360
tctgaggtaa ggcccaagaa tttgcatatt tgcatttcgt tttcttttcc tttcttttct 420 ttttttttt ttttgagatg aagtctcacc ctgtcgccca gactggagtg cagtggcatg 480
atctcagctc actgcagcct ctgcctcctg ggttaaagcg attctcccca caccccagac 540
ccgctcctga gtagctggga ttacaggtgc ccgccaccat gactagctaa cgtttgtatt 600
t 601

<210> SEQ ID NO 23
<211> LENGTH: 601
<212> TYPE: DNA
<213> ORGANISM: Homo sapiens

<400> SEQUENCE: 23
aggcacgtca aggtcattgt ttttgtcttt gttttaagtc accccaggtg attctaaagc 60
cgaagctctg caaagcacac cttgagaaac agagaactct tgtgctctcg ctctcttgac 120
acttcaggtg caaaactttt gtcctaatgt cgttctcaaa cttacgcatg tgtgagaatc 180
actgtgagag cttattgaaa ctgattgcgg gaccccatac ctagagggcc tgattctata 240
ggtctgaggt aaggcccaag aatttgcata tttgcatttc gttttctttt cctttctttt 300
yttttttttt tttttgaga tgaagtctca ccctgtcgcc cagactggag tgcagtggca 360
tgatctcagc tcactgcagc ctctgcctcc tgggttaaag cgattctccc cacaccccag 420
acccgctcct gagtagctgg gattacaggt gcccgccacc atgactagct aacgtttgta 480
tttttagtag agacgggggt ttcaccatgt tggccaggct ggtctcaaac tcctgacctc 540
aggtgatcca ctcacctcag cctcccaagg tcttgggatt actggtgtga gccaccgcgt 600
g 601

<210> SEQ ID NO 24
<211> LENGTH: 601
<212> TYPE: DNA
<213> ORGANISM: Homo sapiens

<400> SEQUENCE: 24
tgcagcctct gcctcctggg ttaaagcgat tctccccaca ccccagaccc gctcctgagt 60
agctgggatt acaggtgccc gccaccatga ctagctaacg tttgtatttt tagtagagac 120
gggggtttca ccatgttggc caggctggtc tcaaactcct gacctcaggt gatccactca 180
cctcagcctc ccaaggtctt gggattactg gtgtgagcca ccgcgtgcgg ccagaatttg 240
catttctaac aagtcccagg tgatgctgat gctgtgggtc cagggacaca ctttgagaac 300
hgcttgttac tcaggcgata tgtggacagt agcgtcatct tcacctggga gcttcctgca 360
gcatctcagg ccttgcccta cacctaccag atcagaatct gcattttaac tcaatccccg 420
cgtgattctc atgcacctgg aagtttgaga aatatgacct tagaggagcc ggaatgtgaa 480
accactggag gcagagatag atggagaata tctcttcttc tcacggatac taaagatgca 540
acaaaaaggg ctgactctct gggtgtgcac ccaggtgggg ctgatgaccg aaaagaggcc 600

-continued

```
a                                                                  601

<210> SEQ ID NO 25
<211> LENGTH: 601
<212> TYPE: DNA
<213> ORGANISM: Homo sapiens

<400> SEQUENCE: 25

tgtgtgtgag gccggggagt gctgcgagcc ccggaattcc tcagccttag tcccccgcca    60

catagctaag aagtgaggga ggaggtgaga aggagtcact gcccagcctc acttccggtg   120

gagtaccctg tctccttgtc agttctgtct ctggggacag ttgcctgctt tcacctctcc   180

ctccatcccc tcttctctca cagggaaaaa ttcaccttaa tattggaagt tcctctccta   240

gcaaagtcct tctcaggcac ccacaggcaa aaaggaaact aagcagagtt agggcttcca   300

kgcctagcca actacacgac tctcctcttg cttccctaag aaccagcgca aggggcagcg   360

tgggttccag catagatgga cctgtgttgg aatctctgca cgtgctgtgc tgaccctggc   420

tagccattga cctctctgag cccttgtttc ctttccacta ggctctctga gggcaggggc   480

catgtctttt tcactgctct gtctgcactg agcactgtgc agggcacata ggaagttccc   540

ataaatgttt gtgggataaa ggaaataaaa ccttctctct tcctgtcccc cttgtgatgg   600

c                                                                  601

<210> SEQ ID NO 26
<211> LENGTH: 601
<212> TYPE: DNA
<213> ORGANISM: Homo sapiens

<400> SEQUENCE: 26

aaagtccttc tcaggcaccc acaggcaaaa aggaaactaa gcagagttag ggcttccagg    60

cctagccaac tacacgactc tcctcttgct tccctaagaa ccagcgcaag gggcagcgtg   120

ggttccagca tagatggacc tgtgttggaa tctctgcacg tgctgtgctg accctggcta   180

gccattgacc tctctgagcc cttgtttcct ttccactagg ctctctgagg gcaggggcca   240

tgtctttttc actgctctgt ctgcactgag cactgtgcag ggcacatagg aagttcccat   300

raatgtttgt gggataaagg aaataaaacc ttctctcttc ctgtccccct tgtgatggct   360

ttgcacaagg cactgtcctt ggccaggttt gctaggctag tgtgaggata aaccaggtat   420

attacaaatt ggagaaaatt tctcgttctt cttggaagaa ggtgctgtat catgaaacaa   480

gaatgtcttg attcccttct atgccaggta ctggggagaa acaggtgcct gataaccgtt   540

gatccaggca gaaataagca tactcctgct tcccaaggcc tgatgcttct ctccttcctc   600

c                                                                  601

<210> SEQ ID NO 27
<211> LENGTH: 601
<212> TYPE: DNA
<213> ORGANISM: Homo sapiens

<400> SEQUENCE: 27

ccttggatga agaagcgtgg gaactctttg cttcctttcc ctcccgcagt gacatgccat    60

gccatgccac tgcctcttca tctggtccta tgacagtcac tcataagcac ccgcatgtac   120

ccggccctgc actagctcat gacagctgca gtcaattggg ccaggtgctg tatctcatcc   180

ggcctcctca gcaaccctct gagatactgg taatgtccct gatgaagata tttactgagg   240

cagaaatgga cgctcagtga agcaaggtgc ctgatgttat agcaatgagc tatgagtggc   300
```

```
yagagggagg agataagctc aggcctgaca ccaaagccca tgctccttct agtcaaccac    360

agtgcctcct atggtgaatg agtgagtcag caaccaagac gcatgaggcc ttctttttgg    420

tgagccttgg ctgggtgctg aggcttcagg tacaatcatg ggttggaaga gccctcctct    480

ctctccacag tctggcacta tgaccccttc tggttattaa caaggcaaag agagagaggg    540

aagaaagcag gcaaataatg tgggttgcta ttcctagaga ttagaatttc aggaaggata    600

a                                                                    601
```

<210> SEQ ID NO 28
<211> LENGTH: 601
<212> TYPE: DNA
<213> ORGANISM: Homo sapiens

<400> SEQUENCE: 28

```
ttctctgacc cctcccctcc ggtgcgtttc gtatcaaagc tcctcaaacc ccgtccccg      60

tgtgtcctgc tgtgtgcagc tcgctctttc cttccttcct aagctatcca aggggatgga    120

cccaggctcg tggggaggtt ccacccttgg atccaggaag aaccctccac cctgcctcgt    180

gggtgggcca aaggctacag ggtgcttctt cctcttcccc cacccccact gtccctcatg    240

tgccatgggc ctgcctcccc agtgacctgc gaaagtggag catcgaggta ggagggaaac    300

rgcaaccagg gagtcctcga gcctggggct gccctacctc tacccattcc ccgaccagag    360

ctttgccctt gcttggctgc ccgcctgcct ctttggggaa ctgagctcag aggcaggtgc    420

ttcagagaag gaaacaaaat gaggggtggc agggataaaa agtcacctcc attctctacc    480

tcccatgcag catgaacaca atttctctcc acctggctcc caaatttaaa gatgtggacc    540

aaggcctgtg ggtactccag ggcaaggag agccctgggg tcagtgacac tgtcaggcca     600

a                                                                    601
```

<210> SEQ ID NO 29
<211> LENGTH: 601
<212> TYPE: DNA
<213> ORGANISM: Homo sapiens

<400> SEQUENCE: 29

```
acccctcccc tccggtgcgt ttcgtatcaa agctcctcaa accccgtccc ccgtgtgtcc     60

tgctgtgtgc agctcgctct ttccttcctt cctaagctat ccaaggggat ggacccaggc    120

tcgtggggag gttccaccct tggatccagg aagaaccctc caccctgcct cgtgggtggg    180

ccaaaggcta cagggtgctt cttcctcttc ccccaccccc actgtccctc atgtgccatg    240

ggcctgcctc cccagtgacc tgcgaaagtg gagcatcgag gtaggaggga aacggcaacc    300

rgggagtcct cgagcctggg gctgccctac ctctacccat tccccgacca gagctttgcc    360

cttgcttggc tgcccgcctg cctctttggg gaactgagct cagaggcagg tgcttcagag    420

aaggaaacaa aatgaggggt ggcagggata aaaagtcacc tccattctct acctcccatg    480

cagcatgaac acaatttctc tccacctggc tcccaaattt aaagatgtgg accaaggcct    540

gtgggtactc caggggcaag gagagccctg gggtcagtga cactgtcagg ccaaccatgc    600

a                                                                    601
```

<210> SEQ ID NO 30
<211> LENGTH: 601
<212> TYPE: DNA
<213> ORGANISM: Homo sapiens -continued

<400> SEQUENCE: 30

```
gccagggact tgagaagtta tattgggcag tggctccaat ctgtggacca gtatttcagc     60
tttccctgaa gatcaggcag ggtgccattc attgtctttc tctcctagcc ccctcaggaa    120
agaaggacta tatttgtact gtaccctagg ggttctggaa gggaaaacat ggaatcagga    180
ttctatagac tgataggccc tatccacaag ggccatgact gggaaaaggt atgggagcag    240
aaggagaatt gggattttag ggtgcagcta cgctcaccct aaacttttgg tggcctgggg    300
yatgtcttga ggcccagact gttaaccagg ctctgctggc ctgtttactc gtcaccacct    360
ctgcacctgc tgtcttgaga ctccatccag ccccaggcac gccacctgct cctgagcctc    420
cactatctcc ctgtgacggg tgaacttcgt gtactgtgtc tcgggtccat atatgaattg    480
tgagcagggt tcatctattt taaacacaga tgtttacaaa ataaagatta tttcaaacca    540
ccggtgtggc tgcctggatg agtccttggg ggtaggtctc actcagaccc tggcagtgat    600
g                                                                    601
```

<210> SEQ ID NO 31
<211> LENGTH: 601
<212> TYPE: DNA
<213> ORGANISM: Homo sapiens

<400> SEQUENCE: 31

```
ggcagtggct ccaatctgtg gaccagtatt tcagctttcc ctgaagatca ggcagggtgc     60
cattcattgt ctttctctcc tagccccctc aggaaagaag gactatattt gtactgtacc    120
ctaggggttc tggaagggaa aacatggaat caggattcta tagactgata ggccctatcc    180
acaagggcca tgactgggaa aaggtatggg agcagaagga gaattgggat tttagggtgc    240
agctacgctc accctaaact tttggtggcc tggggcatgt cttgaggccc agactgttaa    300
scaggctctg ctggcctgtt tactcgtcac cacctctgca cctgctgtct tgagactcca    360
tccagcccca ggcacgccac ctgctcctga gcctccacta tctccctgtg acgggtgaac    420
ttcgtgtact gtgtctcggg tccatatatg aattgtgagc agggttcatc tattttaaac    480
acagatgttt acaaaataaa gattatttca aaccaccggt gtggctgcct ggatgagtcc    540
ttgggggtag gtctcactca gaccctggca gtgatgtggg agggagagag gcagtgctgg    600
t                                                                    601
```

<210> SEQ ID NO 32
<211> LENGTH: 601
<212> TYPE: DNA
<213> ORGANISM: Homo sapiens

<400> SEQUENCE: 32

```
ctgctggcct gtttactcgt caccacctct gcacctgctg tcttgagact ccatccagcc     60
ccaggcacgc cacctgctcc tgagcctcca ctatctccct gtgacgggtg aacttcgtgt    120
actgtgtctc gggtccatat atgaattgtg agcagggttc atctatttta aacacagatg    180
tttacaaaat aaagattatt tcaaaccacc ggtgtggctg cctggatgag tccttggggg    240
taggtctcac tcagaccctg gcagtgatgt gggagggaga gaggcagtgc tggtagaagc    300
rgctccagaa gcaaaggcaa cagcagtaga gtgaccacgg aagcggcaaa cattgtcttc    360
ccttctctac cttccctagt gccacctgca gggaggccca aagcaaagcc ccgttgccct    420
gcattgggct ggcactgcag aaataagatg aaacacagtt atcgagagga tgctgaacat    480
ctatgagcag gttttaaagc caagatgagt ctcatctgtt tgtgtgggtc aggaacgggt    540
```

-continued

```
cttcctgaag gcatgaggtg ggactggata atctttcaga tttgtgattg gatacctcgg    600

g                                                                    601


<210> SEQ ID NO 33
<211> LENGTH: 601
<212> TYPE: DNA
<213> ORGANISM: Homo sapiens

<400> SEQUENCE: 33

gcacgccacc tgctcctgag cctccactat ctccctgtga cgggtgaact tcgtgtactg     60

tgtctcgggt ccatatatga attgtgagca gggttcatct attttaaaca cagatgttta    120

caaaataaag attatttcaa accaccggtg tggctgcctg gatgagtcct tgggggtagg    180

tctcactcag accctggcag tgatgtggga gggagagagg cagtgctggt agaagcagct    240

ccagaagcaa aggcaacagc agtagagtga ccacggaagc ggcaaacatt gtcttccctt    300

stctaccttc cctagtgcca cctgcaggga ggcccaaagc aaagccccgt tgccctgcat    360

tgggctggca ctgcagaaat aagatgaaac acagttatcg agaggatgct gaacatctat    420

gagcaggttt taaagccaag atgagtctca tctgtttgtg tgggtcagga acgggtcttc    480

ctgaaggcat gaggtgggac tggataatct ttcagatttg tgattggata cctcggggga    540

gcagaggcag actgggatct caggactgca ggtatttcat actttgggat atggaattga    600

t                                                                    601


<210> SEQ ID NO 34
<211> LENGTH: 7
<212> TYPE: PRT
<213> ORGANISM: Homo sapiens
<220> FEATURE:
<221> NAME/KEY: VARIANT
<222> LOCATION: (1)...(7)
<223> OTHER INFORMATION: Xaa = Any Amino Acid

<400> SEQUENCE: 34

Gly Xaa Xaa Xaa Xaa Gly Lys
 1               5


<210> SEQ ID NO 35
<211> LENGTH: 5
<212> TYPE: PRT
<213> ORGANISM: Homo sapiens

<400> SEQUENCE: 35

Asp Thr Ala Gly Gln
 1               5


<210> SEQ ID NO 36
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 36

Asn Lys Xaa Asp
 1


<210> SEQ ID NO 37
<211> LENGTH: 5
```

-continued

```
<212> TYPE: PRT
<213> ORGANISM: Homo sapiens
<220> FEATURE:
<221> NAME/KEY: VARIANT
<222> LOCATION: (1)...(5)
<223> OTHER INFORMATION: Xaa = Any Amino Acid

<400> SEQUENCE: 37

Glu Xaa Ser Ala Xaa
 1              5


<210> SEQ ID NO 38
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 38

Cys Ala Ala Xaa
 1
```